(12) United States Patent
Wheeler et al.

(10) Patent No.: US 11,866,783 B2
(45) Date of Patent: Jan. 9, 2024

(54) EXTRACELLULAR MRNA MARKERS OF MUSCULAR DYSTROPHIES IN HUMAN URINE

(71) Applicant: The General Hospital Corporation, Boston, MA (US)

(72) Inventors: Thurman Wheeler, Boston, MA (US); Xandra O. Breakefield, Newton Center, MA (US); Leonora Balaj, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 606 days.

(21) Appl. No.: 16/318,658

(22) PCT Filed: Jul. 21, 2017

(86) PCT No.: PCT/US2017/043348
§ 371 (c)(1),
(2) Date: Jan. 17, 2019

(87) PCT Pub. No.: WO2018/017991
PCT Pub. Date: Jan. 25, 2018

(65) Prior Publication Data
US 2019/0284628 A1 Sep. 19, 2019

Related U.S. Application Data

(60) Provisional application No. 62/365,139, filed on Jul. 21, 2016.

(51) Int. Cl.
C12Q 1/68 (2018.01)
C07H 21/04 (2006.01)
(Continued)

(52) U.S. Cl.
CPC ......... *C12Q 1/6883* (2013.01); *C12Q 1/6865* (2013.01); *G01N 33/50* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2002/0061571 A1 5/2002 Mahadevan
2006/0057624 A1* 3/2006 Potashkin ............... C12Q 1/68
(Continued)

FOREIGN PATENT DOCUMENTS

DE 102006007249 8/2007
WO WO 2009/111704 9/2009
(Continued)

OTHER PUBLICATIONS

Frearson et al. Proteins in the urine associated with Duchenne muscular dystrophy and other neuromuscular disease (1981) Clinical Science 61, 141-149. (Year: 1981).*
(Continued)

*Primary Examiner* — Jeanine A Goldberg
(74) *Attorney, Agent, or Firm* — Fish & Richardson P.C.

(57) ABSTRACT

Described herein are methods for diagnosing and monitoring subjects with diseases associated with aberrant splicing, based upon detecting properly spliced isoforms and mis-spliced isoforms in a urine sample from the subject.

3 Claims, 32 Drawing Sheets

(51) Int. Cl.
    *C12Q 1/6883*  (2018.01)
    *C12Q 1/6865*  (2018.01)
    *G01N 33/50*  (2006.01)

(56) References Cited

U.S. PATENT DOCUMENTS

| | | |
|---|---|---|
| 2009/0155276 A1 | 6/2009 | Lai et al. |
| 2015/0232933 A1 | 8/2015 | Kopreski |

FOREIGN PATENT DOCUMENTS

| | | | |
|---|---|---|---|
| WO | WO 2015/082372 | 6/2015 | |
| WO | WO-2015082372 A1 * | 6/2015 | ........... C12Q 1/6886 |
| WO | WO 2015/187825 | 12/2015 | |
| WO | WO 2015/190921 | 12/2015 | |

OTHER PUBLICATIONS

Su et al. Human Urine Contains Small, 150 to 250 Nucleotide-Sized, Soluble DNA Derived from Circulation and May Be Useful in the Detection of Colon Cancer (2004) J. Mol. Diagn. 6(2): 101-107. (Year: 2004).*
Nakamori et al. Splicing Biomarkers of Disease Severity in Myotonic Dystrophy (2013) Ann Neurol 74:862-872. (Year: 2013).*
Gaggl et al. Screening for Fabry Disease by urinary Globotriaosylceramide Isoforms Measurement in Patients with Left Ventricular Hypertrophy (2016) Int. J. Med. Sci. vol. 13, pp. 340-346. (Year: 2016).*
Antoury et al. Genetic markers of myotonic dystrophy type 1 (DM1) and Duchenne muscular dystrophy (DMD) in human urine (S42.005) (2017) Neurology 88 (16 Supplement) (Year: 2017).*
Antoury et al. (Nature Communications, vol. 9, No. 3906, 2018) (Year: 2018).*
Zhao et al. (Cancer Research, vol. 69, No. 19, Oct. 2009, pp. 7696-7703). (Year: 2009).*
Antoury et al., "Analysis of extracellular mRNA in human urine reveals splice variant biomarkers of muscular dystrophies," Nature Communications, Sep. 2018, 9(1), 16 pages.
Antoury et al., "Exosomes in human urine contain mRNA splice variant biomarkers of muscular dystrophies," Molecular Therapy, May 2018, 26(5S1):391.
Antoury et al., "Urine mRNA to identify a novel pseudoexon causing dystrophinopathy," Annals of Clinical and Translational Neurology, May 2019, 6(6):1106-1112.
European Supplementary European Search Report in EP Appln. No. EP 17831981, dated Jan. 8, 2020, 10 pages.
Kaito et al., "Detection of a Transcript Abnormality in mRNA of the SLC12A3 Gene Extracted From Urinary Sediment Cells of a Patient with Gitelman's Syndrome," Pediatric Research, Jan. 2007, 61(4):502-505.
Shen et al., "SURVIV for survival analysis of mRNA isoform variation," Nature Communications, Jun. 2016, 7(1), pp. 1-11.
Tao et al., "CD44-SLC1A2 Gene Fusions in Gastric Cancer," Science Translational Medicine, Apr. 2011, 3(77):77ra30-77ra30.
Waltering et al., "Androgen receptor (AR) aberrations in castration-resistant prostate cancer," Molecular and Cellular Endocrinology, Dec. 2011, 360(1):38-43.
Aartsma-Rus et al., "FDA approves eteplirsen for Duchenne muscular dystrophy: the next chapter in the eteplirsen saga," Nucleic Acid Therapeutics, Feb. 1, 2017, 27(1):1-3.
Aartsma-Rus et al., "The importance of genetic diagnosis for Duchenne muscular dystrophy," Journal of Medical Genetics, Mar. 1, 2016, 53(3):145-51.
Aartsma-Rus et al., "Translational and regulatory challenges for exon skipping therapies," Human Gene Therapy. Sep. 3, 2014, 25(10):885-92.
Aartsma-Rus, "Overview on DMD exon skipping," Exon Skipping, Humana Press, 2012, 97-116.

Aoi et al., "Muscle-enriched microRNA miR-486 decreases in circulation in response to exercise in young men," Frontiers in Physiology, Apr. 11, 2013, 4:80, 7 pages.
Bai et al.. "Aberrant RNA splicing in sporadic amyotrophic lateral sclerosis," Neuron, Mar. 1, 1998, 20(3):363-6.
Bennett & Swayze., "RNA targeting therapeutics: molecular mechanisms of antisense oligonucleotides as a therapeutic platform," Annu. Rev. Pharmacol. Toxicol., Feb. 2010, 50:259-293.
Bisset et al., "Therapeutic impact of systemic AAV-mediated RNA interference in a mouse model of myotonic dystrophy," Hum. Mol. Genet., Jun. 2015, 24(17):4971-4983.
Boca et al., "Discovery of Metabolic Biomarkers for Duchenne Muscular Dystrophy within a Natural History Study," PLoS One, Apr. 2016, 11(4):e0153461.
Brolin et al., "Antisense mediated exon skipping therapy for Duchenne muscular dystrophy (DMD)," Artificial DNA: PNA & XNA, Jan. 1, 2011, 2(1):6-15.
Burghes et al., "Antisense oligonucleotides and spinal muscular atrophy: skipping along," Genes & Development, Aug. 1, 2010, 24(15):1574-9.
Cavazzana-Calvo et al., "Gene therapy of human severe combined immunodeficiency (SCID)-X1 disease," Science, Apr. 28, 2000, 288(5466):669-72.
Charlet et al., "Loss of the muscle-specific chloride channel in type 1 myotonic dystrophy due to misregulated alternative splicing," Mol. Cell, Jul. 2002, 10(1):45-53.
Chen et al., "BEAMing and droplet digital PCR analysis of mutant IDH1 mRNA in glioma patient serum and cerebrospinal fluid extracellular vesicles," Molecular Therapy—Nucleic Acids, Jan. 1, 2013, 2:e109, 10 pages.
Childs-Disney et al., "Induction and reversal of myotonic dystrophy type 1 pre-mRNA splicing defects by small molecules," Nat. Commun., Jun. 2013, 4:2044, 11 pages.
Cirak et al., "Exon skipping and dystrophin restoration in patients with Duchenne muscular dystrophy after systemic phosphorodiamidate morpholino oligomer treatment: an open-label, phase 2, dose-escalation study," Lancet, Aug. 2011, 378(9791):595-605.
Coonrod et al., "Reducing levels of toxic RNA with small molecules," ACS Chem. Biol., Sep. 2013, 8(11):2528-2537.
Cornetta et al., "Replication-competent lentivirus analysis of clinical grade vector products," Molecular Therapy, March, 1 2011, 19(3):557-66.
Davis et al., "Expansion of a CUG trinucleotide repeat in the 3' untranslated region of myotonic dystrophy protein kinase transcripts results in nuclear retention of transcripts," Proceedings of the National Academy of Sciences, July, 8 1997, 94(14):7388-93.
Disney, "Rational design of chemical genetic probes of RNA function and lead therapeutics targeting repeating transcripts," Drug Discov. Today, Dec. 2013, 18(23-24):1228-1236.
Dreyfuss et al., "SMN Deficiency in SMA: Splicing Gone Awry," Eukaryon, 2010, 6(1):75-79.
Du et al., "Aberrant alternative splicing and extracellular matrix gene expression in mouse models of myotonic dystrophy," Nat. Struct. Moll. Biol., Feb. 2010, 17(2)187-193.
Erdbrügger et al., "Extracellular vesicles in renal diseases: more than novel biomarkers?," Journal of the American Society of Nephrology, Jan. 1, 2016, 27(1):12-26.
Eriksson et al., "Recurrent de novo point mutations in lamin A cause Hutchinson-Gilford progeria syndrome," Nature, May 2003, 423(6937):293-8.
Flanigan et al., "Nonsense mutation-associated Becker muscular dystrophy : interplay between exon definition and splicing regulatory elements within the DMD gene," Human Mutation, Mar. 2011, 32(3):299-308.
Fletcher et al., "Targeted exon skipping to address "leaky" mutations in the dystrophin gene," Molecular Therapy—Nucleic Acids, Jan. 1, 2012, 1;1:e48, 11 pages.
Forterre et al., "Myotube-derived exosomal miRNAs downregulate Sirtuin1 in myoblasts during muscle cell differentiation," Cell cycle. Jan. 1, 2014, 13(1):78-89.
François et al., "Selective silencing of mutated mRNAs in DM1 by using modified hU7-snRNAs," Nature structural & molecular biology, Jan. 2011, 18(1):85-7.

(56) References Cited

OTHER PUBLICATIONS

Francois et al., "Selective silencing of mutated mRNAs in DM1 by using modified hU7-snRNAs," Nat. Struct. Mol. Biol., Jan. 2011, 18(1):85-87.

Freyermuth et al., "Splicing misregulation of SCN5A contributes to cardiac-conduction delay and heart arrhythmia in myotonic dystrophy," Nat. Commun., Apr. 2016, 7:11067, 7 pages.

Furling et al., "Viral vector producing antisense RNA restores myotonic dystrophy myoblast functions," Gene Therapy, May 2003, 10(9):795-802.

Gao et al., "Antisense oligonucleotides: rising stars in eliminating RNA toxicity in myotonic dystrophy," Human Gene Therapy, Dec. 19, 2012, 24(5):499-507.

Genschel et al., "Mutations in the LMNA gene encoding lamin A/C," Human Mutation, Dec. 2000, 16(6):451-9.

Goemans et al., "Systemic administration of PRO051 in Duchenne's muscular dystrophy," N. Engl. J. Med., Apr. 2011, 364(16):1513-1522.

Goodwin et al., "MBNL Sequestration by Toxic RNAs and RNA Misprocessing in the Myotonic Dystrophy Brain," Cell Reports, Aug. 2015, 12(7):1159-1168.

Hathout et al., "Clinical utility of serum biomarkers in Duchenne muscular dystrophy," Clinical Proteomics, Dec. 2016, 13(1), 9 pages.

Hondaet et al., "The ALS/FTLD-related RNA-binding proteins TDP-43 and FUS have common downstream RNA targets in cortical neurons," FEBS Open Bio, Jan. 1, 2014, 4(1), 10 pages.

Honig et al., "Glutamate transporter EAAT2 splice variants occur not only in ALS, but also in AD and controls," Neurology, Oct. 24, 2000, 55(8):1082-8.

Hua et al., "Peripheral SMN restoration is essential for long-term rescue of a severe spinal muscular atrophy mouse model," Nature. Oct. 2011, 478(7367):123-6.

Imbeaud et al., "Towards standardization of RNA quality assessment using user-independent classifiers of microcapillary electrophoresis traces," Nucleic Acids Research, Jan. 1, 2005, 33(6):e56, 12 pages.

Imbert et al., "Viral vector-mediated antisense therapy for genetic diseases," Genes, Feb. 2017, 8(2):51, 19 pages.

Ionis Pharmaceuticals I, "A Safety and Tolerability Study of Multiple Doses of ISIS-DMPKRx in Adults With Myotonic Dystrophy Type 1," ClinicalTrials.Gov, National Library of Medicine, <http://clinicaltrials.gov/show/NCT02312011>, 2014, 8 pages.

Järver et al., "A chemical view of oligonucleotides for exon skipping and related drug applications," Nucleic Acid Therapeutics, Feb. 1, 2014, 24(1):37-47.

Kanadia et al., "A muscleblind knockout model for myotonic dystrophy," Science, Dec. 12, 2003, 302(5652):1978-80.

Kanadia et al., "Reversal of RNA missplicing and myotonia after muscleblind overexpression in a mouse poly(CUG) model for myotonic dystrophy," Proc. Natl. Acad. Sci. USA., Aug. 2006, 103(31):11748-11753.

Khan et al., "Early diagnostic value of survivin and its alternative splice variants in breast cancer," BMC Cancer, Dec. 2014, 14(1):176, 10 pages.

Kinali et al., "Local restoration of dystrophin expression with the morpholino oligomer AVI-4658 in Duchenne muscular dystrophy: a single-blind, placebo-controlled, dose-escalation, proof-of-concept study," The Lancet Neurology, Oct. 1, 2009, 8(10):918-28.

Koo et al., "Clinical trials using antisense oligonucleotides in Duchenne muscular dystrophy," Human Gene Therapy, Mar. 22, 2013, 24(5):479-88.

Koressaar et al., "Enhancements and modifications of primer design program Primer3," Bioinformatics, Mar. 22, 2007, 23(10):1289-91.

Lee et al., "Modulation of LMNA splicing as a strategy to treat prelamin A diseases," The Journal of Clinical Investigation, Apr. 1, 2016, 126(4):1592-602.

Lee et al., "RNase H-mediated degradation of toxic RNA in myotonic dystrophy type 1," Proc. Natl. Acad. Sci. USA., Mar. 2012, 109(11):4221-4226.

Lefebvre et al., "Identification and characterization of a spinal muscular atrophy-determining gene," Cell, Jan. 13, 1995, 80(1):155-65.

Leger et al., "Systemic delivery of a Peptide-linked morpholino oligonucleotide neutralizes mutant RNA toxicity in a mouse model of myotonic dystrophy," Nucleic Acid Ther., Apr. 2013, 23(2):109-117.

Lin et al., "Aberrant RNA processing in a neurodegenerative disease: the cause for absent EAAT2, a glutamate transporter, in amyotrophic lateral sclerosis," Neuron, Mar. 1, 1998, 20(3):589-602.

Lin et al., "Failure of MBNL1-dependent post-natal splicing transitions in myotonic dystrophy." Human Molecular Genetics, May 22, 2006, 15(13):2087-97.

Lorson et al., "A single nucleotide in the SMN gene regulates splicing and is responsible for spinal muscular atrophy," Proceedings of the National Academy of Sciences, May 25, 1999, 96(11):6307-11.

Lueck et al., "Chloride channelopathy in myotonic dystrophy resulting from loss of posttranscriptional regulation for CLCN1," Am. J. Physiol. Cell Physiol., Apr. 2007, 292(4):C1291-1297.

Magaña et al., "Perspectives on gene therapy in myotonic dystrophy type 1," Journal of Neuroscience Research, Mar. 2011, 89(3):275-85.

Mankodi et al., "Expanded CUG repeats trigger aberrant splicing of ClC-1 chloride channel pre-mRNA and hyperexcitability of skeletal muscle in myotonic dystrophy," Mol. Cell, Jun. 2002, 10(1):35-44.

Mankodi et al., "Myotonic dystrophy in transgenic mice expressing an expanded CUG repeat." Science, Sep. 8, 2000, 289(5485):1769-72.

McClorey et al., "Splicing intervention for Duchenne muscular dystrophy," Current Opinion in Pharmacology, Oct. 1, 2005, G5(5):529-34.

McNally et al., "Welcome to the splice age: antisense oligonucleotide—mediated exon skipping gains wider applicability," The Journal of Clinical Investigation, Apr. 1, 2016, 126(4):1236-8.

Mendell et al., "Eteplirsen for the treatment of Duchenne muscular dystrophy," Annals of Neurology, Nov. 2013, 74(5):637-47.

Mendell et al., "Evidence-based path to newborn screening for Duchenne muscular dystrophy," Ann. Neural., Mar. 2012, 71(3):304-313.

Meyer et al., "The RNA of the glutamate transporter EAAT2 is variably spliced in amyotrophic lateral sclerosis and normal individuals," Journal of the Neurological Sciences, Nov. 15, 1999, 170(1):45-50.

Miranda et al., "Massively parallel sequencing of human urinary exosome/microvesicle RNA reveals a predominance of non-coding RNA," PloS one, May 9, 2014, (5):e96094, 10 pages.

Moeller et al., "Renal albumin filtration: alternative models to the standard physical barriers," Nature Reviews Nephrology, May 2013, 9(5):266-277.

Morcos et al., "Vivo-Morpholinos: a non-peptide transporter delivers Morpholinos into a wide array of mouse tissues," Biotechniques, Dec. 2008, G45(6):613-6, 618, 620-3.

Motamedinia et al., "Urine exosomes for non-invasive assessment of gene expression and mutations of prostate cancer," PLoS One, May 4, 2016, 11(5):e0154507, 15 pages.

Mulderset al., "Triplet-repeat oligonucleotide-mediated reversal of RNA toxicity in myotonic dystrophy," Proceedings of the National Academy of Sciences, Aug. 18, 2009, 106(33):13915-20.

Musova et al., "Highly unstable sequence interruptions of the CTG repeat in the myotonic dystrophy gene," American Journal of Medical Genetics Part A, Jul. 2009, 149(7):1365-74.

Nakamori et al., "Splicing biomarkers of disease severity in myotonic dystrophy," Annals of Neurology, Dec. 2013, 74(6):862-72.

Neeb et al., "Splice variant transcripts of the anterior gradient 2 gene as a marker of prostate cancer," Oncotarget, Sep. 5, 2014, (18):8681-9.

Nigro et al., "Genetic basis of limb-girdle muscular dystrophies: the 2014 update," Acta Myologica, May 2014, 33(1), 12 pages.

Nilsson et al., "A. Prostate cancer-derived urine exosomes: a novel approach to biomarkers for prostate cancer," British Journal of cancer, May 2009, 100(10):1603-7.

(56) References Cited

OTHER PUBLICATIONS

Noerholm et al., "RNA expression patterns in serum microvesicles from patients with glioblastoma multiforme and controls," BMC cancer. Dec. 2012, 12(1), 11 pages.

Orozco et al., "FUS-mediated alternative splicing in the nervous system: consequences for ALS and FTLD," Journal of Molecular Medicine, Dec. 1, 2013, 91(12):1343-54.

Pandey et al., "Identification and characterization of modified antisense oligonucleotides targeting DMPK in mice and nonhuman primates for the treatment of myotonic dystrophy type 1," Journal of Pharmacology and Experimental Therapeutics, Nov. 1, 2015, 355(2):310-21.

PCT International Preliminary Report on Patentability in International Application No. PCT/US2017/043348, dated Oct. 19, 2017, 7 pages.

PCT International Search Report and Written Opinion in International Application No. PCT/US2017/043348, dated Oct. 19, 2017, 10 pages.

Petek et al., "A cross sectional study of two independent cohorts identifies serum biomarkers for facioscapulohumeral muscular dystrophy (FSHD)," Neuromuscul Disorders, Jul. 2016, 26(7):405-413.

Philips et al., "Disruption of splicing regulated by a CUG-binding protein in myotonic dystrophy," Science, May 1998, 280(5364):737-741.

Rahimov et al., "Transcriptional profiling in facioscapulohumeral muscular dystrophy to identify candidate biomarkers," Proc. Natl. Acad. Sci. USA., Oct. 2012, 109(40):16234-16239.

Rodriguez et al., "Increased expression of the Hutchinson-Gilford progeria syndrome truncated lamin A transcript during cell aging." European Journal of Human Genetics, Jul. 2009, 17(7):928-37.

Romancino et al., "Identification and characterization of the nano-sized vesicles released by muscle cells," FEBS Letters, May 2013, 587(9):1379-84.

Rothstein et al., "Selective loss of glial glutamate transporter GLT-1 in amyotrophic lateral sclerosis," Annals of Neurology: Official Journal of the American Neurological Association and the Child Neurology Society, Jul. 1995, 38(1):73-84.

San Lucas et al., "Minimally invasive genomic and transcriptomic profiling of visceral cancers by next-generation sequencing of circulating exosomes," Annals of Oncology, Dec. 17, 2015, 27(4):635-41.

Savkur et al., "Aberrant regulation of insulin receptor alternative splicing is associated with insulin resistance in myotonic dystrophy," Nature Genetics, Aug. 27, 2001, 29(1):40-7.

Scotti et al., "RNA mis-splicing in disease," Nature Reviews Genetics, Jan. 2016, 17(1):19-32.

Siva et al., "Exon-skipping antisense oligonucleotides to correct missplicing in neurogenetic diseases," Nucleic Acid Therapeutics, Feb. 1, 2014, 24(1):69-86.

Skog et al., "Glioblastoma microvesicles transport RNA and proteins that promote tumour growth and provide diagnostic biomarkers," Nature Cell Biology, Dec. 2008, 10(12):1470-6.

Sobczak et al., "RNA interference targeting CUG repeats in a mouse model of myotonic dystrophy," Moll. Ther., Feb. 2013, 21(2):380-387.

Thornton et al., "Myotonic dystrophy: approach to therapy," Current Opinion in Genetics & Development, Jun. 1, 2017, 44:135-40.

Tiscornia et al., "Myotonic dystrophy: the role of the CUG triplet repeats in splicing of a novel DMPK exon and altered cytoplasmic DMPK mRNA isoform ratios," Molecular Cell, Jun. 1, 2000, 5(6):959-67.

Tkach et al., "Communication by extracellular vesicles: where we are and where we need to go," Cell, Mar. 10, 2016, 164(6):1226-32.

Touznik et al., "New developments in exon skipping and splice modulation therapies for neuromuscular diseases," Expert Opinion on Biological Therapy, Jun. 1, 2014, 14(6):809-19.

Untergasser et al., "Primer3—new capabilities and interfaces," Nucleic Acids Research, Jun. 21, 2012, 40(15):e115, 12 pages.

Urquidi et al., "Urinary mRNA biomarker panel for the detection of urothelial carcinoma," Oncotarget, Jun. 21, 2016, 7(25):38731-40.

Voit et al., "Safety and efficacy of drisapersen for the treatment of Duchenne muscular dystrophy (Demand II): an exploratory, randomised, placebo-controlled phase 2 study," The Lancet Neurology, Oct. 1, 2014, 13(10):987-96.

Wagner et al., "Dose-dependent regulation of alternative splicing by MBNL proteins reveals biomarkers for myotonic dystrophy," PLoS Genetics, Sep. 28, 2016, 12(9):e1006316, 24 pages.

Warf et al., "Pentamidine reverses the splicing defects associated with myotonic dystrophy," Proc. Natl. Acad. Sci. USA., Nov. 2009, 106(44):18551-18556.

Wehrens et al., The pls package: principal component and partial least squares regression in R, Journal of Statistical Software, Jan. 2007, 18(2), 23 pages.

Welch et al., "PTC124 targets genetic disorders caused by nonsense mutations," Nature, May 2007, 447(7140):87-91.

Wheeler et al., "Correction of CIC-1 splicing eliminates chloride channelopathy and myotonia in mouse models of myotonic dystrophy," J. Clin. Invest., Dec. 2007, 117(12):3952-3957.

Wheeler et al., "Reversal of RNA dominance by displacement of protein sequestered on triplet repeat RNA," Science, Jul. 17, 2009, 325(5938):336-9.

Wheeler et al., "Targeting nuclear RNA for in vivo correction of myotonic dystrophy," Nature, Aug. 2012, 488(7409):111-5.

Wojtkowiak-Szlachcic et al., "Short antisense-locked nucleic acids (all-LNAs) correct alternative splicing abnormalities in myotonic dystrophy," Nucleic Acids Research, Mar. 9, 2015, 43(6):3318-31.

Wood et al., "RNA-targeted splice-correction therapy for neuromuscular disease," Brain, Feb. 11, 2010, 133(4):957-72.

Wood., "To skip or not to skip: that is the question for Duchenne muscular dystrophy," Mol, Ther., Dec. 2013, 21(21):2131-2132.

Zhou et al., "ALS-associated FUS mutations result in compromised FUS alternative splicing and autoregulation, " PLoS Genetics, Oct. 31, 2013, 9(10):e1003895, 17 pages.

* cited by examiner

DMD gene with c9807 + 6 t > g substitution mutation:

...CTTCCAATTTgtaaggtatt...//...gtcttgcagGCTAATAATA...

ex 67 { ········ intron 67 ········ } ex 68

Cryptic splice site mRNA

...CUUCCAAUUUguaagGCUAAUAAUA... 🛑 ex 67      ex 68

↓

Truncated poorly functional protein

+

Normal splicing

...CUUCCAAUUUGCUAAUAAUA...

ex 67      ex 68

↓

Normal dystrophin protein

*FIG. 6E*

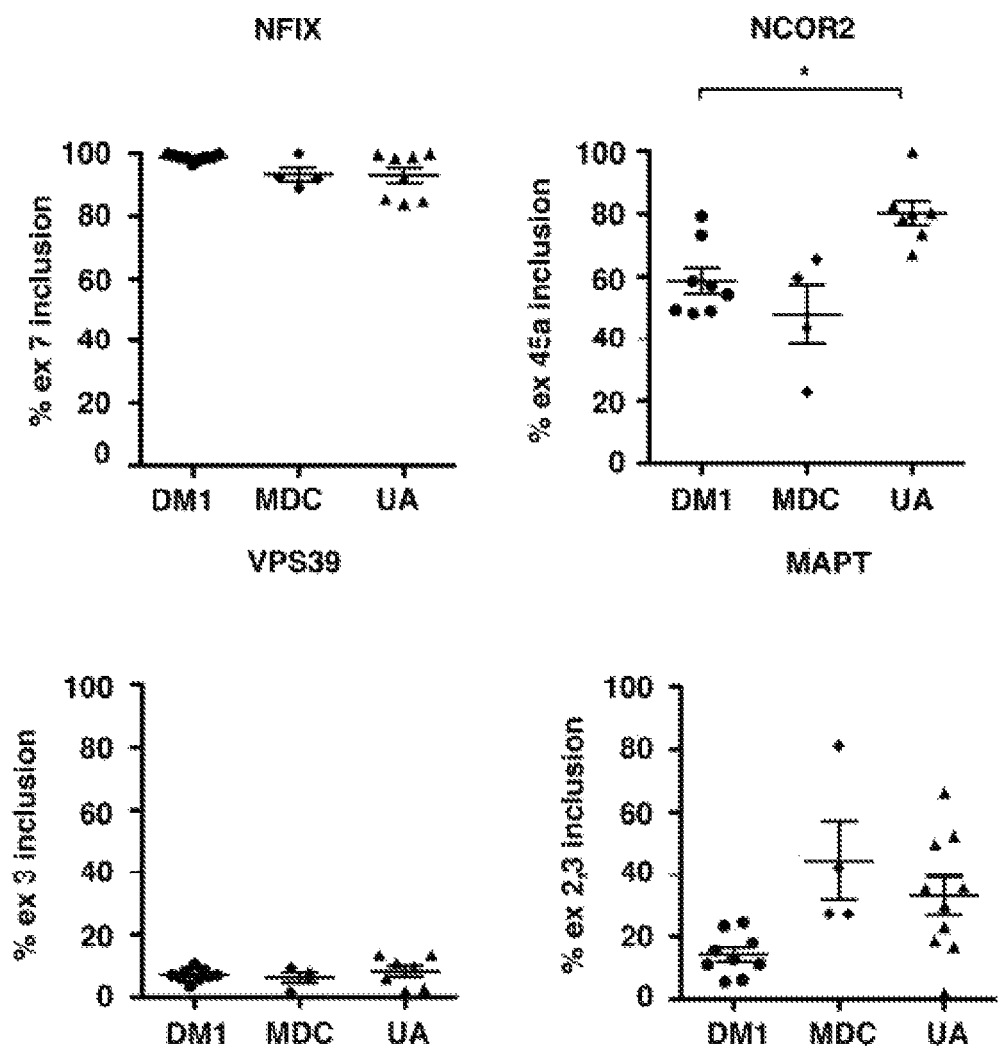
FIG. 10B, Cont'd

| | | % exon inclusion (unaffected tissue or urine) | | | | | |
|---|---|---|---|---|---|---|---|
| Transcript | Exon | Bladder | Urothelial | Kidney | Muscle | Urine ex-RNA (SEM) | Urine cell pellet (SEM) |
| MBNL1 | 7 | 8.7 | 47.3 | 53.8 | 20.0 | 48.3 (2.9) | 20.6 (2.5) |
| MBNL2 | 6 | 5.2 | 33.0 | 49.4 | 13.8 | 52.7 (1.3) | 54.9 (3.0) |
| MAP3K4 | 17 | 15.3 | 32.7 | 65.5 | 28.3 | 41.3 (1.2) | 39.5 (3.4) |
| MAPT | 2, 3 | 57.5 | 78.7 | 15.0 | 95.2 | 53.5 (3.0) | 33.7 (4.2) |
| NCOR2 | 45 | 25.2 | 89.4 | 81.2 | 10.6 | 75.7 (2.1) | 64.6 (3.0) |
| NFIX | 7 | 67.8 | 92.2 | 91.2 | 48.1 | 80.4 (1.8) | 94.6 (1.9) |
| CAPZB | 8 | 14.5 | 0.2 | 0.4 | 60.2 | <1 | n/d |
| PHKA1 | 19 | 77.5 | 94.1 | 95.7 | 27.4 | 95.5 (4.2) | n/d |
| BIN1 | 11 | 8.1 | 2.1 | 3.3 | 98.5 | 1.0 (0.4) | n/d |
| GFPT1 | 9 | 6.0 | 0.9 | 1.2 | 79.9 | <1 | n/d |
| DMD | 71 | 41.8 | 70.9 | 68.3 | 93.1 | 77.3 (3.8) | n/d |
| DMD | 78 | 86.8 | 5.4 | 15.1 | 97.3 | <1 | n/d |
*FIG. 11B*
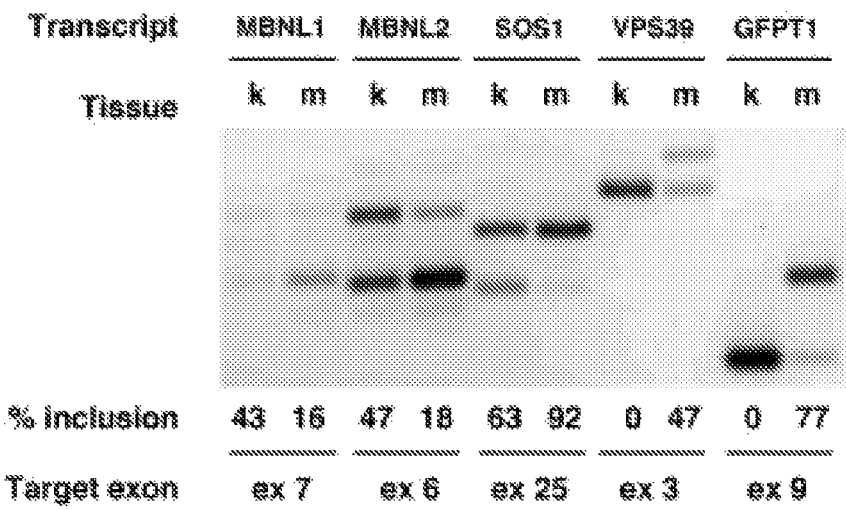
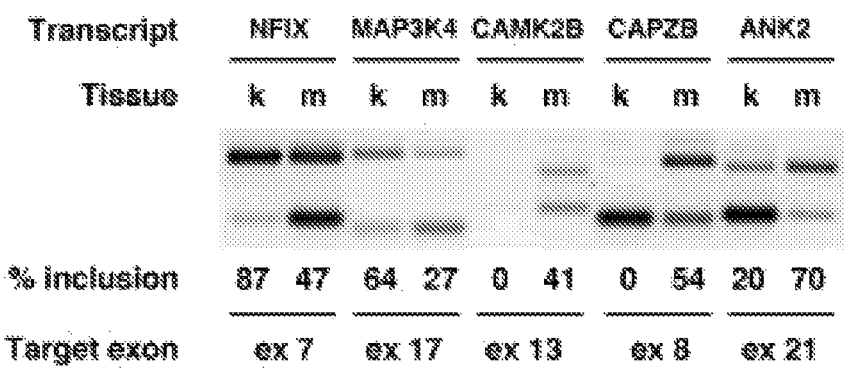
*FIG. 12A*

EXTRACELLULAR MRNA MARKERS OF MUSCULAR DYSTROPHIES IN HUMAN URINE

CLAIM OF PRIORITY

This application is a § 371 National Stage Application of PCT/US2017/043348, filed Jul. 21, 2017, which claims the benefit of U.S. Provisional Application Ser. No. 62/365,139, filed on Jul. 21, 2016. The entire contents of the foregoing are incorporated herein by reference.

FEDERALLY SPONSORED RESEARCH OR DEVELOPMENT

This invention was made with Government support under Grant No. CA069246 awarded by the National Institutes of Health. The Government has certain rights in the invention.

TECHNICAL FIELD

Described herein are methods for diagnosing and monitoring subjects with diseases associated with aberrant splicing, based upon detecting properly spliced isoforms and mis-spliced isoforms in a urine sample from the subject.

BACKGROUND

Pre-mRNA splicing occurs when introns are removed to generate a protein-coding message, while alternative splicing involves inclusion or exclusion of certain exons to code for different protein isoforms from the same gene. These splice variants are a fundamental process of nature designed to increase biodiversity, mainly in eukaryotes. Mis-regulation of pre-mRNA alternative splicing is found in a number of neurologic and neuromuscular diseases[1]. For example, in myotonic dystrophy type 1 (DM1) an expanded trinucleotide repeat in the 3' UTR of the DMPK transcript disrupts splicing regulator proteins in the muscleblind-like (MBNL) family, causing abnormal splicing of a number of pre-mRNAs[2,3].

SUMMARY

Urine contains extracellular RNA (exRNA) markers of urogenital cancers. However, the capacity of genetic material in urine to identify systemic diseases outside the urinary tract is unknown. In clinical trials for myotonic dystrophy type 1 (DM1) and Duchenne muscular dystrophy (DMD), non-invasive detection of mRNA splicing outcomes is needed to monitor therapeutic antisense oligonucleotide (ASO) drug effects. The present inventors examined whether ex-mRNA splice variants in human urine could meet sensitivity and specificity as robust markers of muscular dystrophies and other conditions associated with aberrant splicing, e.g., conditions associated with muscle weakness or dystrophy.

Ten transcripts were identified that are spliced differently in urine from DM1 patients as compared to unaffected individuals and disease controls. The predictive model was 100% accurate in our independent validation set. Urine also contains mutation-specific dystrophin deletion mRNAs amenable to therapeutic exon skipping ASO strategies in DMD patients, and a dystrophin cryptic splice site in a patient with Becker muscular dystrophy.

These results show that urine provides a renewable source of ex-mRNA splice variants that can serve as a powerful composite biomarker of DM1 or personalized genetic markers of DMD, suggesting its potential to monitor therapeutic response.

Thus, provided herein are methods that include obtaining a sample comprising urine from a subject who has, or is suspected to have, a disease associated with aberrant mRNA splicing; isolating extracellular mRNA in the sample; determining one or more selected mRNA in the sample, wherein the one or more selected mRNA is aberrantly spliced in the subject, and is suspected to be present in a plurality of spliced isoforms in the sample, wherein the spliced isoforms comprise properly spliced isoforms and mis-spliced isoforms; quantitating levels of the properly spliced isoforms and mis-spliced isoforms of the selected mRNA in the sample; and determining a ratio of the properly spliced isoforms to the mis-spliced isoforms in the sample.

Also provided are methods for diagnosing a disease associated with aberrant mRNA splicing. The methods include obtaining a sample comprising urine from a subject who has, or is suspected to have, a disease associated with aberrant mRNA splicing; isolating extracellular mRNA in the sample; determining one or more selected mRNA in the sample, wherein the one or more selected mRNA is aberrantly spliced in the subject, and is suspected to be present in a plurality of spliced isoforms in the sample, wherein the spliced isoforms comprise properly spliced isoforms and mis-spliced isoforms; quantitating levels of the properly spliced isoforms and mis-spliced isoforms of the one or more selected mRNAs in the sample; determining a ratio of the properly spliced isoforms to the mis-spliced isoforms of the one or more selected mRNAs in the sample; and comparing the ratio of properly spliced to mis-spliced in a subject to a reference ration, wherein a ratio in the subject that is less than the reference ratio indicates the presence of a disease associated with aberrant mRNA splicing.

In addition, provided herein are methods for monitoring the efficacy of a treatment for a disease associated with aberrant mRNA splicing in a subject. The methods include determining a first ratio of properly spliced isoforms to mis-spliced isoforms in a sample from the subject using a method described herein; administering a treatment for the disease to the subject; determining a subsequent ratio of properly spliced isoforms to mis-spliced isoforms in a sample from the subject using a method described herein; and comparing the first and subsequent ratios, wherein a ratio in the second sample that is higher than the ratio in the subsequent sample indicates that the treatment is effective.

In some embodiments, the treatment that is intended to correct splicing; to inhibit or reduce levels of mis-spliced transcripts; or to alter splicing to produce a functional protein. In some embodiments, the treatment is an antisense oligonucleotide.

In some embodiments, the disease is myotonic dystrophy type 1 (DM1); Duchenne muscular dystrophy (DMD); Becker muscular dystrophy (BMD); limb girdle muscular dystrophy type 1B (LGMD1B); LMNA-linked dilated cardiomyopathy (DCM); Hutchinson-Gilford progeria syndrome (HGPS); Familial partial lipodystrophy type 2 (FPLD2); spinal muscular atrophy (SMA); or amyotrophic lateral sclerosis (ALS).

In some embodiments, the disease is myotonic dystrophy type 1 (DM1), and wherein the one or more selected mRNAs is selected from the group consisting of the transcript for insulin receptor (INSR); muscleblind like splicing regulator 2 (MBNL2); SOS Ras/Rac guanine nucleotide exchange factor 1 (SOS1); cytoplasmic linker associated protein 1 (CLASP1); muscleblind like splicing regulator 1 (MBNL1);

mitogen-activated protein kinase kinase kinase 4 (MAP3K4); nuclear factor I X (NFIX); nuclear receptor corepressor 2 (NCOR2); VPS39, HOPS complex subunit (VPS39); and microtubule associated protein tau (MAPT).

In some embodiments, the selected mRNAs comprise MBNL2, MBNL1, SOS1, CLASP1, MAP3K4, and optionally INSR.

In some embodiments, the disease is associated with aberrant splicing of dystrophin (DMD); lamin A/C (LMNA); survival of motor neuron 2, centromeric (SMN2); solute carrier family 1 member 2 (SLC1A2); TAR DNA-binding protein (TARDP); or FUS RNA binding protein (FUS).

In some embodiments, one or more selected mRNAs is selected from the group consisting of the transcript for insulin receptor (INSR); muscleblind like splicing regulator 2 (MBNL2); SOS Ras/Rac guanine nucleotide exchange factor 1 (SOS1); cytoplasmic linker associated protein 1 (CLASP1); muscleblind like splicing regulator 1 (MBNL1); mitogen-activated protein kinase kinase kinase 4 (MAP3K4); nuclear factor I X (NFIX); nuclear receptor corepressor 2 (NCOR2); VPS39, HOPS complex subunit (VPS39); microtubule associated protein tau (MAPT); dystrophin (DMD); lamin A/C (LMNA); survival of motor neuron 2, centromeric (SMN2); solute carrier family 1 member 2 (SLC1A2); TAR DNA-binding protein (TARDP); and FUS RNA binding protein (FUS).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 6A-E. DMD genetic markers in urine exRNA. We used RT-PCR and DNA sequencing to examine urine exRNA from five DMD subjects with frame-shifting deletions of exons 18-22 (Subject 1; S1), exons 51-53 (S2), exons 45-52 (S3, S4), and exons 24-43 (S5). Deletions in S2, S3, and S4 are candidates for exon skipping antisense oligonucleotide drugs to restore the DMD reading frame. (A) Using RT-PCR, we detected DMD deletion mRNAs corresponding to the genetic mutation for all five subjects (S1-S5). The boxes show the exons amplified. "bp"=base pairs; "L"=DNA ladder. (B) DNA sequencing of extracted bands in a) identified the deletions for S1 and S2. (C) RT-PCR analysis of urine and serum exRNA from an unaffected subject appears similar to muscle tissue, while those from a subject with Becker muscular dystrophy (BMD) due to a t-to-g substitution in intron 67 identifies a second larger band. (D) DNA sequencing of the lower BMD bands showed normal splicing of exon 67/68, while the upper BMD band is a heteroduplex containing both the normally spliced DMD transcript and a $2^{nd}$ transcript that includes the $1^{st}$ five nucleotides of intron 67. (E) Diagram of the cryptic splice site in intron 67 that shifts the reading frame and produces a poorly functional dystrophin protein.

FIGS. 11A-B. RT-PCR analysis of alternative splicing in human and mouse kidney and skeletal muscle. (A) Urine EVs are derived from the kidney and urinary tract (Erdbrugger and Le, J Am Soc Nephrol 27, 12-26 (2016)), and splicing of transcripts derived from these tissues may explain the different splicing pattern of several transcripts in urine exRNA than in skeletal muscle (FIGS. 2A-C, 9A-B).

Figure 1A:
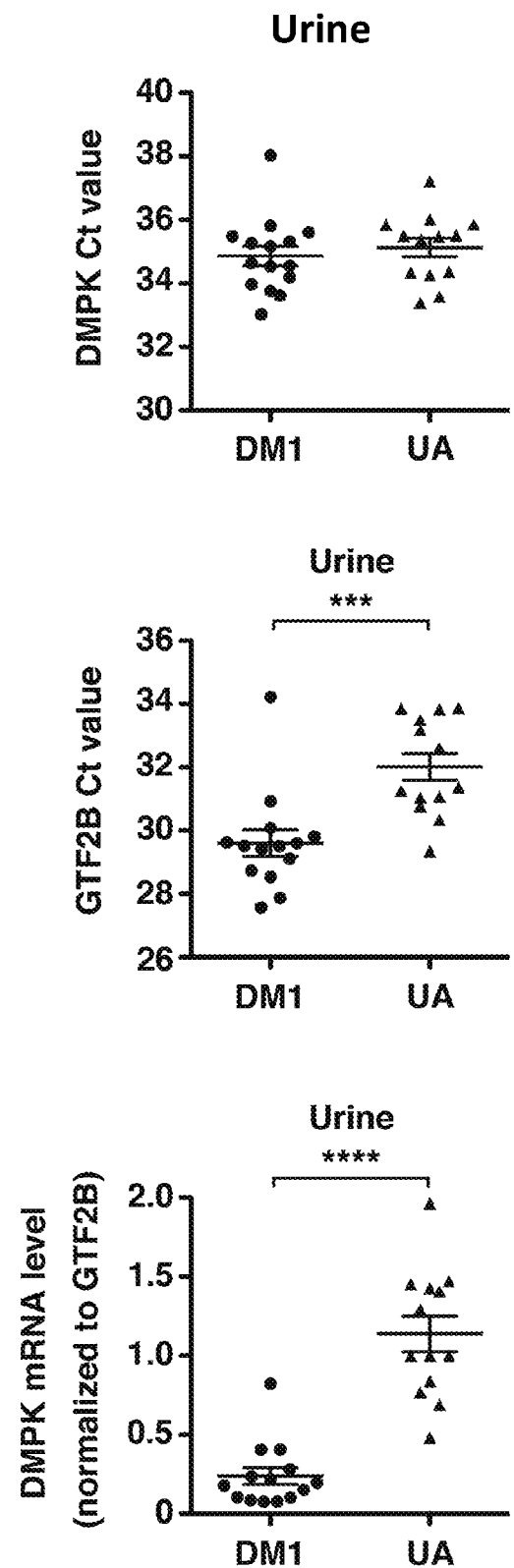
FIGS. 1A-B. Extracellular mRNA in human urine and serum. We isolated and examined extracellular RNA (exRNA) from urine (N=15 DM1 patients and 13 UA control subjects without muscular dystrophy) and serum (N=12 DM1 and 8 UA controls). (A) Expression of DMPK mRNA (upper) and GTF2B mRNA (middle) by qPCR as measured by cycle threshold (Ct) values, and DMPK expression normalized to GTF2B (lower) in human urine, and (B) in human serum. Individual data points represent the mean of duplicate assays for each sample. Error bars=mean±s.e.m. ** $P<0.0001$; * $P=0.0005$ (t-test).

To determine if the urinary tract may be the predominant source of urine exRNA, we screened alternative splicing of 12 splice events in commercially available mRNA from normal human bladder (B), urothelial (Ut; transitional epithelial) cells, kidney (K) and muscle (M) tissue by RT-PCR using random primers and 26 cycles for each transcript. (B) Percent exon inclusion of each transcript shown in (A) and mean percent exon inclusion±standard error of the mean (SEM) of urine ex-RNA and urine cell pellets (FIGS. 2A-C, 9A-B, 10A-B). "n/d"=not done.

FIGS. 12A-D. We examined splicing of 6 alternatively spliced transcripts by RT-PCR in bladder (N=3), kidney (N=2), and muscle tissue (N=2) from FVB wild-type mice and muscle tissue from the HSA$^{LR}$ transgenic mouse model of DM1 (N=2) using oligo dT and 26 cycles for each transcript. Transcript name is shown on the left and target exon on the right. The percent exon inclusion is indicated below each lane. (A) Urine EVs are derived from the kidney and urinary tract (6), and splicing of transcripts derived from these tissues may explain the different splicing pattern of several transcripts in urine exRNA than in skeletal muscle (FIG. 2, S7). To determine if the kidney may be the predominant source of urine exRNA, we screened alternative splicing of 10 transcripts in commercially available mRNA from normal human kidney (k) and muscle (m) tissue (Ambion) by RT-PCR using random primers and 26 cycles for each transcript. (B) We examined splicing of 6 alternatively spliced transcripts by RT-PCR in bladder (N=3), kidney (N=2), and muscle tissue (N=2) from FVB wild-type mice and muscle tissue from the HSA$^{LR}$ transgenic mouse model of DM1 (N=2) using oligo dT and 26 cycles for each transcript. Transcript name is shown on the left and target exon on the right. The percent exon inclusion is indicated below each lane. (C) We used qPCR to analyze expression of genes DMPK, GTF2B, GAPDH, and CKM in mRNA derived from human kidney and muscle tissue. (Upper) the mean qPCR cycle threshold (Ct) of duplicate assays for each gene is shown. (Lower) DMPK expression mRNA expression level normalized to reference genes GTF2B (left) and GAPDH (right). Expression of DMPK in kidney tissue indicates kidney is a potential source of these transcripts in urine exRNA. (D) DMD transcripts expressed in human kidney (k) and muscle (m) tissue using RT-PCR. "E"=empty lane; "Lad"=DNA ladder; "NT"=nucleotides.

DETAILED DESCRIPTION

In DM1 patients, pre-mRNA splicing outcomes in muscle biopsies are biomarkers of disease severity[4], while in DM1 mice they serve as sensitive indicators of therapeutic drug effects[5,6]. Less invasive biomarkers to assess disease state and response to therapy in DM are currently unavailable, and optimal outcome measures of therapeutic success remain undefined. As a result, a recent clinical trial of an antisense oligonucleotide (ASO) drug for DM1 required participants' consent to multiple muscle biopsies to monitor splicing outcomes in response to therapy and was restricted to adult patients[7]. This experimental drug for DM1 is designed to induce knockdown through the RNase H pathway of mutant transcripts, thereby rescuing muscle cells from the pathogenic effects of splicing mis-regulation[6,8].

Extracellular vesicles (EVs) include exosomes, microvesicles, and other membrane-encased nanoparticles released and taken up by cells as a form of extracellular communication. EVs in serum and urine contain mRNA and non-coding RNAs, including microRNA (miRNA), termed exRNAs, released from different tissues and can serve as genetic biomarkers of cancers and other disease states[10-12]. Mutations, deletions, translocations, and transcriptome variations also have been shown extensively in EVs, especially for cancers[13-15]. Differentiated skeletal muscle cells in culture release EVs[16,17] and a handful of miRNA biomarkers and several protein signatures have been identified in serum of muscular dystrophy patients[18]. However, the capacity of muscle-derived exRNA in urine to serve as biomarkers for muscular dystrophies seems unlikely given that they would be released into the blood circulation and would be unable to pass through the glomerular filtration of serum in the kidney[19]. The present results demonstrate that RNA splice products in human urine have sufficient sensitivity and specificity to be robust biomarkers of muscular dystrophies.

As shown herein, mRNA splicing patterns in "liquid biopsies" present a rich source of personalized biomarkers with applications to a number of genetic diseases. For DM1, we found 10 alternative splice variants in urine that serve as a robust composite biomarker of DM1 disease activity. Mis-regulated alternative splicing outcomes in muscle tissue were sensitive indicators of therapeutic response in DM1 mice[5,6] and disease activity in DM1 patients[4]. Indeed, splice products in muscle biopsies were used in a recent clinical trial as measures of ASO activity in DM1 patients[7]. The present methods using splicing outcomes provides powerful biomarkers of DM1, in part because the disease mechanism involves mis-regulated alternative splicing; in addition, the ratiometric measurements of exon inclusion/exclusion described herein are inherently more sensitive than the unidirectional changes that are typical of most biomarkers.

The detection of differential splicing in urine and not in serum was surprising, and suggests that the source of exRNA in these biofluids may be different and that the primary source in serum is unlikely to be muscle tissue. Because DM1 is primarily a disease of skeletal muscle, heart, and the central nervous system (CNS), it is counter-intuitive that exRNA reflecting the characteristic mis-regulated splicing events appears in urine rather than in blood, as exRNA has not been shown to pass from the blood through the proximal tubules of the kidney[29]. In earlier pre-clinical studies, therapeutic ASOs induced target knockdown and exon skipping in kidney tissue of mice and non-human primates[8,30], suggesting ASOs could have similar effects in human kidney and other tissues lining the urinary tract that release exRNA into the urine. The potential to evaluate exRNA splicing outcomes as pharmacodynamic biomarkers in urine has the advantage of being non-invasive and can be repeated routinely over the course of treatment to evaluate efficacy. For example, due to the need for general anesthesia and the absence of a therapeutic benefit, muscle biopsies generally are avoided in children with DM1. Consequently, detailed study of splicing outcomes in children with DM1 remains an unmet medical need. Urine exRNA should enable comprehensive non-invasive investigation of splicing outcomes in children with DM for the first time, facilitate clinical trials to these patients earlier, and enable convenient titration of dose. The shared pathogenic mechanism of alternative splicing misregulation in DM1 and DM2[4] suggests urine exRNA also may be useful for monitoring disease activity in DM2 patients.

For DMD, the urine splice products are more than traditional biomarkers: they are personalized genetic markers that are designed specifically for each individual patient and enable the possibility to monitor splice-shifting ASO drug effects[27,28]. Dystrophin protein measurement in biopsy tissue is presently used as a surrogate marker of drug effect that led to the accelerated approval of eteplirsen by the U.S.

Food and Drug Administration[31]. However, monitoring the ratio of skipped/unskipped DMD splice products in urine during the course of treatment may be used to complement RT-PCR analysis of muscle biopsies and/or in place of dystrophin protein measurement as a surrogate marker of therapeutic effect as newer and better splice-shifting drugs are developed.

The finding of a DMD cryptic splice site responsible for Becker MD phenotype in an individual with dystrophinopathy further suggests the value of liquid biopsies as a means to identify novel splice variants that may help correlate genotype with phenotype for a number of diseases for which non-invasive biomarkers are unavailable. For example, in patients with Hutchinson-Gilford progeria syndrome (HGPS), point mutations in the LMNA gene activate a weak splice site in exon 11 that shortens the transcript and produces a truncated progerin protein[32]. ASOs that reduce use of this weak splice site are being evaluated as strategy to treat HGPS[33]. The presence of LMNA exon 11 in urine (FIG. 9B) shows that the present methods including use of exRNA can be used to monitor drug effects in these patients as well. The present findings also support development of exRNA from urine, serum, or CSF as a biomarker replacement for tissue biopsies in other diseases with altered mRNA splicing, including limb girdle muscular dystrophy type 1B, spinal muscular atrophy and amyotrophic lateral sclerosis[34-36].

Table A provides a list of exemplary conditions that can be diagnosed, treated, or monitored using the present methods, along with the mutated genes (though note that the mutation may or may not result in altered splicing of that specific gene, or not only that specific gene).

TABLE A

Diseases associated with aberrant mRNA splicing

| Disease | Mutated Gene | NCBI RefSeq ID |
|---|---|---|
| Myotonic dystrophy type 1 (DM1) | dystrophia myotonica protein kinase gene (DMPK) | NM_004409.4 |
| Duchenne muscular dystrophy (DMD) | dystrophin (DMD), transcript variant Dp427m | NM_004006.2 |
| Becker muscular dystrophy (BMD) | dystrophin (DMD), transcript variant Dp427m | NM_004006.2 |
| Limb girdle muscular dystrophy type 1B (LGMD1B) | lamin A/C (LMNA), isoform A | NM_170707.3 |
| LMNA-linked dilated cardiomyopathy (DCM) | | |
| Hutchinson-Gilford progeria syndrome (HGPS) | | |
| Familial partial lipodystrophy type 2 (FPLD2) | | |
| Spinal muscular atrophy (SMA) | survival of motor neuron 2, centromeric (SMN2) | NG_008728.1 |
| Amyotrophic lateral sclerosis (ALS) | solute carrier family 1 member 2 (SLC1A2 aka EAAT2) | NM_004171.3 |
| | TAR DNA-binding protein (TARDP) | NM_007375.3 |
| | FUS RNA binding protein (FUS) | NM_004960.3 |

Additional diseases are known in the art, including limb-girdle muscular dystrophy type 2B, Miyoshi myopathy, distal myopathy with anterior tibial onset and Fukuyama congenital muscular dystrophy, see, e.g., Scotti and Swanson, Nature Reviews Genetics 17:19-32 (2016), and Touznik et al., Expert Opin Biol Ther. 2014 June; 14(6):809-19.

Myotonic Dystrophy Type 1 (DM1)

DM1 is caused by a heterozygous trinucleotide repeat expansion (CTG)n in the 3-prime untranslated region of the dystrophia myotonica protein kinase gene (DMPK); a repeat length exceeding 50 CTG repeats is pathogenic (Musova et al., Am. J. Med. Genet. 149A: 1365-1374, 2009). The CUG repeats form RNA hairpins that bind proteins including muscleblind-like 1 (MBNL1), a splicing regulatory factor; nuclear sequestration of MBNL1 prevents its activity and results in aberrant splicing of several genes. As shown herein, a number of pre-mRNAs are aberrantly spliced in urine (see Tables 5 and 6); of those, the following showed differential urine exRNA splicing in DM1 vs MDC and UA controls:

| Gene | Gene Name | NCBI Ref SEQ |
|---|---|---|
| INSR | Homo sapiens insulin receptor (INSR), transcript variant 1, mRNA | NM_000208.3 |
| MBNL2 | Homo sapiens muscleblind like splicing regulator 2 (MBNL2), transcript variant 1, mRNA | NM_144778.3 |
| SOS1 | Homo sapiens SOS Ras/Rac guanine nucleotide exchange factor 1 (SOS1), mRNA | NM_005633.3 |
| CLASP1 | Homo sapiens cytoplasmic linker associated protein 1 (CLASP1), transcript variant 1, mRNA | NM_015282.2 |
| MBNL1 | Homo sapiens muscleblind like splicing regulator 1 (MBNL1), transcript variant 1, mRNA | NM_021038.4 |
| MAP3K4 | Homo sapiens mitogen-activated protein kinase kinase kinase 4 (MAP3K4), transcript variant 1, mRNA | NM_005922.3 |
| NFIX | Homo sapiens nuclear factor I X (NFIX), transcript variant 2. mRNA | NM_002501.3 |
| NCOR2 | Homo sapiens nuclear receptor corepressor 2 (NCOR2), transcript variant 1, mRNA | NM_006312.5 |
| VPS39 | Homo sapiens VPS39, HOPS complex subunit (VPS39), transcript variant 2, mRNA | NM_015289.3 |
| MAPT | Homo sapiens microtubule associated protein tau (MAPT), transcript variant 1, mRNA | NM_016835.4 |

The methods can include determining ratios of properly spliced mRNA to aberrantly spliced mRNA for all or a subset, e.g., 1, 2, 3, 4, 5, 6, 7, 8, 9 or all 10 of the above. In some embodiments, the subset includes 1, 2, 3, 4, or all of MBNL2, MBNL1, SOS1, CLASP1, MAP3K4, and optionally also INSR.

DM1 affects skeletal and smooth muscle as well as the eye, heart, endocrine system, and central nervous system. Symptoms can include muscle weakness, e.g., in the leg, hand, neck, and/or face; myotonia, e.g., grip myotonia or percussion myotonia; and posterior subcapsular cataracts (which are detectable as red and green iridescent opacities on slit lamp examination).

The methods described herein can also include administering a treatment for DM1, e.g., a treatment that is expected or intended to affect splicing, e.g., to correct splicing or to inhibit or reduce levels of aberrantly spliced transcripts, e.g., as described herein. The present methods can be used to monitor efficacy, e.g., to determine whether the treatment affects splicing, e.g., by detecting a change in the ratio of properly spliced mRNA to aberrantly spliced mRNA. An increase in the properly spliced mRNA, and/or a decrease in aberrantly spliced mRNA, would result in an increase in the ratio and indicates that the treatment is effective.

Duchenne Muscular Dystrophy (DMD) and Becker Muscular Dystrophy (BMD)

DMD and BMD are inherited progressive muscle disorders that are noninflammatory and not associated with a central or peripheral nerve abnormality. The disease affects the muscles with definite fiber degeneration but without evidence of morphologic aberrations, resulting in progressive muscle wasting, and are caused by defects in the dystrophin gene DMD. See, e.g., Aartsma-Rus et al., J Med Genet. 2016 March; 53(3):145-51; Flanigan et al., Hum Mutat. 2011 March; 32(3): 299-308. In some cases, DMD or BMD are caused by mutations that affect splicing of the transcript, e.g., acceptor or donor splice site mutations. The present methods can be used to detect these alternative mRNA splice variants or mRNA of different lengths. The methods can include determining ratios of properly spliced DMD mRNA to aberrantly spliced DMD mRNA.

The methods described herein can also include administering a treatment for DMD or BMD, e.g., a treatment that is expected or intended to affect splicing, e.g., to correct splicing of the dystrophin transcripts, reduce levels of aberrant transcripts, or to produce transcripts that encode functional dystrophin protein. In general, ASOs for DMD are used to induce new splicing changes that serve to restore the open reading frame rather than correct aberrant splicing. It may be possible that some DMD mutations that lead to a Duchenne phenotype and that ASOs could be designed to treat this. Alternative splicing of DMD transcripts typically includes exon 71, 78, and perhaps exon 68. The remainder of the DMD exons are spliced constitutively. Urine RNA can also be used to identify novel aberrant splicing, as in our Becker patient with a cryptic splice site.

The present methods can be used to monitor efficacy, e.g., to determine whether the treatment affects splicing, e.g., by detecting a change in the ratio of properly spliced mRNA (or mRNA of a desired size or sequence) to aberrantly spliced mRNA (or mRNA of a non-desired size or sequence). An increase in the properly spliced mRNA or mRNA of a desired size or sequence, and/or a decrease in aberrantly spliced mRNA or mRNA of a non-desired size or sequence, would result in an increase in the ratio and indicates that the treatment is effective.

Limb Girdle Muscular Dystrophy Type 1B/Hutchinson-Gilford Progeria Syndrome (HGPS)/LMNA-Linked Dilated Cardiomyopathy (DCM)/Familial Partial Lipodystrophy Type 2 (FPLD2)

Mutations in the lamin A (LMNA) gene that result in aberrant splicing are associated with a number of hereditary disorders. See Scotti and Swanson, Nature Reviews Genetics 17:19-32 (2016).

Hutchinson-Gilford progeria syndrome (HGPS) is caused by mutations within the LMNA gene that lead to increased usage of an internal splice site, resulting in alternative lamin A transcript with internal deletions of 150 nucleotides (LMNA G608G (GGC>GGT) mutation); see Eriksson et al., Nature 423, 293-298 (2003); Rodriguez et al., Eur J Hum Genet. 2009 July; 17(7): 928-937.

Limb-girdle muscular dystrophies (LGMD) are a heterogeneous group of muscle disorders; symptoms begin in the voluntary muscles of the hips and shoulders. See Nigro and Saverese, Acta Myol. 2014 May; 33(1):1-12.

In familial partial lipodystrophy type 2 (FPLD2), a G>C mutation leads to aberrant intron 8 retention, nonsense-mediated decay and may lead to translation of a truncated lamin A/C. see Scotti and Swanson, Nature Reviews Genetics 17:19-32 (2016)).

LMNA-linked dilated cardiomyopathy (DCM) is associated with an alternative 3' splice site generated by an A>G mutation (c. 640-10A>G); see Scotti and Swanson, Nature Reviews Genetics 17:19-32 (2016)).

The methods described herein can also include administering a treatment for a conditions associated with mis-splicing of LMNA, e.g., a treatment that is expected or intended to affect splicing, e.g., to correct splicing of the dystrophin transcripts, reduce levels of aberrant transcripts, or to produce transcripts that encode functional dystrophin protein. The present methods can be used to monitor efficacy, e.g., to determine whether the treatment affects splicing, e.g., by detecting a change in the ratio of properly spliced mRNA (or mRNA of a desired size or sequence) to aberrantly spliced mRNA (or mRNA of a non-desired size or sequence). An increase in the properly spliced mRNA or mRNA of a desired size or sequence, and/or a decrease in aberrantly spliced mRNA or mRNA of a non-desired size or sequence, would result in an increase in the ratio and indicates that the treatment is effective.

Spinal Muscular Atrophy

SMA is associated with mutations in the SMN1 gene (including c.922+6 T/G deletion) and loss of SMN full-length protein; see Lorson et al., Proc. Natl Acad. Sci. USA 96, 6307-6311 (1999); Lefebvre et al., Cell 80, 155-165 (1995); Scotti and Swanson, Nature Reviews Genetics 17:19-32 (2016)). Approximately 98% of spinal muscular atrophy (SMA) patients have a survival of motor neurons (SMN) gene that has been deleted or mutated. SMN is part of a large multi-protein complex (with additional proteins, including Gemeins 2-7) that is necessary for biogenesis of small nuclear RNA ribonucleoproteins (snRNPs), which are major components of pre-mRNA splicing machinery. Genetic alterations in the SMN gene result in the reduced capacity for snRNP assembly, and defects in RNA splicing. See Dreyfuss, Eukaryon, 6:75-79, 2010, herein incorporated by reference in its entirety.

The methods described herein can also include administering a treatment for SMA, e.g., a treatment that is expected or intended to affect splicing, e.g., to correct splicing of the dystrophin transcripts, reduce levels of aberrant transcripts, or to produce transcripts that encode functional dystrophin protein. Splicing of SMN2 normally involves skipping of exon 7 in the majority of SMN2 transcripts. ASO treatment of SMA involves increasing inclusion of SMN2 exon 7, which results in an increase of SMN protein levels, the same protein that is lost by mutations in SMN1. The present methods can be used to monitor efficacy, e.g., to determine whether the treatment affects splicing, e.g., by detecting a change in the ratio of properly spliced mRNA (or mRNA of a desired size or sequence) to aberrantly spliced mRNA (or mRNA of a non-desired size or sequence). An increase in the properly spliced mRNA or mRNA of a desired size or sequence, and/or a decrease in aberrantly spliced mRNA or mRNA of a non-desired size or sequence, would result in an increase in the ratio and indicates that the treatment is effective.

Amyotrophic Lateral Sclerosis

Approximately 60%-70% of patients with sporadic Amyotrophic lateral sclerosis (ALS) display a loss of the astrocytic glutamate transporter protein EAAT2 (also known as SLC1A2) in motor cortex and spinal cord. See Rothstein et al., Ann. Neurol. 38:73-84, 1995, herein incorporated by reference in its entirety. Defective pre-mRNA splicing in the motor cortex and spinal cord is responsible for the loss of EAAT2 protein. This defective splicing is caused by a defect in a splicing regulatory factor, rather than a mutation in the EAAT2 gene that causes alternative aberrant splicing or a defect in a general splicing apparatus, such as the spliceosome. The defective pre-mRNA splicing process for EAAT2 can skip normal 5' and 3' splice sites (donor and acceptor splicing sites), or use inappropriate 5' and 3' splice sites (i.e., other than the normal GU or AU for the donor site, and AG or AC for the acceptor site), resulting in multiple abnormal RNAs in ALS patients. The aberrant splicing results in transcripts that partially retain introns or skip exons, as well as transcripts that have exonic sequences at random sites. Two aberrantly spliced EAAT2 mRNAs are found predominantly in sporadic ALS patients. These include an mRNA transcript that partially retains intron 7 and an mRNA transcript that skips exon 9 of the gene. The intro 7-retaining RNA causes a dominant-negative effect on normal EAAT2 that has been shown to result in a loss of protein and activity. See, e.g., Honig et al., Neurology. 2000 Oct. 24; 55(8):1082-8; Lin et al., Neuron. 1998 March; 20(3):589-602; Meyer et al., J Neurol Sci. 1999 Nov. 15; 170(1):45-50. Certain forms of ALS are associated with the presence of mutations in the TARDP (c. 991C>A), (c.1009A>G) and FUS (c. 1566C>T), (c. 1561T>G) genes; see Scotti and Swanson, Nature Reviews Genetics 17:19-32 (2016)); Bai and Lipton, 20(3):363-366 (1998); Zhou et al., PLoS Genet. 2013 October; 9(10):e1003895; Orozco and Edbauer, J Mol Med (Berl). 2013 December; 91(12):1343-54; Belzil et al., J Mol Med (Berl). 2013 December; 91(12): 1343-54.

The methods described herein can also include administering a treatment for conditions associated with mis-splicing of SLC1A2, TARDP, or FUS, e.g., a treatment that is expected or intended to affect splicing, e.g., to correct splicing of the dystrophin transcripts, reduce levels of aberrant transcripts, or to produce transcripts that encode functional dystrophin protein. The present methods can be used to monitor efficacy, e.g., to determine whether the treatment affects splicing, e.g., by detecting a change in the ratio of properly spliced mRNA (or mRNA of a desired size or sequence) to aberrantly spliced mRNA (or mRNA of a non-desired size or sequence). An increase in the properly spliced mRNA or mRNA of a desired size or sequence, and/or a decrease in aberrantly spliced mRNA or mRNA of a non-desired size or sequence, would result in an increase in the ratio and indicates that the treatment is effective.

Methods of Diagnosis and Monitoring

Included herein are methods for diagnosing and monitoring subjects with a disease associated with a genetic mutation that results in aberrant splicing, e.g., myotonic dystrophy type 1 (DM1), Duchenne muscular dystrophy (DMD), Becker muscular dystrophy (BMD), limb girdle muscular dystrophy type 1B (LGMD1B), LMNA-linked dilated cardiomyopathy (DCM); Hutchinson-Gilford progeria syndrome (HGPS); Familial partial lipodystrophy type 2 (FPLD2), spinal muscular atrophy (SMA) and amyotrophic lateral sclerosis (ALS). The methods can also be used to diagnose and monitor subjects with other splicing diseases, e.g., progeria.

The methods rely on detection of ratios of properly spliced (which can include transcripts that are spliced by an ASO) to mis-spliced isoforms of affected transcripts in urine samples. As used herein, "properly spliced" means that the transcript has a desired splice pattern, e.g., has wild-type splicing, or is spliced in a way that is desired, e.g., to produce a functional protein. For example, in some embodiments, the DMD exons targeted by ASOs are constitutively spliced, meaning they are always included in DMD patients and UA individuals. Treatment with ASOs in DMD is designed to induce a new unique splice event absent in DMD patients or UA individuals, and the ratio of the inclusion of the unique splice site (properly spliced) to inclusion of the constitutive splice (mis-spliced) provides a convenient estimation of ASO drug effects in urine a new unique splice event absent in DMD patients or UA individuals; in this case, a transcript that was "properly spliced" in a subject with DMD being treated with these ASOs would include the unique splice event. The methods can include determining that the mRNA is of a desired size or sequence (i.e., "properly spliced"), or is of a non-desired size or sequence ("mis-spliced").

The methods include obtaining a urine sample from a subject determining levels of properly spliced and aberrantly spliced extracellular transcripts, and determining a ratio of properly spliced to mis-spliced transcript in the sample. The methods can include comparing the ratio with one or more reference ratios, e.g., a control reference that represents a normal ratio of properly spliced:mis-spliced transcript, e.g., a level in an unaffected subject, and/or a disease reference that represents a ratio associated with the disease. For example, in some embodiments a reference ratio of properly spliced:mis-spliced transcripts in an unaffected subject may approach 1:0, since there would not be expected to be a large number of mis-spliced transcripts in such individuals.

Various methods are well known within the art for determining levels of properly spliced and aberrantly spliced extracellular transcripts. These methods can include identification and/or isolation and/or purification of a transcript from a sample. An "isolated" or "purified" biological marker is substantially free of cellular material or other contaminants from the cell or tissue source from which the biological marker is derived i.e. partially or completely altered or removed from the natural state through human intervention. For example, nucleic acids contained in the sample can be isolated according to standard methods, for example using filtration, centrifugation, or other methods of purification to obtain a sample that contains extracellular transcripts but does not contain cells or cellular transcripts. The methods can include using chemical solutions nucleic acid-binding resins following the manufacturer's instructions. In one example, the entire volume of urine is centrifuged, e.g., at 2,000-3,000×g, e.g., at 2,450×g for 5-15 minutes, e.g., 10 minutes at room temperature, and then the supernatant is passed through a filter, e.g., a 0.8 µm filter, before being ultracentrifuged, e.g., at 100,000×g 2 hours at 4° C., to pellet the RNA. Then the supernatant is removed and, RNA is extracted from the translucent ribonucleoprotein pellet, e.g., using Trizol (Life Technologies) according to manufacturer instructions. To enhance RNA pellet visibility, linear acrylamide (Ambion) or other reagents can be added.

The transcripts can be evaluated using methods known in the art, e.g., using polymerase chain reaction (PCR), reverse transcriptase polymerase chain reaction (RT-PCR), quantitative or semi-quantitative real-time RT-PCR, digital PCR i.e. BEAMing ((Beads, Emulsion, Amplification, Magnetics) Diehl (2006) Nat Methods 3:551-559); RNAse protection assay; Northern blot; various types of nucleic acid sequencing (Sanger, pyrosequencing, NextGeneration Sequencing); fluorescent in-situ hybridization (FISH); or gene array/chips) (Lehninger Biochemistry (Worth Publishers, Inc., current addition; Sambrook, et al, Molecular Cloning: A Laboratory Manual (3. Sup.rd Edition, 2001); Bernard (2002) Clin Chem 48(8): 1178-1185; Miranda (2010) Kidney International 78:191-199; Bianchi (2011) EMBO Mol Med 3:495-503; Taylor (2013) Front. Genet. 4:142; Yang (2014) PLOS One 9(11):e110641); Nordstrom (2000)

Biotechnol. Appl. Biochem. 31(2):107-112; Ahmadian (2000) Anal Biochem 280:103-110. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289 (5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of different splice isoforms. multiple-exon-skipping detection assay (MESDA) can also be used (see Singh et al., 2012, PLoS One. 2012; 7(11):e49595). Measurement of the level of different splice isoforms can be direct or indirect. For example, the abundance levels of various differently spliced isoforms can be directly quantitated, e.g., based on size or the presence or absence of a selected sequence. In some embodiments a technique suitable for the detection of alterations in the structure or sequence of nucleic acids, such as the presence of deletions, amplifications, or substitutions, can be used for the detection of different splice isoforms.

Gene arrays are prepared by selecting probes which comprise a polynucleotide sequence, and then immobilizing such probes to a solid support or surface. For example, the probes may comprise DNA sequences, RNA sequences, co-polymer sequences of DNA and RNA, DNA and/or RNA analogues, or combinations thereof, which detect various spliced isoforms. The probe sequences can be synthesized either enzymatically in vivo, enzymatically in vitro (e.g. by PCR), or non-enzymatically in vitro.

In some embodiments, the methods can be used to diagnose a condition described herein; for example, when the ratio of properly spliced:mis-spliced transcripts in a subject (e.g., a subject who has one or more symptoms associated with the disease) is comparable to a reference ratio in a representative subject with the disease, then the subject can be diagnosed with the disease. In some embodiments, once it has been determined that a person has a disease described herein, e.g., DM1, DMD, BMD, LGMD1B, SMA, or ALS, then a treatment, e.g., as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful ratio, e.g., a control reference level that represents a normal level ratio, e.g., a level in an unaffected subject, and/or a disease reference that represents a ratio associated with the disease, e.g., a level in a subject having a disease as described herein, e.g., DMD, DM1, BMD, LGMD, HGPS, DCM, HGPS, FPLD2, SMA, or ALS.

The predetermined ratio can be a single cut-off (threshold) value, such as a median or mean, or a ratio that defines the boundaries of an upper or lower quartile, tertile, or other segment of a clinical trial population that is determined to be statistically different from the other segments. It can be a range of cut-off (or threshold) ratios, such as a confidence interval. It can be established based upon comparative groups, such as where association with presence of disease in one defined group is a fold higher, or lower, (e.g., approximately 2-fold, 4-fold, 8-fold, 16-fold or more) than the presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined ratio is a ratio in the same subject, e.g., at a different time point, e.g., an earlier time point.

Subjects associated with predetermined values are typically referred to as reference subjects. For example, in some embodiments, a control reference subject does not have a disorder described herein (e.g., DMD, DM1, BMD, LGMD, HGPS, DCM, HGPS, FPLD2, SMA, and ALS). In some cases it may be desirable that the control subject is a first or second degree relative of the subject to be tested.

A disease reference subject is one who has (has been diagnosed with) a disease as described herein, e.g., DMD, DM1, BMD, LGMD, HGPS, DCM, HGPS, FPLD2, SMA, or ALS.

Thus, in some cases the ratio of properly spliced:mis-spliced in a subject being less than a reference ratio is indicative of a clinical status (e.g., indicative of presence of a disorder as described herein, e.g., DMD, DM1, BMD, LGMD, HGPS, DCM, HGPS, FPLD2, SMA, or ALS), or indicative of an ineffective therapy. In other cases the ratio in a subject being greater than or equal to the reference ratio is indicative of the absence of disease, or an effective therapy. In some embodiments, the amount by which the ratio in the subject is the less than the reference ratio is sufficient to distinguish a subject from a control subject, and optionally is a statistically significantly less than the ratio in a control subject. In cases where the ratio in a subject being equal to the reference ratio, the "being equal" refers to being approximately equal (e.g., not statistically different).

The predetermined ratio can depend upon the particular population of subjects (e.g., human subjects) selected. For example, an apparently healthy population may have a different 'normal' range of ratios than will a population of subjects which have, are likely to have, or are at greater risk to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

Methods of Treatment

The methods described herein can include administering a treatment of disorders associated with aberrant splicing. In some embodiments, the disorder is DMD, DM1, BMD, LGMD, HGPS, DCM, HGPS, FPLD2, SMA, or ALS. Generally, the methods include administering a treatment to a subject identified using a method described herein.

As used in this context, to "treat" means to ameliorate at least one symptom of the disorder associated with aberrant splicing. For example, where the disease is a muscular dystrophy, a treatment can result in a reduction in muscle weakness or a reduction in rate of muscle loss or weakening.

Exon-skipping antisense oligonucleotides (ASOs) that correct missplicing can be used, e.g., as described in Siva et al., Nucleic Acid Ther. 2014 Feb. 1; 24(1): 69-86; Scotti and Swanson, Nature Reviews Genetics 17:19-32 (2016). For example, bicyclic-locked nucleic acids (LNAs), ethylene-bridged nucleic acids (ENAs), 2'-O-methyl phosphorothioate AO (2OME-PSs), peptide nucleic acids (PNAs), or phosphorodiamidate morpholino oligomers (PMOs) have been described that correct missplicing in clinical trials and animal models; see, e.g., Brolin and Shiraishi, Artif DNA PNA XNA. 2011 January-March; 2(1): 6-15; Scotti and Swanson, Nature Reviews Genetics 17:19-32 (2016); Touznik et al., Expert Opin Biol Ther. 2014 June; 14(6): 809-19. The ASOs can be delivered, e.g., parenterally in liposomal complexes, e.g., cationic lipoplexes, or using a viral vector, e.g., a lentivirus, adenovirus, or adeno-associated virus. See e.g., Jarver et al., Nucleic Acid Ther. 2014; 24(1):37-47; Aartsma-Rus et al., Hum Gene Ther. 2014; 25(10):885-892, McNally and Wyatt, J Clin Invest. 2016 Apr. 1; 126(4):1236-8; Imbert et al., Genes 2017, 8(2), 51; doi:10.3390/genes8020051.

Exon skipping uses antisense oligonucleotides (ASOs) to alter transcript splicing; the present methods can be used to detect these transcripts with desired splicing. These treatments can include antisense oligonucleotide-targeted exon skipping to induce near normal, e.g., for dystrophin, e.g., as described in Aartsma-Rus, Methods Mol Biol. 2012; 867: 97-116. Clinical trials of ASOs in DMD have been conducted, see, e.g., Koo and Wood, Hum Gene Ther. 2013 May; 24(5):479-88; Voit et al., Lancet Neurol. 2014; 13(10): 987-996.

An exon 11 antisense oligonucleotide (ASO) that increased lamin C production has been shown to shift the output of LMNA more toward lamin C and reduce levels of the mutant protein in fibroblasts derived from patients with HGPS (Lee et al., J Clin Invest. 2016 Apr. 1; 126(4):1592-602).

Exon skipping ASOs directed against an intron splice silencer in SMN2 increase the amount of full-length SMN transcript in the CNS, restoring SMN to treat subjects with spinal muscular atrophy (SMA) (see Burghes and McGovern, Genes Dev. 2010 Aug. 1; 24(15): 1574-1579). ASO drug nusinersen enhanced exon 7 inclusion in a clinical trial, see Chiriboga et al., Neurology. 2016 Mar. 8; 86(10): 890-897.

Specific ASOs for use in exon 51 skipping therapy, e.g., in DMD, include PRO051 (2OME-PS, Netherlands) and AVI-4658 (PMO, UK). A plurality of ASOs can also be used, e.g., to induce exon skipping in multiple exons; see, e.g., Wood et al., Brain. 2010 April; 133(Pt 4):957-72 See also Fletcher et al., Mol Ther Nucleic Acids. 2012 October; 1(10): e48; McClorey et al., Curr Opin Pharmacol. 2005 October; 5(5):529-34.

Similar methods can be used in DM1, as described in Chamberlain and Chamberlain, Nature Medicine 16:170-171 (2010). For example, an ASO inhibiting mutant DMPK transcripts can be used, e.g., a 149-bp antisense RNA complementary to the (CUG)13 repeats and to the 110-bp region following the repeats sequence has been described, see Furling et al., Gene Ther. 2003 May; 10(9):795-802. See also Magaña and Cisneros, J Neurosci Res. 2011 March; 89(3):275-85; Thornton et al., Curr Opin Genet Dev. 2017 June; 44:135-140; Gao and Cooper, Hum Gene Ther. 2013 May; 24(5): 499-507.

See also Gao et al., Hum Gene Ther. 2013 May; 24(5): 499-507; Wheeler et al., Science 2009, 325, 336-339; Wheeler et al., Nature 2012, 488, 111-115; Wojtkowiak-Szlachcic et al., Nucleic Acids Res. 2015, 43, 3318-3331; Mulders et al., Proc. Natl. Acad. Sci. USA 2009, 106, 13915-13920; Francois et al., Nat. Struct. Mol. Biol. 2011, 18, 85-87; Cavazzana-Calvo et al., Science 2000, 288, 669-672; Cornetta et al., Mol. Ther. J. Am. Soc. Gene Ther. 2011, 19, 557-566.

Small molecule therapeutics can also be used, e.g., PTC124, a 284.24-Da, achiral, 1,2,4-oxadiazole linked to fluorobenzene and benzoic acid rings, which selectively induces ribosomal read-through of premature but not normal termination codons, see Welch et al., Nature 447: 87-91, 2007, and has been used in clinical trials for DMD.

EXAMPLES

The invention is further described in the following examples, which do not limit the scope of the invention described in the claims.

Materials and Methods

The following materials and methods were used in the Examples set forth below.

Human subjects. The Partners Health Service/MGH IRB approved all studies involving human subjects described here. We recruited study participants from the MGH Neuromuscular Diagnostic Center. Three groups were studied: (1) individuals with DM1 (N=23), (2) individuals with a muscular dystrophy besides DM (N=8 total; 6 DMD, 1 BMD, 1 FSHD), and (3) individuals with no known muscular dystrophy (unaffected; N=22) that were either a parent, spouse, or cousin of a study participant with muscular dystrophy. Inclusion criteria for DM1 subjects were age 13 years or older, a diagnosis of DM1 based on genetic testing that identified a DMPK-CTG repeat expansion of ≥50, or clinical diagnosis of DM1 and a $1^{st}$ degree relative with DM1 due to a DMPK-CTG repeat expansion of ≥50, and ability to provide informed consent or assent for participation. Inclusion criteria for MDC subjects included known diagnosis of DMD, BMD, or FSHD, ages 13 years or older, and ability to provide informed consent. Inclusion criteria for unaffected individuals were age 18 years or older, no known history of any muscular dystrophy, and ability to provide informed consent. The training cohort consisted of a combined 34 DM1 or UA participants chosen randomly, and the remaining 11 combined DM1 and UA subjects comprised the validation cohort. Prior to participation in the study, informed consent was obtained for blood and/or urine collection from all subjects; due to severe autism, informed consent for the individual with Becker muscular dystrophy was obtained from his mother/legal guardian, according to IRB protocol. Subject information is shown in Tables 1A-1B.

Tables 1A-1B, Clinical Data from DM1 Subjects

TABLE 1A

| Subjects | # Male | # Female | Mean age | Age range |
|---|---|---|---|---|
| DM1 | 19 | 8 | 41 | 17-63 |
| UA | 7 | 19 | n/a | n/a |
| MDC | 9 | 1 | 24 | 14-49 |

TABLE 1B

| ID | Leukocytes | Nitrite | Urobilinogen | Protein | pH | Blood | Specific gravity | Ketone | Bilirubin | Glucose |
|---|---|---|---|---|---|---|---|---|---|---|
| DM1 | − | − | 3.5 | +/− | 5 | − | 1.025 | − | − | − |
| DM1 | − | − | 3.5 | +/− | 6 | − | 1.020 | − | − | − |
| DM1 | − | − | 3.5 | +/− | 5 | − | 1.020 | − | − | − |
| DM1 | − | − | 3.5 | +/− | 5 | − | 1.010 | − | − | − |
| DM1 | − | − | 3.5 | +/− | 5 | − | 1.020 | − | − | − |
| DM1 | − | − | 3.5 | +/− | 5 | − | 1.030 | − | − | − |
| DM1 | − | − | 3.5 | +/− | 5 | − | 1.020 | − | − | − |
| DM1 | − | − | 3.5 | +/− | 6 | − | 1.015 | − | − | − |
| DM1 | − | − | 3.5 | +/− | 5 | − | 1.015 | − | − | − |
| DM1 | − | − | 3.5 | +/− | 5 | − | 1.015 | − | − | − |
| DM1 | − | − | 1(17) | +/− | 6 | − | 1.010 | − | − | − |
| DM1 | − | − | 3.5 | +/− | 5 | − | 1.030 | − | − | − |
| DM1 | − | − | 3.5 | − | 6 | − | 1.005 | − | − | − |
| DM1 | − | − | 3.5 | +/− | 5 | − | 1.030 | − | − | − |
| DM1 | − | − | 3.5 | +/− | 6 | − | 1.015 | − | − | − |
| DM1 | +/− | − | 3.5 | − | 5 | − | 1.015 | − | − | − |
| DM1 | + | − | 3.5 | +/− | 5 | − | 1.030 | − | − | − |
| UA | + | − | 3.5 | − | 5 | − | 1.025 | − | − | − |
| UA | − | − | 3.5 | +/− | 5 | − | 1.010 | − | − | − |
| UA | − | − | 3.5 | +/− | 6.5 | − | 1.010 | − | − | − |
| UA | − | − | 3.5 | +/− | 5 | − | 1.015 | − | 1(17)+ | − |
| UA | − | − | 3.5 | − | 6.5 | − | 1.010 | − | − | − |
| UA | − | − | 3.5 | +/− | 5.5 | − | 1.010 | − | − | − |
| UA | − | − | 3.5 | +/− | 5 | − | 1.010 | − | − | − |
| UA | − | − | 3.5 | +/− | 6.5 | − | 1.010 | − | − | − |
| UA | − | − | 3.5 | − | 5 | − | 1.015 | − | − | − |
| UA | − | − | 3.5 | +/− | 7.5 | − | 1.010 | − | − | − |
| UA | − | − | 3.5 | − | 5 | − | 1.010 | − | − | − |
| UA | +/− | − | 3.5 | − | 5 | − | 1.015 | − | − | − |
| UA | − | − | 3.5 | +/− | 5 | +/− | 1.025 | − | − | − |
| UA | +/− | − | 3.5 | − | 6.5 | +/− | 1.010 | − | − | − |
| UA | − | − | 3.5 | +/− | 5 | − | 1.025 | − | − | − |
| UA | − | − | 3.5 | +/− | 7 | − | 1.010 | − | − | − |

(1A) Gender, age, and age range of participating DM1, MDC, and UA subjects.
(1B) We examined urine from a subset of 18 DM1 and 16 UA subjects using urinalysis reagents strips (ACON Laboratories) as a general screening tool for urinary tract disorders, endocrine disorders, or metabolic or systemic diseases that affect kidney function. Specific gravity values (detection range 1.000-1.030) tended to be higher in DM1 than in UA subjects (P = 0.0568; Mann-Whitney test). Specific gravity is measure of the kidney's ability to concentrate the urine. Urobilinogen detection range is 0.2-1.0 mg/dL (3.5-200 μmol/L).

Collection and processing of human urine. Subjects donated urine (range from 20-120 milliliters) in a standard specimen container. To remove cells, we centrifuged the entire volume at 2,450×g for 10 minutes at room temperature, passed the supernatant through a 0.8 μm filter into sterile 50 ml tubes, and placed on wet ice within 2 hours of collection. We proceeded with exRNA isolation from specimens either immediately or after storage at 4° C. overnight. To analyze total RNA in urine cell pellets, we used Trizol (Life Technologies) according to manufacturer recommendations.

Collection and processing of human serum. Blood was collected in two standard red top serum separator tubes (Becton Dickinson), incubated at room temperature for 30-45 minutes, and centrifuged at 2,450×g for 10 minutes at room temperature. To remove any remaining cells, we passed the serum through a 0.8 μm filter into a sterile 15 ml tube, placed on wet ice within 2 hours of collection, and stored at −80° C. The volume of serum recovered ranged from 5.5-8.5 ml. The blood sample from one individual with DM1 was unusable due to hemolysis and total volume of less than 3 ml.

Experimental mice. The MGH IACUC approved all experiments involving mice. $HSA^{LR}$ transgenic and Mbnl1 knockout ($Mbnl1^{\Delta E3/\Delta E3}$) models of DM1 (both FVB background) have been described[2,26]. FVB wild-type mice served as controls. $HSA^{LR}$ mice that were treated with antisense oligonucleotide (ASO) 445236 received subcutaneous injections of 25 mg/kg twice weekly for 4 weeks, as previously described[6]. ASO 445236 was a gift of Dr. Frank Bennett at Ionis Pharmaceuticals (Carlsbad, CA).

Nanoparticle tracking. To determine nanoparticle size and concentration, we used the Nanosight LM10 system and Nanoparticle Tracking Analysis 2.0 analytical software according to manufacturer instructions (Malvern). The system uses a laser beam, light microscope, and CCD camera to visualize and video record particles in liquid suspension moving under Brownian motion. For accurate measurements, we diluted serum samples 1:1000 and urine either 1:10 or 1:20 in saline to stay in the target concentration range of $1.0 \times 10^8$ and $2.5 \times 10^9$ particles/milliliter. We recorded 60-second videos and analyzed data in auto mode.

Isolation of exRNA from biofluids. We ultracentrifuged urine and serum samples at 100,000×g 2 hours at 4° C., removed the supernatant, extracted RNA from the translucent ribonucleoprotein pellet using 700 μl Trizol (Life Technologies) according to manufacturer instructions. To enhance RNA pellet visibility, we added 1.4 μl linear acrylamide (Ambion) to each sample and mixed well prior to isopropanol precipitation. Pellets were re-suspended in molecular grade water.

exRNA analysis. We measured optical density spectra using a microvolume spectrophotometer (Nanodrop). To measure exRNA size, quality, and total mass of recovered, we used chip-based capillary gel electrophoresis according to manufacturer instructions (2100 Bioanalyzer, Agilent Technologies). Using electropherogram traces, a software algorithm (Agilent) automatically determined the RNA integrity number (RIN) based on using a numbering system of 1 (most degraded) to 10 (fully intact)[37].

Quantitative real-time RT-PCR (qPCR). To quantitate DMPK gene expression, we used Taqman qPCR (Applied Biosciences 7500) and standard assays for GAPDH, and GTF2B (Applied Biosciences, FAM-MGB; assay IDs Hs00976255_m1 and Hs02758991_g1) as normalization controls. The primer probe set for DMPK was published previously[6]. To determine expression levels, we used the mean of duplicate assays from individual samples.

RT-PCR analysis of splicing outcomes. We generated cDNA using Superscript III reverse transcriptase (Life Technologies) and random primers, and performed PCR using Amplitaq Gold DNA polymerase (Life Technologies) and gene specific primers (Tables 2 and 3). We used previously published primers for INSR and APT2A1[3, 38] and designed all other primers using Primer3 software[39, 40]. Due to the small size of the exRNA species, we targeted the product size for exon exclusion isoforms to be ~100-200 nucleotides whenever possible. Total RNA from normal human skeletal muscle and kidney (Ambion AM7982 and AM 7976) served as tissue controls. We separated PCR products using agarose gels, stained with SYBR I green nucleic acid gel stain, and quantitated band intensities using a transilluminator, CCD camera, XcitaBlue™ conversion screen, and Image Lab image acquisition and analysis software (Bio-Rad).

TABLE 2

PCR primers for human transcripts.

| Gene | Left primer (5'-3') | # | Right primer (5'-3') | # | Target exon(s) | + ex size (nt) | − ex size (nt) |
|---|---|---|---|---|---|---|---|
| ALPK3 | GAGCTACCTGCTCAGCGTG | 1. | CTGTGACGATGCAGGTGAAC | 2. | 2 | 194 | 155 |
| ANK2 | CCGATAACCAGCCTGAGACC | 3. | ACGGTGTGTCCATGCTCATC | 4. | 21 | 223 | 130 |
| ARFGAP2 | GTGCCGTTCCTAATCACTCC | 5. | GTGAGGTGCCAAGCAGGTC | 6. | 6 | 186 | 104 |
| BIN1 | AACCTCAATGATGTGCTGGTC | 7. | CTCTGGCTCGTGGTTGACTC | 8. | 11 | 213 | 168 |
| CACNA1S | TGATTGTCATTGGCAGCATC | 9. | AGGGTTCGCACTCCTTCTG | 10. | 29 | 205 | 148 |
| CAMK2B | AGCCATCCTCACCACCATG | 11. | AGGAGGAAGCGTCCCTTTG | 12. | 13 | 217 | 142 |
| CAPZB | AATCAGAAGTACGCTGAACGAG | 13. | CCTCCACCAGGTCATTCTTC | 14. | 8 or 9 | 238 | 113 |
| CLASP1 | TATTGATGTGAACGCAGCAG | 15. | CCGGTTATCAGGTGTAGAGG | 16. | 20 | 202 | 178 |
| CLCN1 | CCTGAAGGAATACCTCACAATG | 17. | TGAGGACAGCAGCACAGATG | 18. | 7a | 200 | 134 |
| COPZ2 | CGGCTTGACTGAACAGAGTG | 19. | CTGGCTGGAGACCTTAGGAG | 20. | 9b | ~320 | 213 |
| DMD | TACGGTGACCACAAGGGAAC | 21. | TTTCACAGTGGTGCTGAGATAG | 22. | 18 - 22 deletion | n/a | 174 |
| DMD | CCAGCTGGTTGAGCATTGTC | 23. | GTTCAGCTTCTGTTAGCCACTG | 24. | 24 - 43 deletion | n/a | 144 |
| DMD | AATTGGGAAGCCTGAATCTG | 25. | CTCCGGTTCTGAAGGTGTTC | 26. | 46 - 52 deletion | n/a | 119 |
| DMD | AGCCACTCAGCCAGTGAAG | 27. | GCAGAATAATCCCGGAGAAG | 28. | 51 - 53 deletion | n/a | 214 |
| DMD | ACTGGCATCATTTCCCTGTG | 29. | GGGTTCCAGTCTCATCCAGTC | 30. | 67 | 267 | n/a |
| DMD | GCTACCTGCCAGTGCAGAC | 31. | TGCGTGAATGAGTATCATCG | 32. | 71 | 132 | 87 |
| DMD | GAGCAACTCAACAACTCCTTCC | 33. | TAAGGACTCCATCGCTCTGC | 34. | 78 | 128 | 96 |
| FN1 | CAAGGATGACAAGGAAAGTGTC | 35. | TGGACCAATGTTGGTGAATC | 36. | 25 | 364 | 91 |
| GFPT1 | CCTCTGTTGATTGGTGTACGG | 37. | GTGCTGTCCACACGAGAGAG | 38. | 9 | 170 | 116 |
| IMPDH2 | CCAGGCTGGTGTGGATGTAG | 39. | TTGTACACTGCTGTTGCTTGG | 40. | 8 or 9 | 255 | 159 |
| KIF13A | GGACACTGCCACTTATGGTTG | 41. | TGAGTGCATCTGACCACCTC | 42. | 25 | 183 | 144 |
| LMNA | AGATGACCTGCTCCATCACC | 43. | TACATGATGCTGCAGTTCTGG | 44. | 11 | 321 | 171* |
| MAP3K4 | GGTACCTCGATGCCATAGTGAC | 45. | CAGCTATGGAAGCCAATCG | 46. | 17 | 260 | 110 |
| MAPT | CGAAGTGATGGAAGATCACG | 47. | GTGTCTCCAATGCCTGCTTC | 48. | 2 + 3 | 309; 222 | 135 |
| MAPT | AACGAAGATCGCCACACC | 49. | CCACTGCCACCTTCTTGG | 50. | 10 | 296 | 242 |
| MBNL1 | CTGCCCAATACCAGGTCAAC | 51. | GGCTAGAGCCTGTTGGTATTG | 52. | 7 | 230 | 176 |

TABLE 2-continued

PCR primers for human transcripts.

| Gene | Left primer (5'-3') | # | Right primer (5'-3') | # | Target exon(s) | + ex size (nt) | - ex size (nt) |
|---|---|---|---|---|---|---|---|
| MBNL2 | CAGCACCAAGCCAACCAAG | 53. | GAGCCTGCTGGTAGTGCAAG | 54. | 6 | 226 | 172 |
| NCOR2 | GCTGGAGGCCATAATTAGAAAG | 55. | GAGTGCACTGAGGAGACAGAG | 56. | 45a | 282 | 144 |
| NFIX | AGCCCTGTTGATGACGTGTT | 57. | AGTGCAGGGCTGATGCTGT | 58. | 7 | 250 | 127 |
| NRAP | AGGCGCTGCACATTATCAC | 59. | ATAGCGGCCTCTCATGTGG | 60. | 12 | 235 | 130 |
| OPA1 | GGATTGTGCCTGACATTGTG | 61. | CCACGATCTGTTGCTCTAAACG | 62. | 4b | 250 | 196 |
| PHKA1 | CTGGACCTGAGGGTAAGCTG | 63. | GGGAAGCCTGAAATAACTTCG | 64. | 19 | 318 | 141 |
| PHKA1 | TATCCACGAGATTGGTGCTG | 65. | GTTGCCATTGACCTTGACG | 66. | 28 | 212 | 173 |
| SOS1 | TGGTGCTTCCAGTACCACAG | 67. | GGCAGATTCTGGTCGTCTTC | 68. | 25 | 208 | 163 |
| UBE2D3 | GTCGCCTGCTTTAACAATTTC | 69. | CTTGGGCAACTGTTCTCTTG | 70. | 10 | 456 | 406 |
| VPS39 | TAGGATTCGGAAGGACGTTG | 71. | CTCACCGGTCTCTGTGTGC | 72. | 3 | 274 | 241 |

SEQ ID NO:
*progerin

TABLE 3

PCR primers for mouse transcripts.

| Gene | Left primer (5'-3') | # | Right primer (5'-3') | # | Target exon(s) | + ex size (nt) | - ex size (nt) |
|---|---|---|---|---|---|---|---|
| mCamk2b | GCCACACGGAATTTCTCAG | 73. | CAGGAGGGAGAGATCCTTTG | 74. | 13 | 196 | 121 |
| mCapzb | ATCCGAAGCACGCTGAATG | 75. | GCCTCCACCAGGTCGTTC | 76. | 9 | 238 | 125 |
| mClasp1 | GTCGACGACAGGATCTCTCC | 77. | GAGCTCTGCCGTCTCGTG | 78. | 20 | 198 | 174 |
| mMap3k4 | CAACAGAATCAGCGATGCCATC | 79. | TGGTCTGGCTGATGAGTGTTCG | 80. | 17 | 355 | 199 |
| mMbnl1 | ACCTGCAAGCCAAGATCAAG | 81. | TGTTGGCTAGAGCCTGTTGG | 82. | 7 | 255 | 201 |
| mMbnl2 | TCACCCTCCTGCACACTTG | 83. | TCTTTGGTAAGGGATGAAGAGC | 84. | 6 | 194 | 140 |
| mNcor2 | CAGGCGGTGCAAGAACAC | 85. | TTCGGCTGCTAGGTCTGC | 86. | 45a | 253 | 112 |
| mNfix | TCGACGACAGTGAGATGGAG | 87. | CTGGATGATGGACGTGGAAG | 88. | 7 | 238 | 115 |

SEQ ID NO:

Sample size. Splicing patterns in human urine and serum, or even whether alternative splice isoforms are present or detectable in these biofluids, were unknown. Therefore, we were unable to choose a sample size ahead of time to ensure adequate power to detect disease-specific differences. Instead, we chose a sample size based on splicing outcomes in muscle biopsies[4] and a goal of enrolling a similar number of DM1 and UA controls. In mice, we chose sample sizes for splicing analysis in muscle based on previously reported differences in muscle tissue of these models[2, 3, 5, 6]. Mice ranged from 2 to 4 months of age and were chosen randomly by genotype, stratified for sex to allow an approximately equal number of females and males, and examined without blinding Statistics. Group data are presented as mean±s.e.m. We compared groups using an unpaired two-tailed t-test or analysis of variance (ANOVA) as indicated. We used the F test to compare variances between DM1 and UA control samples analyzed by qPCR and RT-PCR (Table 4). In groups with statistically significant difference in variance, we used t-test with Welch's correction to determine differences between groups. A P value<0.05 was considered significant.

Principle component analysis was performed using R statistical software. The principle component score for each subject was calculated using a linear combination of the 10 splicing outcomes shown in FIG. 2 (INSR, MBNL2, SOS1, MBNL1, CLASP1, MAP3K4, NFIX, NCOR2, VPS39, and MAPT).

TABLE 4

Variance between groups.

| Transcript | P value | Are variances significantly different? | Variance greater in DM1 or UA? |
|---|---|---|---|
| Urine qPCR Ct values | | | |
| DMPK | 0.7302 | no | n/a |
| GTF2B | 0.9178 | no | n/a |
| GAPDH | 0.3577 | no | n/a |
| Urine qPCR normalized values | | | |
| DMPK-GTF2B | 0.0171 | yes | UA |
| DMPK-GAPDH | 0.0226 | yes | UA |
| Serum qPCR Ct values | | | |
| DMPK | 0.3377 | no | n/a |
| GTF2B | 0.8546 | no | n/a |
| GAPDH | 0.4702 | no | n/a |
| Serum qPCR normalized values | | | |
| DMPK-GTF2B | 0.4137 | no | n/a |
| DMPK-GAPDH | 0.6131 | no | n/a |
| Serum splicing | | | |
| INSR ex 11 | 0.6479 | no | n/a |
| MBNL2 ex 6 | 0.0787 | no | n/a |
| SOS1 ex 25 | 0.9233 | no | n/a |
| NFIX ex 7 | 0.1731 | no | n/a |
| VPS39 ex 3 | 0.4998 | no | n/a |

We used the F test to compare variances between DM1 and UA control groups for gene expression in urine and serum samples analyzed by qPCR and splicing in serum samples by RT-PCR. In groups with statistically significant difference in variance, we used t-test with Welch's correction to determine differences between groups. The difference in variances of some groups may represent true differences in the two populations, and may be as important as the finding of different means (FIG. 1, FIGS. 7G and 7H, FIGS. 11A and 11B).

Predictive model. We used principal component regression to develop a predictive model of DM1 using the splicing quantification of the 10 genes, shown in FIG. 2. The pls package in R, which uses singular value decomposition algorithm for the fitting, was used to implement the model[41]. For the model, DM1 (N=23) and UA (N=22) subjects were randomly assigned to a training cohort that consisted of 17 subjects with DM1 and 17 unaffected controls. For subjects that provided $2^{nd}$ samples, the mean value of the splicing quantitation measurements was used. Only the first principal component was used for prediction.

Example 1. Characterization of exRNA in Biofluids from DM1 and UA Subjects

Figure 7A:
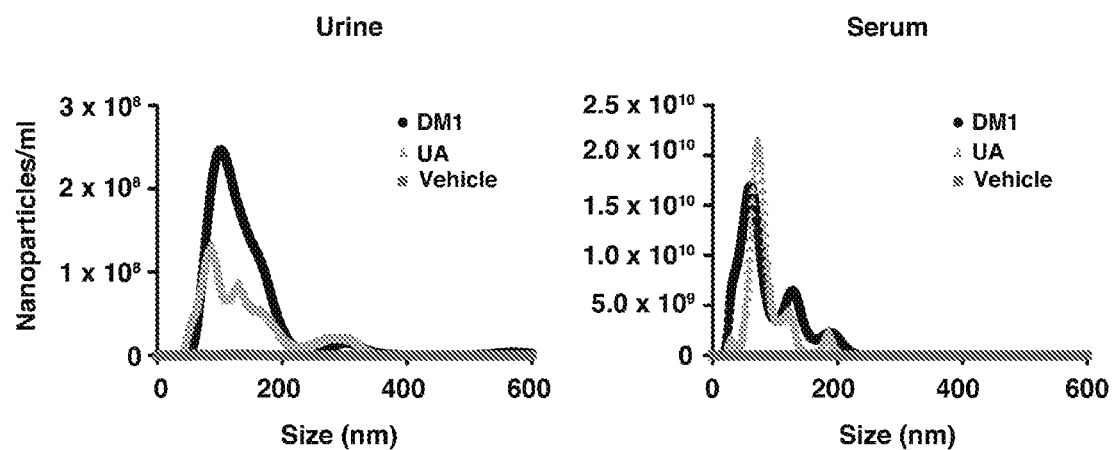
FIGS. 7A-H. Characterization of exRNA in human urine and serum from DM1 and unaffected (UA) control subjects. (A) Nanoparticle analysis in human urine and serum samples. We determined nanoparticle size and concentration in urine and serum samples from DM1 (N=12 urine, 10 serum) and UA control (N=9 urine, 8 serum) subjects. For accurate measurements, we diluted serum samples 1:1000 and urine either 1:10 or 1:20 in saline to stay in the target concentration range of $1.0 \times 10^8$ and $2.5 \times 10^9$ particles/milliliter (see Methods). Representative traces of nanoparticle size from DM1 and UA subjects in urine (left) and serum (right) are shown. (B) Mean nanoparticle size from each individual sample in urine (left) and serum (right) ±s.e.m. Note that nanoparticle concentration in urine was lower than serum, while mean particle size was higher. (C) Using ultracentrifugation and Trizol (see Methods), we isolated exRNA from urine (N=14 DM1 and 12 UA) and serum (N=5 DM1 and 7 UA) samples and examined optical density using a microvolume spectrophotometer (Nanodrop). Representative optical density spectra of exRNA urine (left) and serum (right) are shown. Vehicle (water) served as reference. The peak of 268 nm reflects residual phenol that was used to purify the RNA (Krebs et al., Anal Biochem 387, 136-138 (2009)), which seemed to have no effect on electropherogram analysis (E) or cDNA synthesis (FIGS. 2A-C, 9A-B, 10, 11A-B). (D) We used capillary gel electrophoresis (Agilent Bioanalyzer) to analyze the concentration, size distribution, and quality of exRNA in urine (N=22 DM1; N=21 UA controls) and serum (N=5 DM1 and 7 UA controls). Using the RNA concentration, we determined the quantity of RNA recovered per volume of urine (left) or serum (right) starting material (range 38 ml-120 ml urine; 5.5-8.5 ml serum). Individual data points from each sample are shown. Error bars represent the mean±s.e.m. (E) Representative electropherogram traces of exRNA size in nucleotides from urine (left) and serum (right). Most of the species are <200 nt. (F) RNA integrity number (RIN) in urine (left) and serum (right), as calculated from electropherogram traces using a software algorithm (Agilent). RIN results for three DM1 and two UA serum samples were read as undetermined by the software algorithm. Error bars represent mean±s.e.m. (G) qPCR analysis of GAPDH and DMPK gene expression in human urine samples (N=14 DM1 and 13 UA controls). Individual data points indicate the mean of duplicate assays from each individual sample examined. Error bars represent mean±S.E.M.  P=0.003, * P=0.0002; t-test with Welch's correction. (H) Serum mRNA expression of reference gene GAPDH (left) and DMPK relative to GAPDH (right) by qPCR. Error bars represent mean±s.e.m.
Figure 7B:
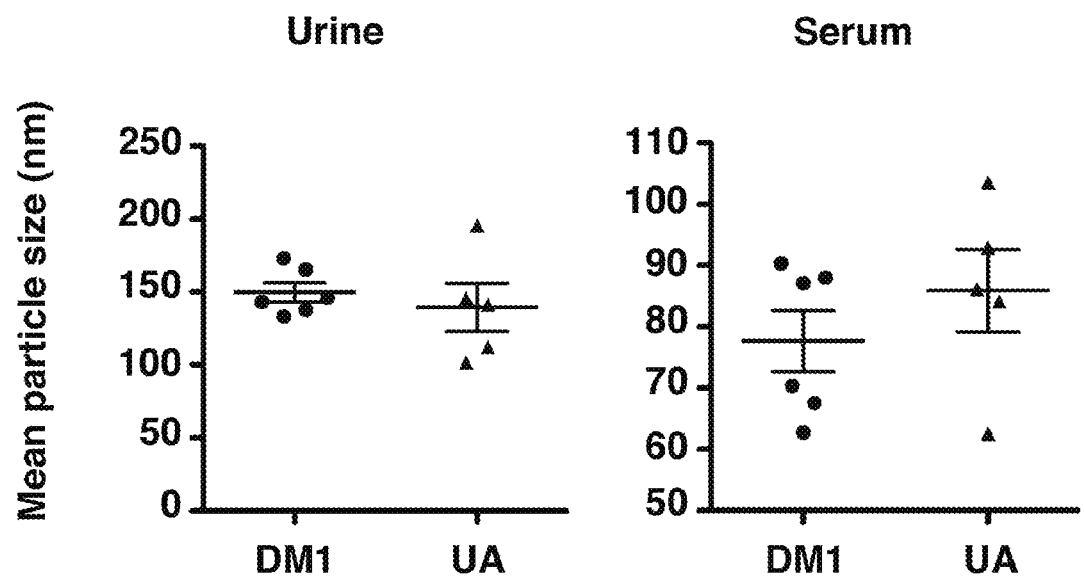
Figure 7C:
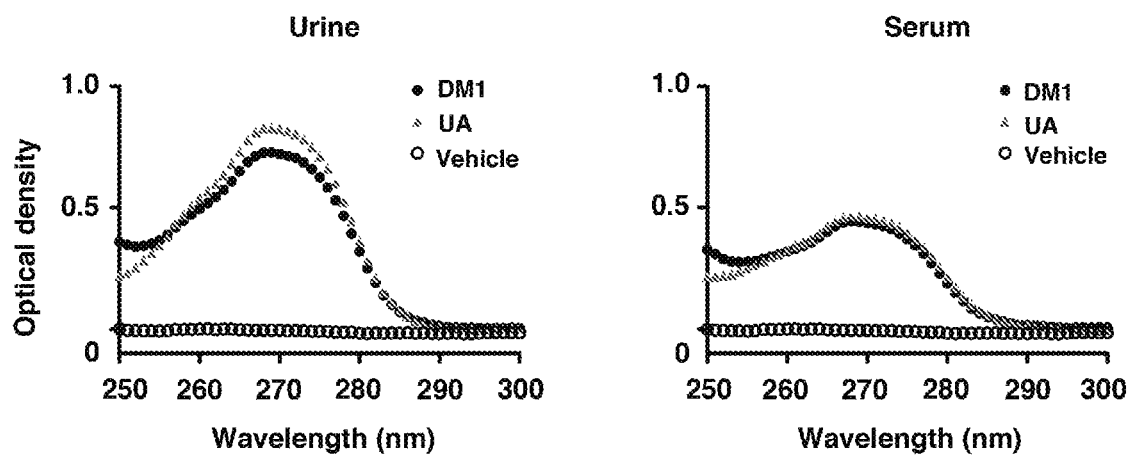
Figure 7D:
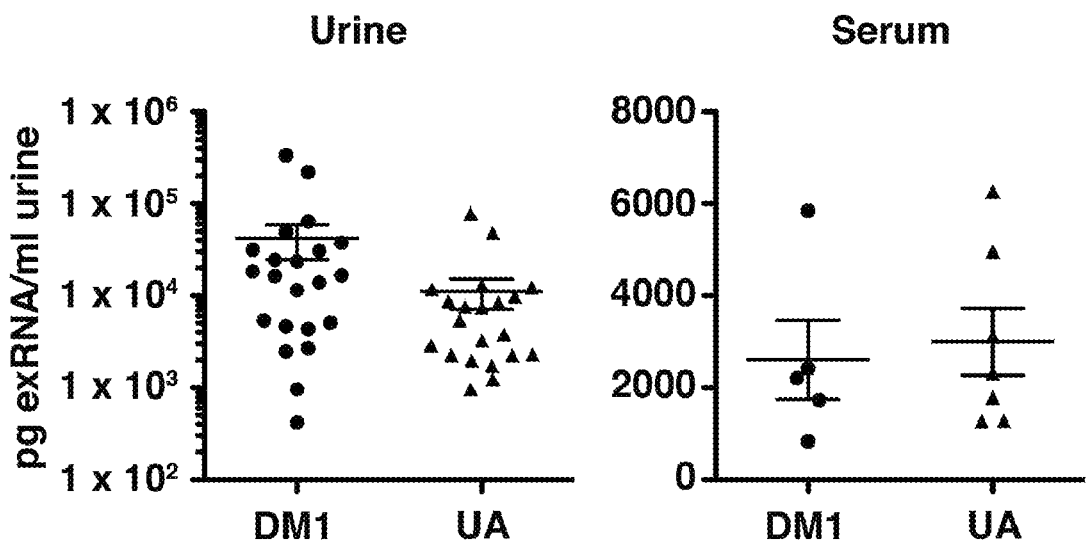
Figure 7E:
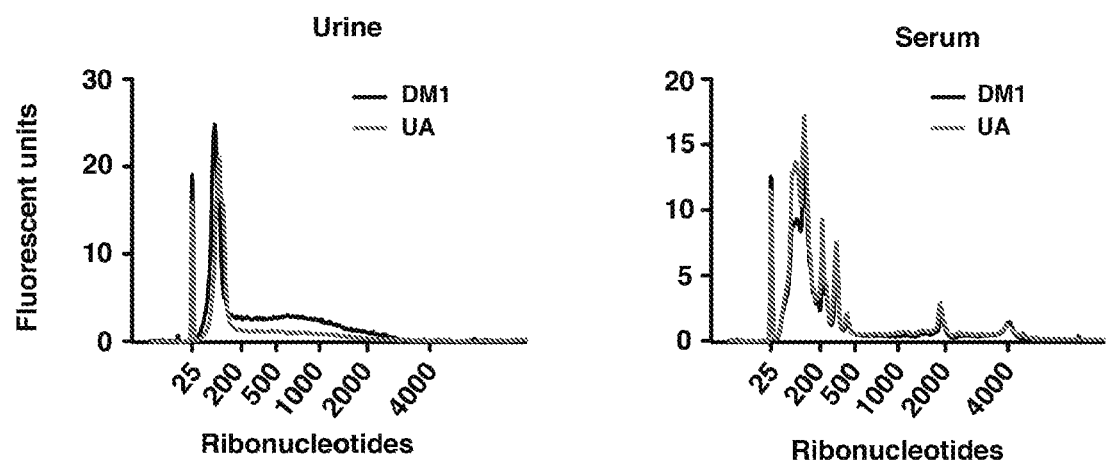
Figure 7F:
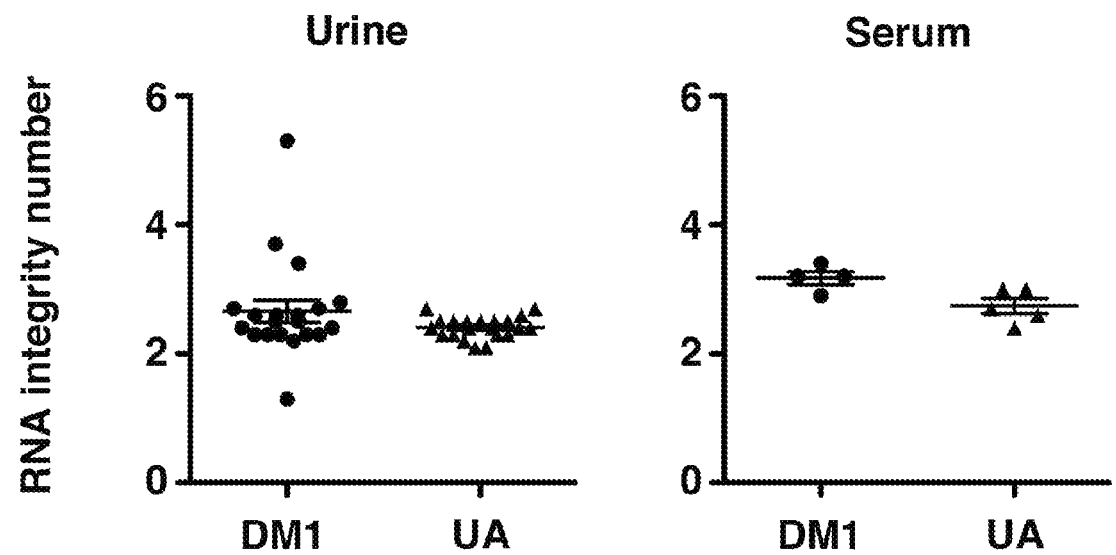

To examine the possibility of detecting biomarkers of muscular dystrophies (MDs) in human biofluids, we analyzed exRNA microarray and raw sequencing data from two previous studies and found that more than 30 transcripts previously reported as "splicing biomarkers" in DM1 muscle biopsy tissue could be detected in control human serum and urine (Tables 5 and 6)[20, 21]. To determine whether splice variants of these transcripts are also detectable in human biofluids, we collected blood and/or urine from 23 subjects with DM1, 22 unaffected (UA) individuals, and 8 MD controls (MDC) (Table 1). First we screened biofluids for the presence of exRNA and found that nanoparticle content was greater in serum than urine, and showed no difference in number or size between DM1 and controls (FIG. 7A). Conversely, nanoparticle size spanned a larger range in urine than serum in both DM1 and UA controls (FIG. 7B). Optical density curves at 260 nm appeared similar in DM1 and UA controls in both urine and serum (FIG. 7C). Using capillary gel electrophoresis, we calculated RNA mass recovered per milliliter of biofluid, exRNA size distribution, and RNA quality (FIG. 7D to F). Although the concentration of exRNA was 2.5-3 fold greater in serum than urine, the total recovery of exRNA was greater in urine due to larger specimen volume (20-120 ml urine vs 5.5-8.5 ml serum).

TABLE 5

Transcripts mis-spliced in DM1 muscle tissue and other muscle transcripts that are expressed in human serum extracellular RNA (exRNA).

| Gene Name | Systematic name | Sequence | # | Probe Name | Avg |
|---|---|---|---|---|---|
| DMPK | NM_004409 | TTTTGGATGCACTGAGACCCCGACATTCCT CGGTATTTATTGTCTGTCCCCACCTAGGAC | 89. | A_23_P50535 | 5.66 |
| INSR* | NM_000208 | GTTCAGAGATCGTTCCTATACATTTCTGTT CATCTTAAGGTGGACTCGTTTGGTTACCAA | 90. | A_23_P4764 | 4.87 |
| MBNL2* | NM_144778 | ATCTTTCTGTAACACTTAAAGAATTCCCTC ATTCATTACCTTACAGTGTAAACAGGAGTC | 91. | A_24_P56317 | 4.60 |
| SOS1* | NM_005633 | TTATTACCACCACGAGAACCTGTGAGGACA CCTGATGTTTTCTCAAGCTCACCACTACAT | 92. | A_23_P343808 | 4.77 |
| CLASP1* | NM_015282 | TTATCAAGCGTAATGTTACACTTTAAAGGA CAGCAAATAAGAACTTTGTAGAATCCCACC | 93. | A_23_P311232 | 4.57 |
| MBNL1* | NM_021038 | ATCCTTTCAAACCCTCATGACTGACAAAAA CTCCATGGGGCCAAATCTGCCTGAAGATCA | 94. | A_23_P357811 | 6.26 |
| MAP3K4* | NM_005922 | AAAGATTAAGCCCTGAAGGAAAGGACTTCC TTTCTCACTGCCTTGAGAGTGACCCAAAGA | 95. | A_23_P42096 | 5.07 |
| NFIX* | NM_002501 | ACCTGGTCATGGTGATTTTGTTTAAGGGGA TCCCCCTGGAAAGTACTGATGGGGAGCGGC | 96. | A_23_P165295 | 4.85 |
| NCOR2* | NM_006312 | TTCGATGCGTATTCTGTGGCCGCCATTTGC GCAGGGTGGTGGTATTCTGTCATTTACACA | 97. | A_23_P203891 | 5.84 |

TABLE 5-continued

Transcripts mis-spliced in DM1 muscle tissue and other muscle transcripts that are expressed in human serum extracellular RNA (exRNA).

| Gene Name | Systematic name | Sequence | # | Probe Name | Avg |
|---|---|---|---|---|---|
| VPS39* | NM_015289 | GGCAAGAACAGCAGGACGCTGGTTTAAAAA TAACTCACCGCCAAACCTGTGGAGCAGTGT | 98. | A_24_P167825 | 5.08 |
| MAPT* | NM_016835 | ACCAGTTCTCTTTGTAAGGACTTGTGCCTC TTGGGAGACGTCCACCCGTTTCCAAGCCTG | 99. | A_23_P207699 | 5.19 |
| KIF13A | NM_022113 | TCATATTCATTCCCTGGGATGTTTAGTTAC CAGTTTTCCCAAAGTGTTCTGGTAGCATCT | 100. | A_23_P214111 | 4.69 |
| DMD | NM_004019 | AGAAAATATAGTCACAGGAAACTACTCACG TAAGTAGTAATGATTCTCAAGATCAAAGGG | 101. | A_23_P321860 | 4.44 |
| CLCN1 | NM_000083 | TCCATCTTCCAGTCCCTGCTTCACTGCTTG CTGGGCAGAGCTCGCCCCACAAAGAAGAAA | 102. | A_23_P59772 | 6.90 |
| ATP2A1 | NM_173201 | GTCCTCAAGATCTCACTGCCAGTCATTGGG CTCGACGAAATCCTCAAGTTCGTTGCTCGG | 103. | A_23_P72462 | 5.17 |
| CAPZB | NM_004930 | GCTGAACGAGATCTACTTTGGAAAAACAAA GGATATCGTCAATGGGCTGAGGTCTGTGCA | 104. | A_23_P126752 | 5.22 |
| CACNA1S | NM_000069 | TGGAGTCCTCCATGCCTGAGGACAGAAAGA GCTCCACACCAGGGTCTCTTCATGAGGAGA | 105. | A_23_P85765 | 5.80 |
| CAMK2B | NM_172082 | GATCATTAAGACCACGGAGCAGCTCATCGA GGCCGTCAACAACGGTGACTTTGAGGCCTA | 106. | A_23_P42882 | 4.79 |
| COPZ2 | NM_016429 | GGTTCTTCAGTCTGCCAAGGAACAAATTAA ATGGTCGTTATTGAAATGAAGGCTGTGGAT | 107. | A_23_P101093 | 4.76 |
| GFPT1 | NM_002056 | TGAAGGCATCCTTGCTGGTGAATTGAAACA TGGCCCTCTGGCTTTGGTGGATAAATTGAT | 108. | A_23_P44083 | 6.03 |
| IMPDH2 | NM_000884 | TTGGACTCTTCCCAGGGAAATTCCATCTTC CAGATCAATATGATCAAGTACATCAAAGAC | 109. | A_24_P166042 | 5.00 |
| ALPK3 | NM_020778 | TGTGTACCCCTTAGCAGGGTGTCTGGGGAC TTACGCCTTTGGAATTGCTCTTCATTCAGA | 110. | A_23_P348728 | 5.95 |
| ANK2 | NM_001148 | CCCCATCCTCTTTAACTATAAAGCTAATTT GTGACCAAAGATGGCATCCTTCATACTGGA | 111. | A_23_P133068 | 5.50 |
| BIN1 | NM_139346 | AGCAAAGGGAAATCAAGAGGAGACCCCCAG GCAGAGGGGCGTTCTCCCAAAGATTAGGTC | 112. | A_23_P165333 | 5.63 |
| NRAP | NM_198060 | GGCCAGAGAGGAAGTTTGTTCACCAGAGAC AGGCTTCAGATGGCTTTGATTTCGGCAAGC | 113. | A_23_P402765 | 4.58 |
| OPA1 | NM_130837 | GTGCTTCCCAGCCTCACAATGTGGGAATTT GACATAGGATGAGAGTCAGAGTATAGGTTT | 114. | A_23_P211797 | 6.54 |
| PHKA1 | NM_002637 | GCTATGTTCAGAAAGATGCTTGGGTCCGAG ATAATGTGTACAGCATCTTGGCTGTGTGGG | 115. | A_32_P186121 | 5.26 |
| UBE2D3 | NM_181886 | ATATAGCACTGAATAAATGATGCAAGTTGT CAATGGATGAGTGATCAACTAATAGCTCTG | 116. | A_24_P363005 | 6.05 |
| PDLIM3 | NM_014476 | AAACATACACTTAGCTATGTTTTGCAACTC TTTTTGGGGCTAGCAATAATGATATTTAAA | 117. | A_23_P110403 | 4.51 |
| LDB3 | NM_007078 | TTTTTTGCCTGTGTGAATTCTACTTTTTAG CAAAAATAAAGCCCCCCAAAGGATGTGCAA | 118. | A_32_P98227 | 5.11 |
| TTN | NM_133378 | CTGACAACCCTGATCATCATGGACGTACAG AAACAAGATGGTGGACTTTATACCCTGAGT | 119. | A_23_P85269 | 4.66 |
| FHOD1 | NM_013241 | ATCATGGACCTTCTGGTGCAGTCAGTGACC AAGAGCAGTCCTCGTGCCTTAGCTGCTAGG | 120. | A_23_P37778 | 5.46 |
| TBC1D15 | NM_022771 | CAACACAGATACCAGTGTCCTCAGATGTCT GCAGATTAACACCTGCATGATCACTGTTCT | 121. | A_23_P139558 | 5.10 |
| RYR1 | NM_000540 | GAGTCTTATGTCTGGAAGATGTACCAAGAG AGATGTTGGGATTTCTTCCCAGCTGGTGAT | 122. | A_23_P78867 | 4.76 |

TABLE 5-continued

Transcripts mis-spliced in DM1 muscle tissue and other muscle transcripts that are expressed in human serum extracellular RNA (exRNA).

| Gene Name | Systematic name | Sequence | # | Probe Name | Avg |
|---|---|---|---|---|---|
| DTNA | NM_001392 | TCGGACGGTGCTTTTGGTGGATGCGTCTAG ATGGATAACATGACTTCTTCTACCCTAAAA | 123. | A_23_P208158 | 4.82 |
| TNNT2 | NM_000364 | AACAGGAGGAAGGCTGAGGATGAGGCCCGG AAGAAGAAGGCTTTGTCCAACATGATGCAT | 124. | A_23_P34700 | 5.28 |
| FXR1 | NM_001013439 | AGTCTTTACATCGCACTTTCAGTTCCTCCA TTTGGAATTCATAAAGGGGAGGGATCCTGA | 125. | A_23_P132784 | 5.47 |
| CKM | NM_001824 | ACACTCGGAGCTTGTGCTTTGTCTCCACGC AAAGCGATAAATAAAAGCATTGGTGGCCTT | 126. | A_23_P50250 | 4.75 |
| ACTA1 | NM_001100 | CCGCAGTCACTTTCTTTGTAACAACTTCCG TTGCTGCCATCGTAAACTGACACAGTGTTT | 127. | A_23_P1102 | 4.98 |
| MYH3 | NM_002470 | CTAAGACTCGAGACTTCACCTCCAGCAGGA TGGTGGTCCACGAGAGTGAAGAGTGAGCCA | 128. | A_23_P26865 | 4.86 |

Serum samples from healthy control subjects (Ctrl; N = 7) were filtered through an 0.8 µm filter to remove cells, ultracentrifuged at 100,000 x g for 90 minutes to collect extracellular RNA in EVs and particles, and the EV/ribonucleoprotein (RNP) pellet was lysed. RNA was extracted using the Qiagen miRNeasy kit and examined by mRNA microarray analysis. The data are represented as quartile normalized with background subtraction and values indicate expression levels of each gene (Noerholm et al., BMC Cancer 12, 22 (2012)). More than two-dozen transcripts of the mis-spliced mRNAs found in tibialis anterior (TA) muscle tissue of DM1 patients and reported as biomarkers of muscle weakness (Nakamori et al., Ann Neurol 74, 862-872 (2013)) are detected in the serum EV/RNP mRNA fraction and are candidate serum biomarkers. Note the similar levels of expression of muscle transcripts between healthy controls. The presence of muscle transcripts in EVs in this study is Lett 587, 1379-1384 (2013)) and measurement of muscle-enriched miRs in human serum (Aoi et al., Front Physiol 4, 80 (2013)). (*transcripts we report here that show differential urine exRNA splicing in DM1 vs MDC and UA controls; #SEQ ID NO:).

TABLE 6

Screening of human urine exosomes/microvesicles for presence of transcripts that are mis-spliced in DM1 muscle tissue.

| Gene | Normalized | Raw |
|---|---|---|
| DMPK | 2.348005036 | 380 |
| INSR* | 5.410552617 | 2204 |
| SOS1* | 11.78539296 | 4408 |
| MBNL2* | 28.38510805 | 6004 |
| CLASP1* | 10.58959612 | 3876 |
| MBNL1* | 16.93241215 | 4180 |
| MAP3K4* | 22.19040448 | 5472 |
| NFIX* | 80.93189513 | 20292 |
| NCOR2* | 17.48260768 | 6976 |
| VPS39* | 16.7391543 | 3637 |
| MAPT* | 3.968124064 | 1216 |
| KIF13A | 9.413147298 | 2736 |
| DMD | 0.430326742 | 304 |
| CLCN1 | 0 | 0 |
| ATP2A1 | 0 | 0 |
| CAPZB | 184.636637 | 14197 |
| CACNA1S | 0 | 0 |
| CAMK2B | 0.736559261 | 152 |
| COPZ2 | 10.73770858 | 436 |
| GFPT1 | 29.71567389 | 11546 |
| IMPDH2 | 72.96428986 | 5548 |
| ALPK3 | 1.393280124 | 684 |
| ANK2 | 3.375451832 | 2204 |
| ARFGAP2 | 30.19114602 | 3641 |
| BIN1 | 13.30854948 | 1596 |
| NRAP | 0 | 0 |
| OPA1 | 15.35810568 | 4484 |
| PHKA1 | 6.584110353 | 1824 |
| PHKA2 | 3.110806445 | 698 |
| UBE2D3 | 53.16414472 | 6947 |
| PDLIM3 | 0 | 0 |
| LDB3 | 0.25908561 | 76 |
| TTN | 0.166126138 | 836 |
| FHOD1 | 1.754220849 | 304 |
| TBC1D15 | 7.176337802 | 1900 |
| RYR1 | 0 | 0 |
| DTNA | 0.315128162 | 152 |
| TNNT2 | 1.443318118 | 76 |
| FXR1 | 13.46978301 | 5396 |
| LMNA | 55.02644764 | 8284 |
| MLF1 | 1.303656519 | 152 |
| ABLIM2 | 0.699642342 | 152 |
| CKM | 0 | 0 |
| ACTA1 | 0 | 0 |
| MYH3 | 0.561759871 | 152 |

A previous study collected 3300 ml of urine from a human male, centrifuged the entire volume at low speed to pellet cells, passed the supernatant through a 0.8 µm filter to remove remaining debris, ultracentrifuged the filtered supernatant, isolated RNA from the exosome/microvesicle pellet using a commercially available kit (Qiagen), and identified genes present using massively parallel RNA sequencing (Miranda et al., PLoS One 9, e96094 (2014)). Shown are raw and normalized counts of genes from that study that also were reported as biomarkers of DM1 in muscle biopsies 5, as well as other genes associated with muscular dystrophies.
(*transcripts we report here that show differential urine exRNA splicing in DM1 vs MDC and UA controls).

Figure 1B:
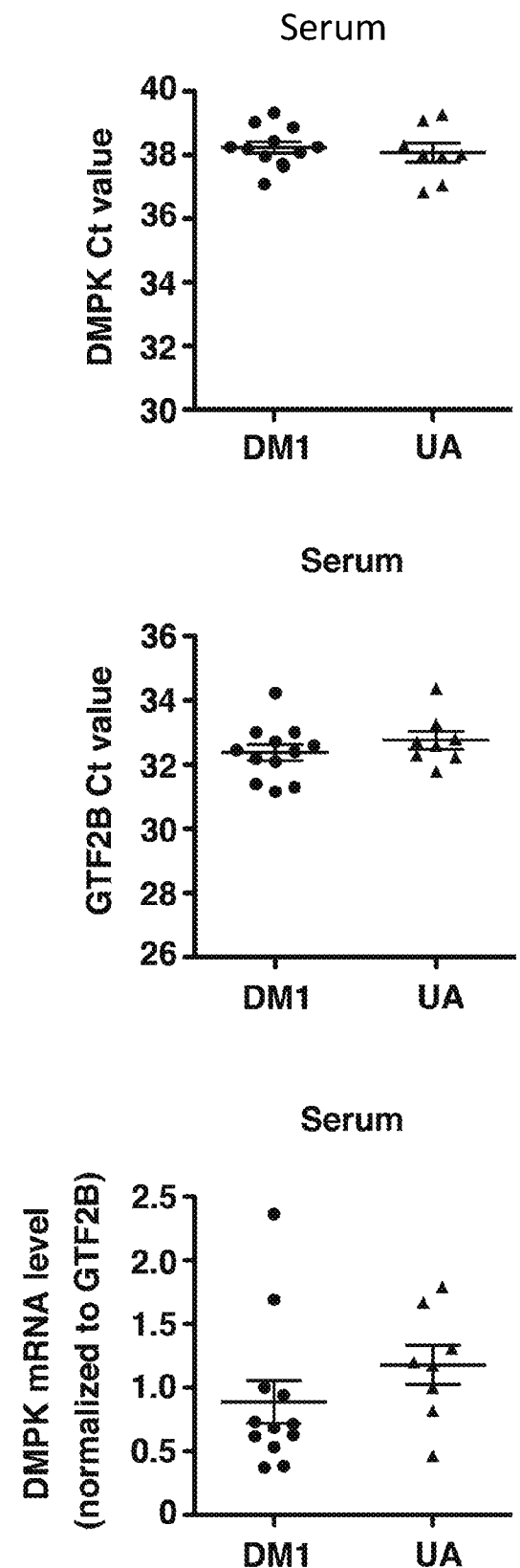
Figure 2A:
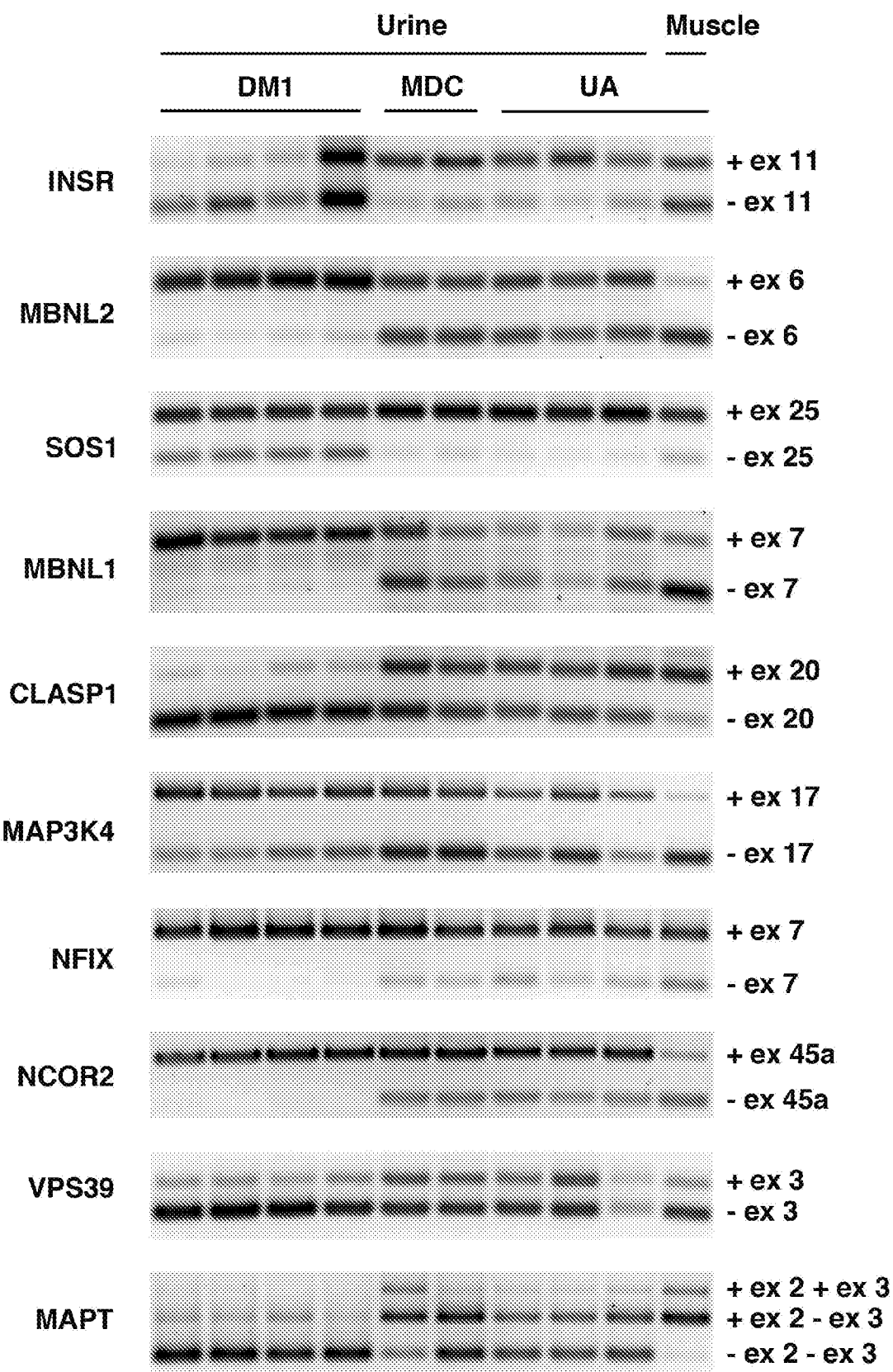
FIGS. 2A-C. mRNA alternative splicing in exRNA from human urine. We isolated urine exRNA from 27 DM1, 14 DMD/BMD controls (MDC), and 26 unaffected (UA) subjects, and examined alternative splicing by RT-PCR and gel electrophoresis.[4] (A) Representative gel images showing alterative splicing of human insulin receptor (INSR) exon 11, MBNL2 exon 6, SOS1 exon 25, MBNL1 exon 7, CLASP1 exon 20, MAP3K4 exon 17, NFIX exon 7, NCOR2 exon 45a, VPS39 exon 3, and MAPT exons 2 and 3. PCR cycle number was 36 (INSR, MBNL2, SOS1, CLASP1, MAP3K4, NFIX, NCOR2, VPS39) or 37 (MBNL1, MAPT). Control muscle cDNA was diluted 1:50 (MAPT) or 1:100 (INSR, MBNL2, SOS1, MBNL1, CLASP1, MAP3K4, NFIX, NCOR2, VPS39) and amplified in the same PCR reaction as urine samples. (B, C) Individual data points represent quantitation of splicing of all individual urine samples examined. Error bars=mean±s.e.m. ** $P<0.0001$ (1-way ANOVA); =mean difference 9.4, 95% CI of difference 2.9 to 15.9.
Figure 2B:
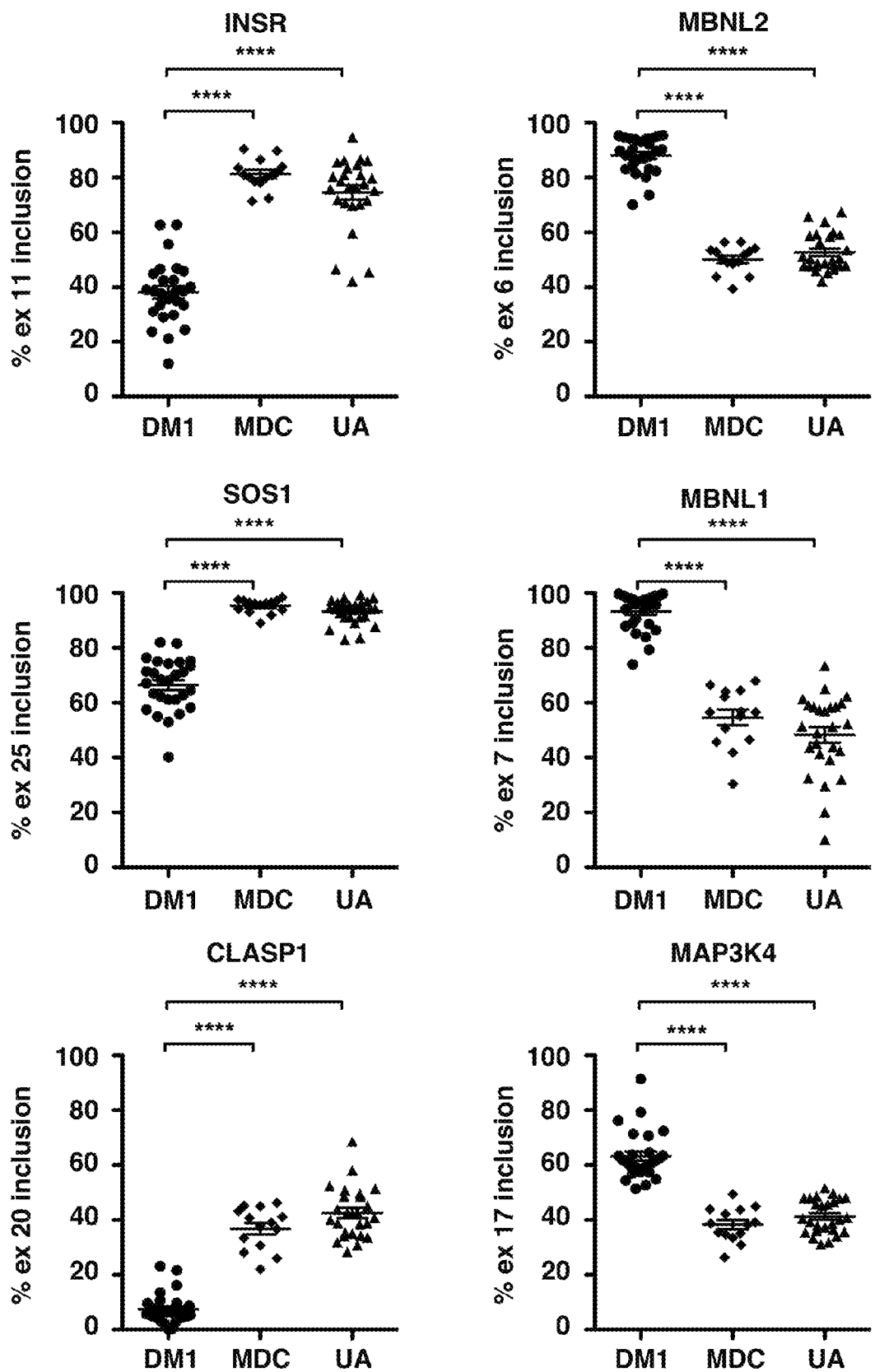
Figure 2C:
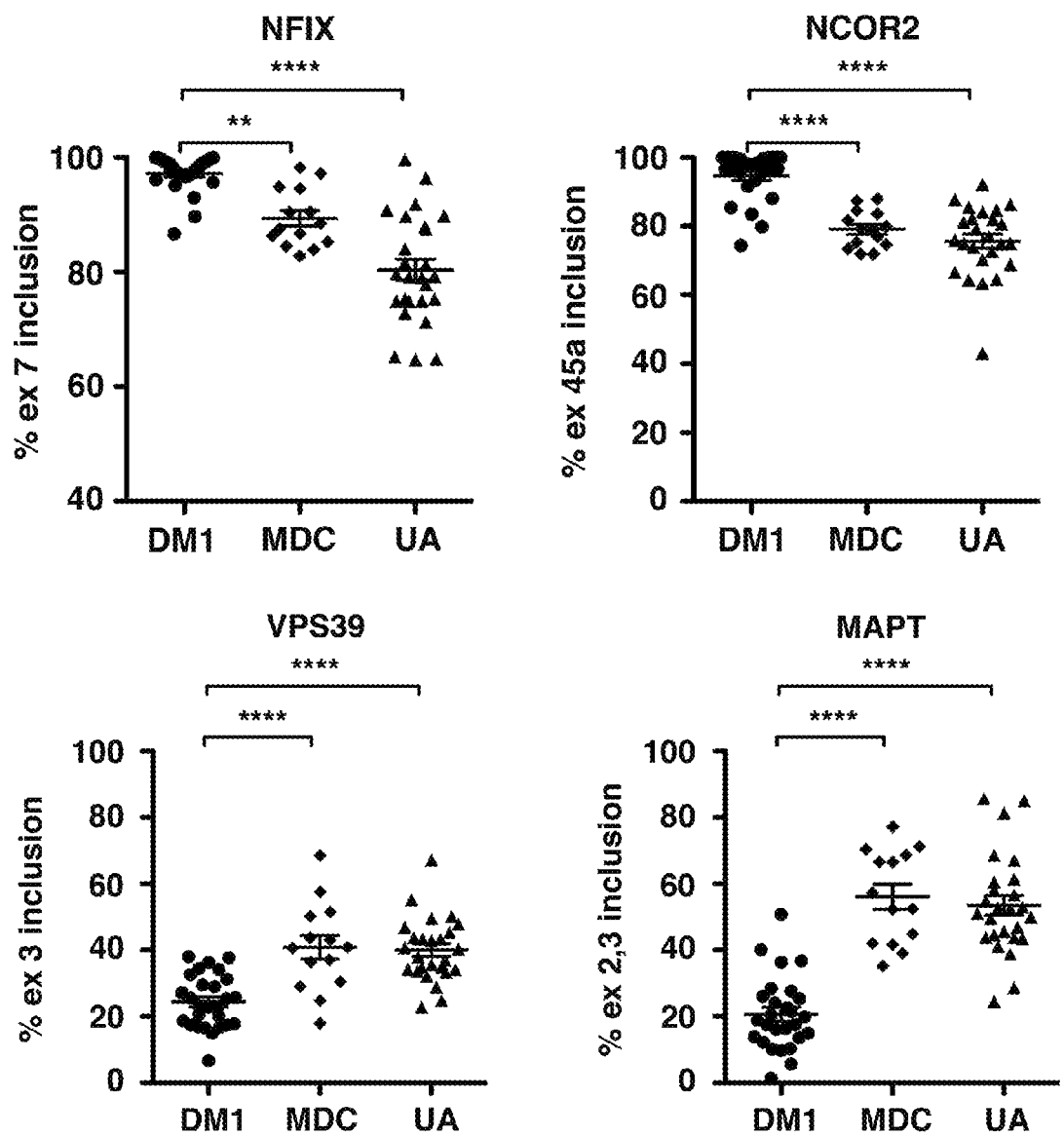
Figure 7G:
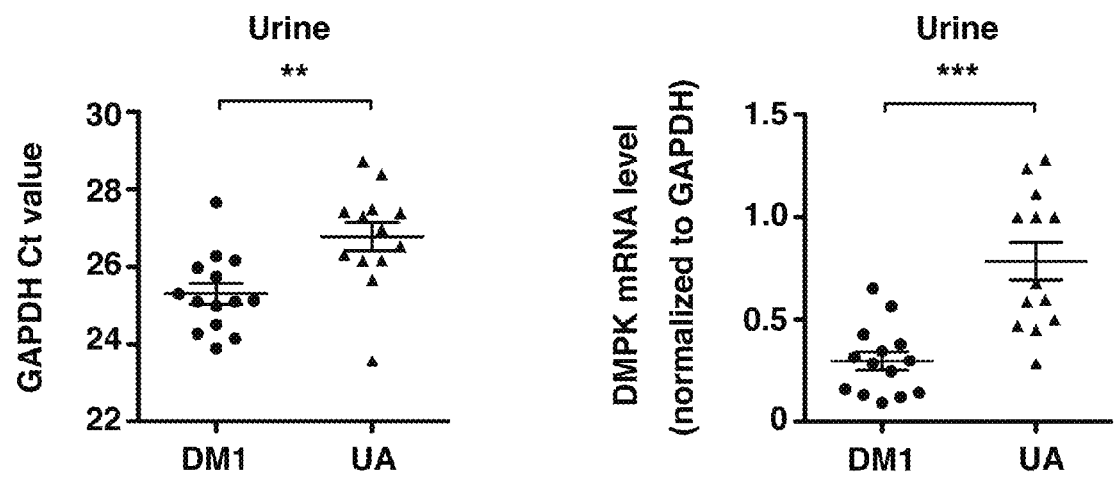
Figure 7H:
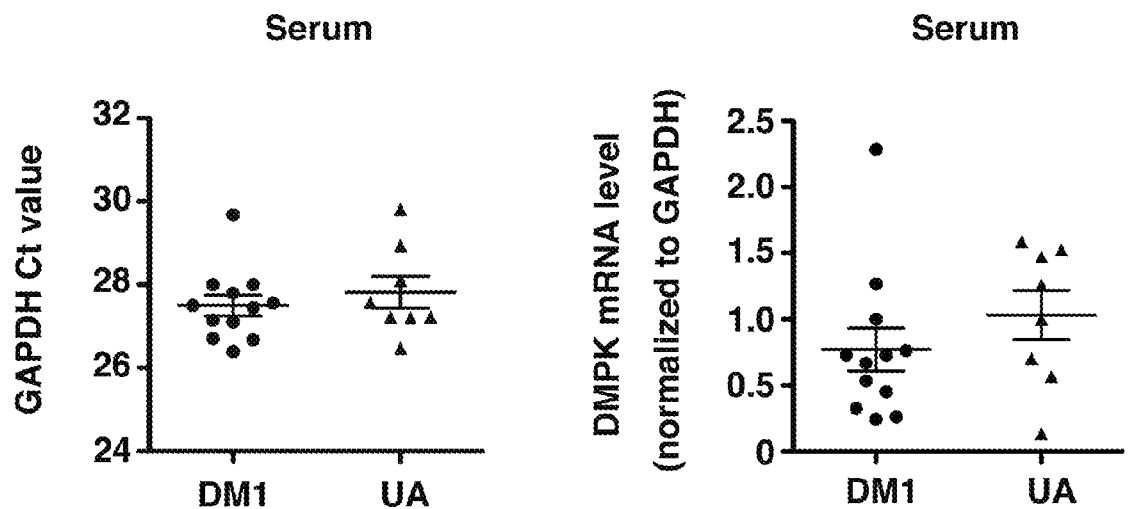

Example 2. Quantitative Gene Expression in Biofluids from DM1 and UA Subjects Based on qPCR cycle threshold (Ct) values of reference genes GTF2B and GAPDH, urine ex-mRNA content tended to be higher in DM1 as compared to UA subjects (FIG. 1A and FIG. 7G). The lower expression of DMPK, the gene causing DM1, in urine from DM1 vs. UA subjects may be due to retention of mutant transcripts in the nucleus preventing their release into the cytoplasm and incorporation into EVs[22]. In serum, these transcripts were expressed at similar levels in both DM1 and UA subjects, and were present at lower levels than in urine (FIG. 1B and FIG. 7H).

Figure 3A:
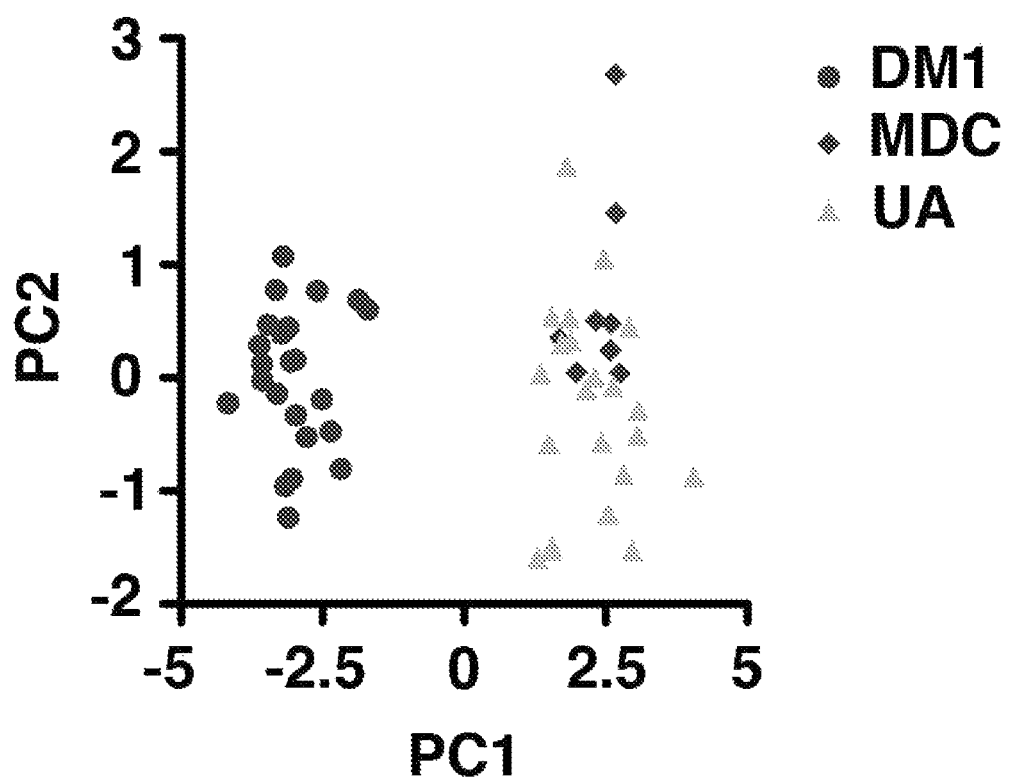
FIGS. 3A-C. Principle component analysis and predictive modeling of urine splicing outcomes. Using principal component regression, a linear combination of 10 urine transcripts that show differential splicing in DM1 subjects (INSR, MBNL2, SOS1, MBNL1, CLASP1, MAP3K4, NFIX, NCOR2, VPS39, and MAPT) was used to develop a predictive model of DM1. (A) Principle component (PC) score for each subject (N=23 DM1, 8 MDC, 22 UA). (B) DM1 (N=23) and UA (N=22) subjects were combined (N=45 total), then 34 randomly assigned, irrespective of genotype, to a training set that was used to generate a predictive model of urine splicing outcomes. Using a singular value decomposition algorithm for the fitting and a threshold of 0.5 (see Methods), the model produced zero false positives and false negatives in a 5-fold cross-validation test. The Receiver Operating Characteristic (ROC) curve is shown. (C) The remaining 11 subjects, plus an additional 8 subjects examined while blinded to genotype (N=19 total), formed an independent validation set that produced zero false positives and false negatives.
Figures 3B, 3C:
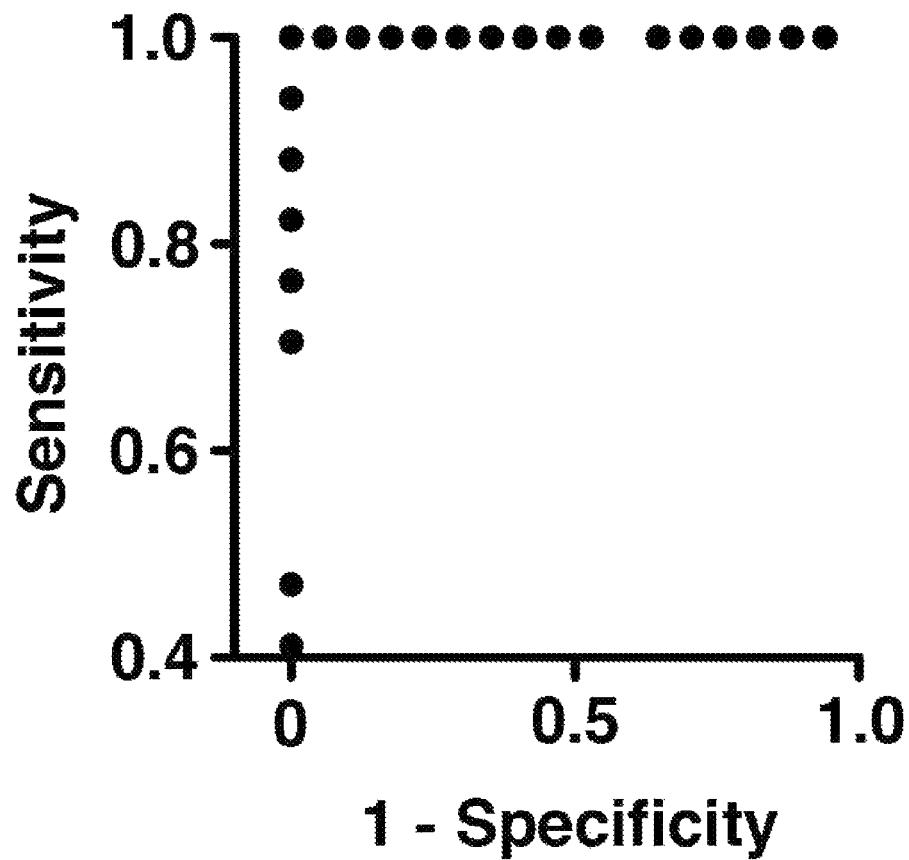
Figure 4A:
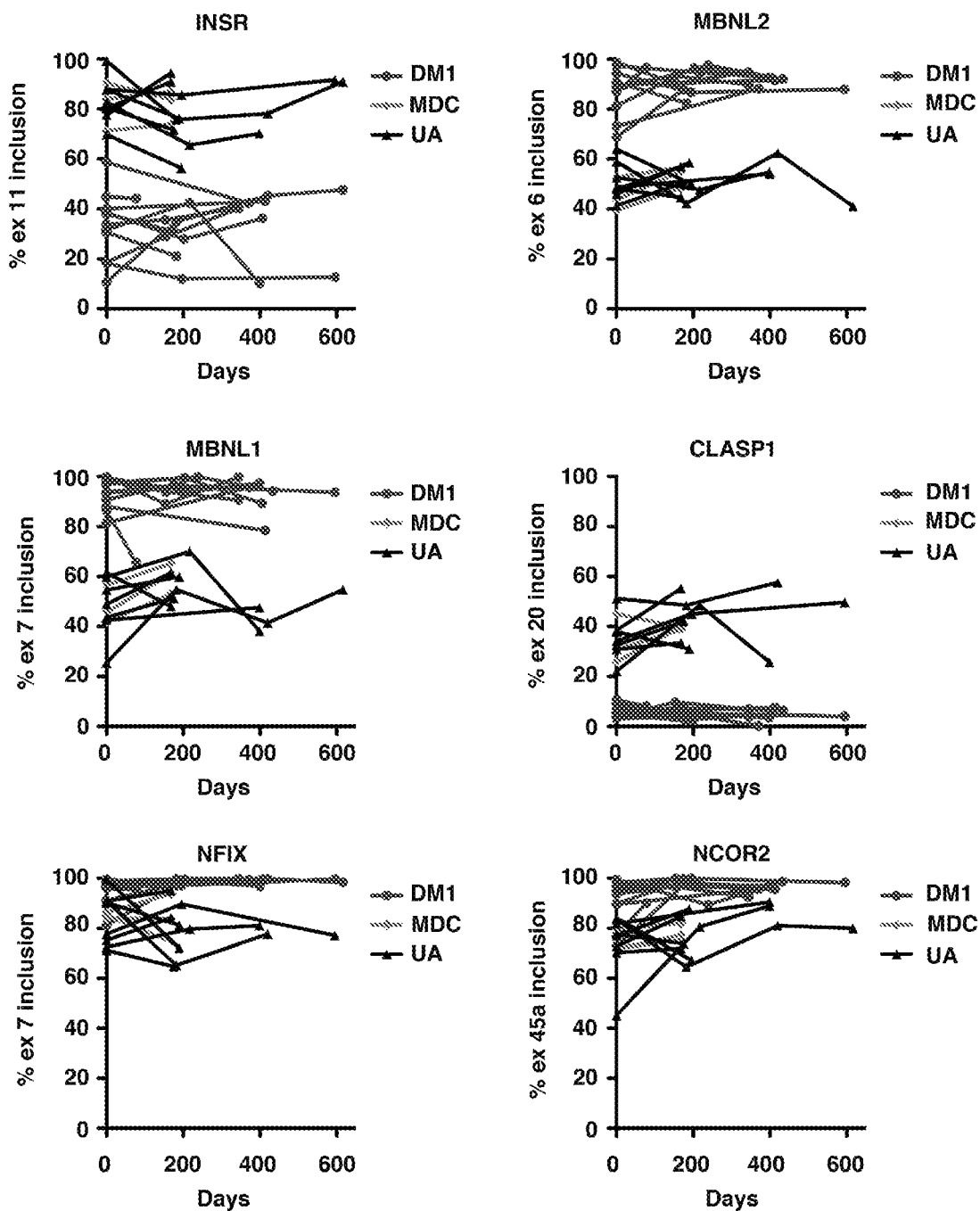
FIGS. 4A-C. Reliability of exRNA alternative splicing outcomes in human urine. We collected separate urine specimens from 12 DM1, 4 MDC, and 10 UA subjects several months apart and examined exRNA splicing outcomes by RT-PCR. Note that due to low collection volume in one of the UA specimens, 8 of the 10 transcripts have replicates from only 9 UA specimens.
Figure 4B:
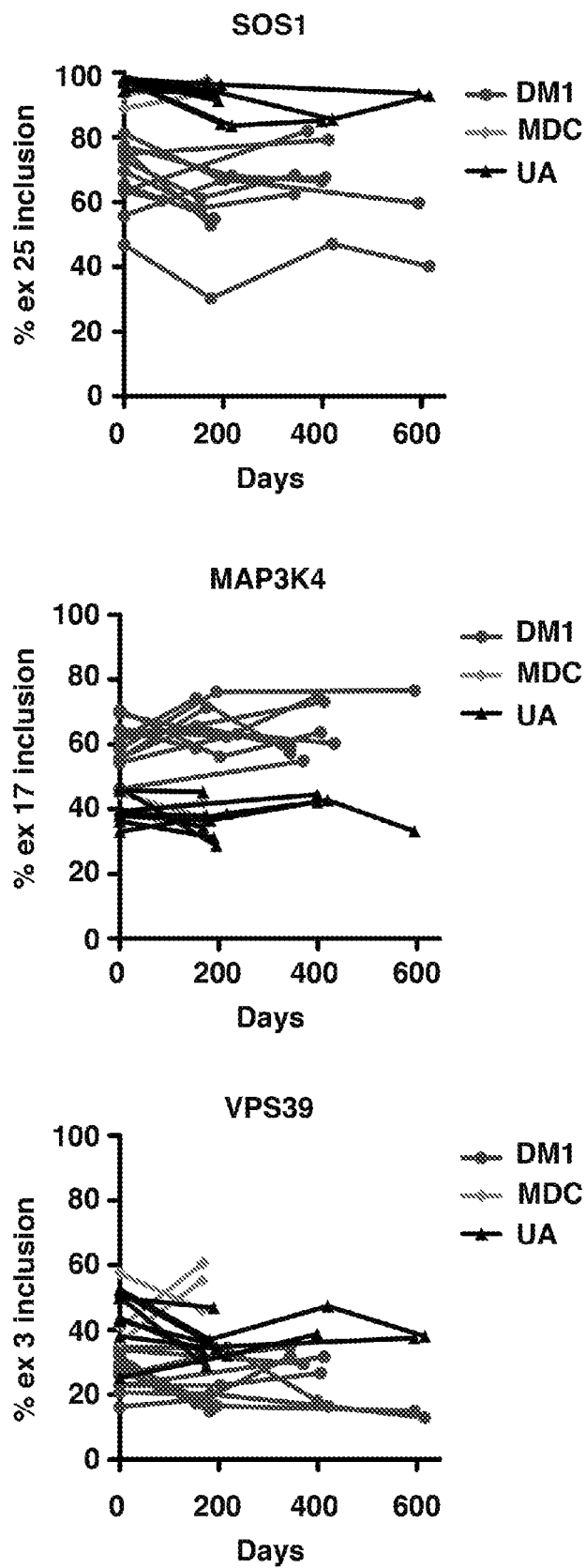
Figure 4C:
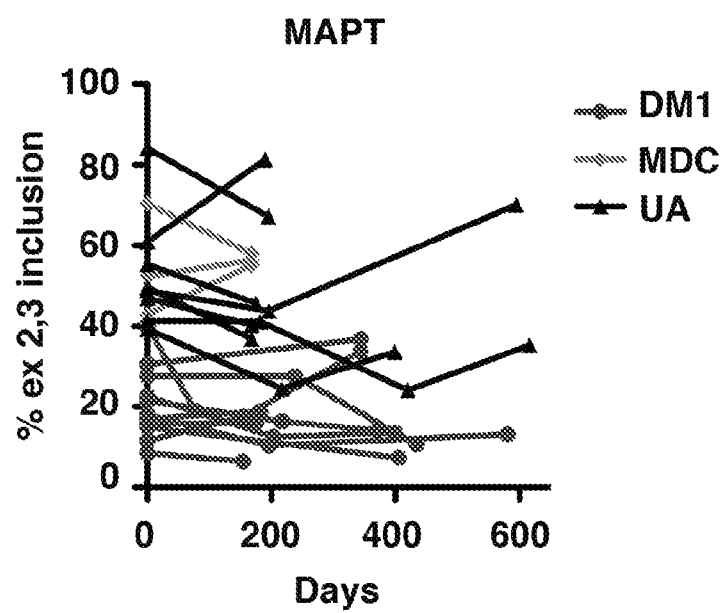
Figure 5A:
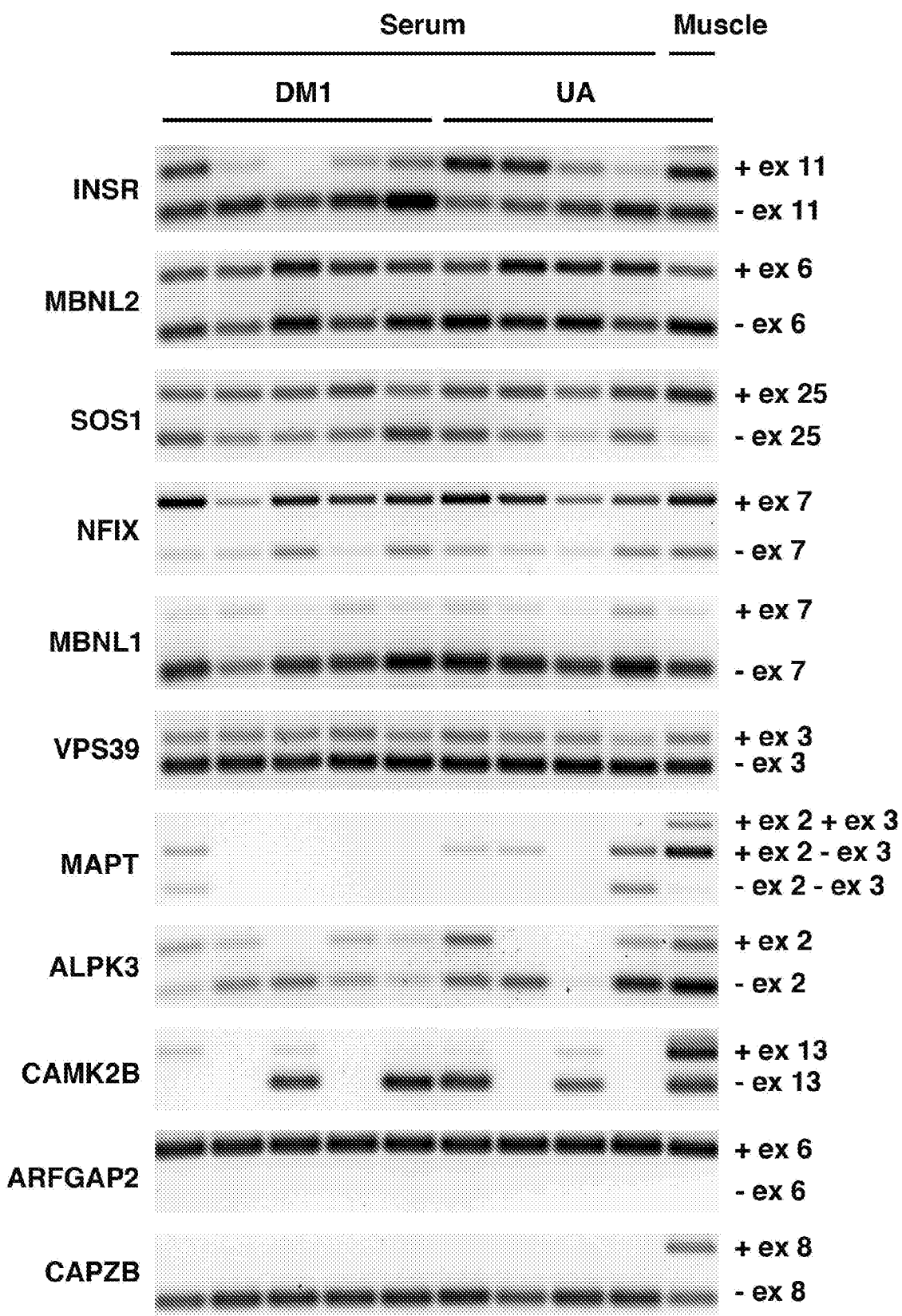
FIGS. 5A-B. Alternative splicing of exRNA in human serum. (A) We used RT-PCR to screen splicing in DM1 (N=5) and UA control (N=4) serum exRNA samples of several transcripts mis-spliced in DM1 muscle biopsies.[28] Splicing in normal human muscle tissue served as a control. Transcript name is shown on the left and target exon/intron on the right. PCR cycle number was 36 (VPS39, CAPZB) or 40 (MBNL1, MAPT, CAMK2B, ARFGAP2, ALPK3). Examination of VPS39 in an additional 9 DM1 and 7 UA samples and ALPK3 in an additional 4 DM1 and 3 UA samples also showed no difference in splicing patterns by genotype. Alternative splicing patterns in serum appeared similar in DM1 and UA for all transcripts tested. (B) Alternative splicing by RT-PCR and gel electrophoresis of INSR exon 11 (N=14 DM1, 10 UA), MBNL2 exon 6 (N=9 DM1, 9 UA), SOS1 exon 25 (N=14 DM1, 12 UA), and NFIX exon 7 (N=14 DM1, 12 UA) in human serum exRNA. PCR cycle number was 36 (MBNL2, SOS1, NFIX), and 40 (INSR). Control muscle cDNA was diluted 1:100 and amplified in the same PCR reaction as serum samples. Individual data points represent quantitation of splicing of all serum samples examined. Error bars=mean±s.e.m.
Figure 5B:
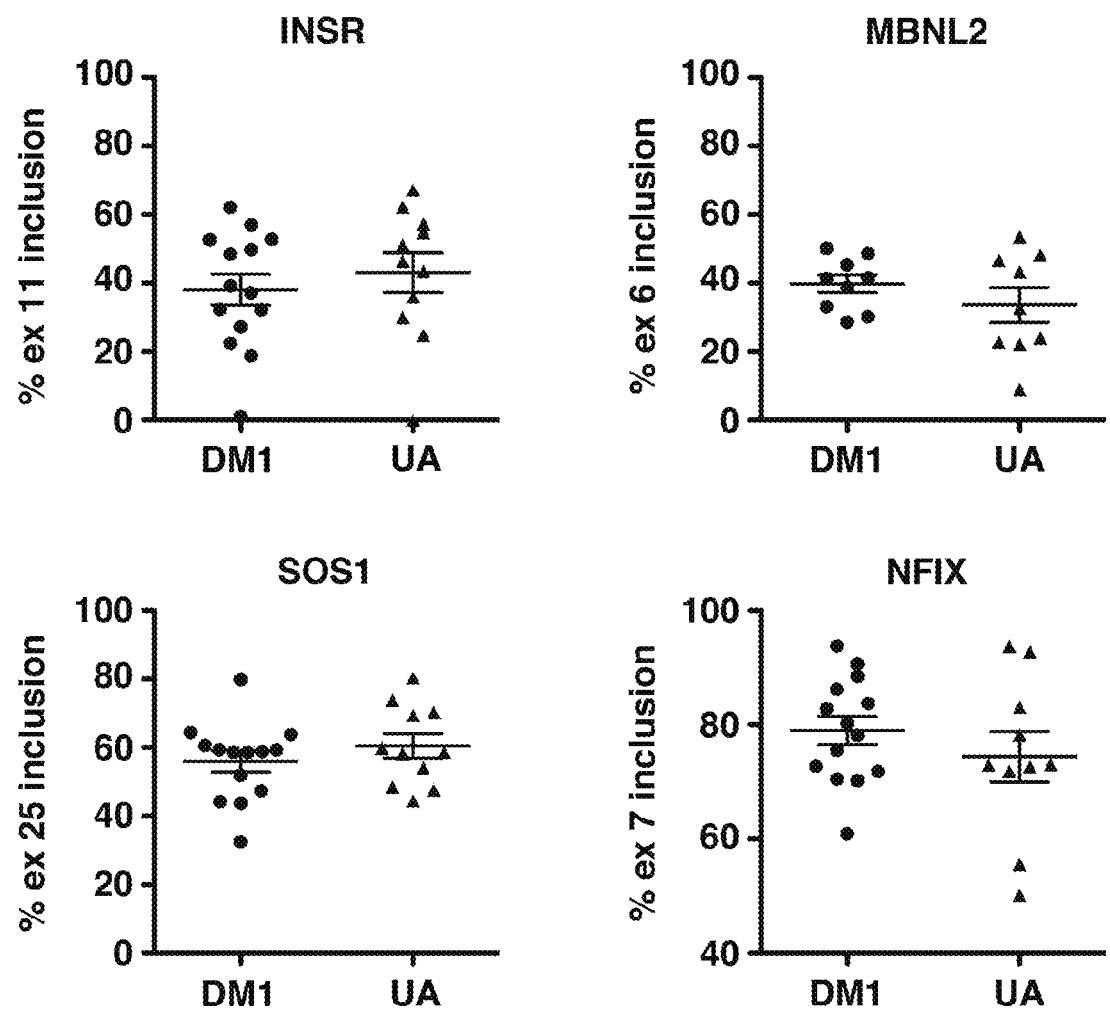
Figure 8A:
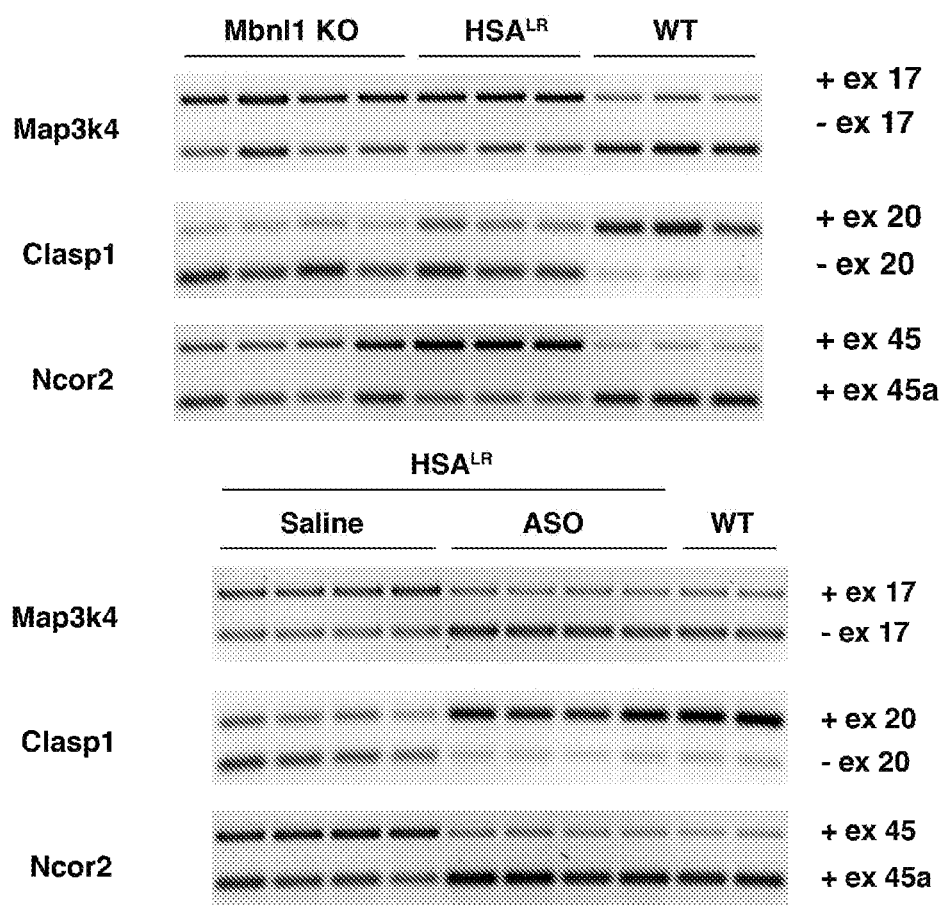
FIGS. 8A-B. Regulation of Map3k4, Clasp1, and Ncor2 splicing by MBNL1 protein and response to ASO treatment. (A) We used RT-PCR to analyze alternative splicing of Map3k4, Clasp1, and Ncor2 in gastrocnemius muscles from 2 mouse models of DM1, the Mbnl1 knockout (Kanadia et al., Science 302, 1978-1980 (2003)) (Mbnl1$^{ΔE3/ΔE3}$; N=4) and HSA$^{LR}$ transgenic (Mankodi et al., Science 289, 1769-1773 (2000)) (N=3), and FVB wild-type (N=3). The graph shows quantitation of alternative exon 17 splicing in each individual replicate. ** P<0.0001 (1-way ANOVA). (B) We treated HSA$^{LR}$ with either saline or ASO 445236 (Wheeler et al., Nature 488, 111-115 (2012)) (N=4 each) using a dose of 25 mg/kg twice weekly for 4 weeks, and analyzed alternative splicing in quadriceps muscles from these mice by RT-PCR. Gastrocnemius muscles from untreated FVB wild type (N=2) served as controls. The graph shows quantitation of alternative exon 17 splicing in each individual replicate. ** P<0.0001 (1-way ANOVA). These data demonstrate that alternative splicing of Map3k4 is regulated by Mbnl1 protein and that mis-splicing of Map3k4 in the HSA$^{LR}$ mouse model of DM1 is rescued by ASO treatment, similar to ASO rescue of other alternatively spliced exons that are regulated by MBNL1 protein.
Figure 8B:
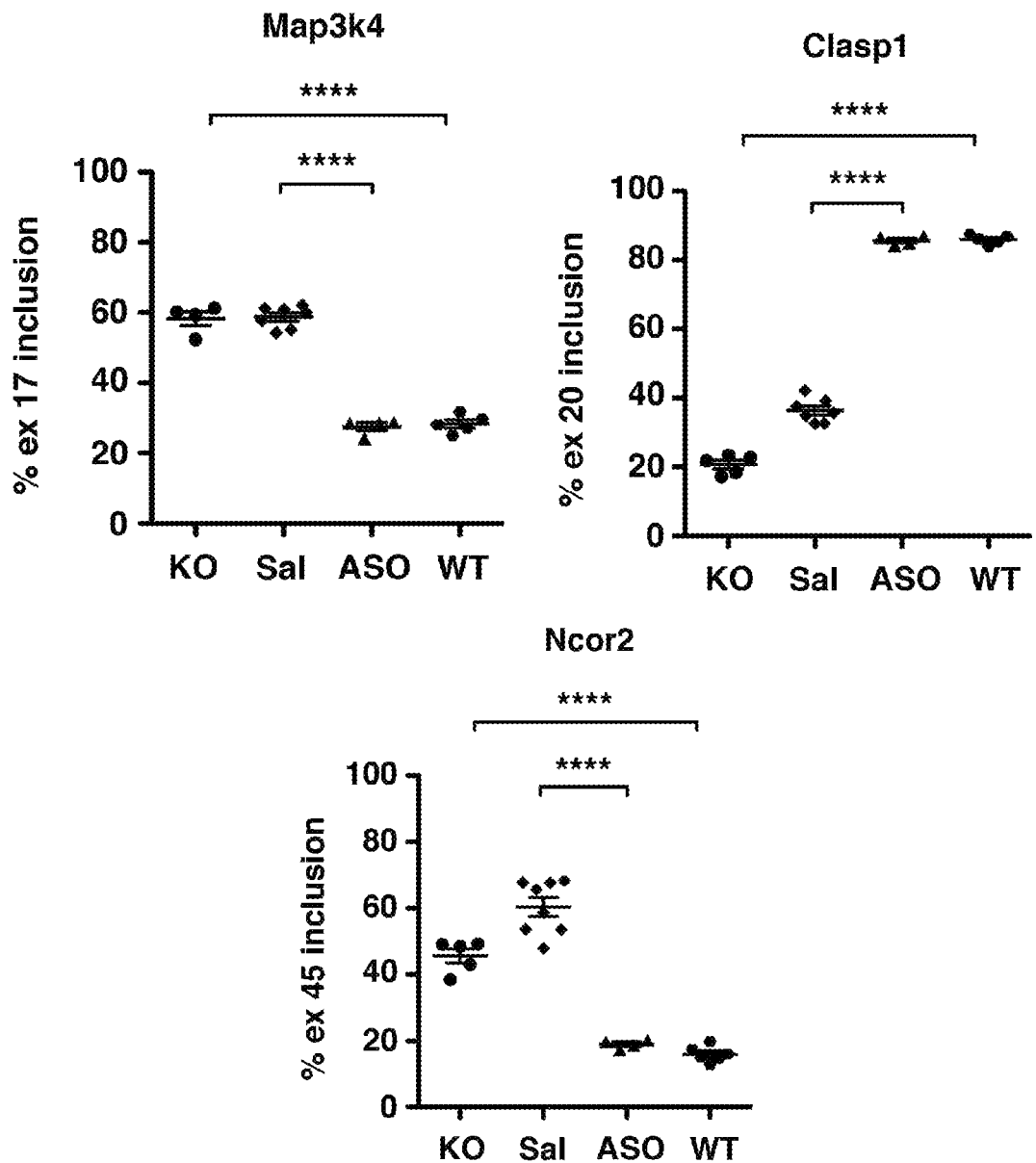
Figure 9A:
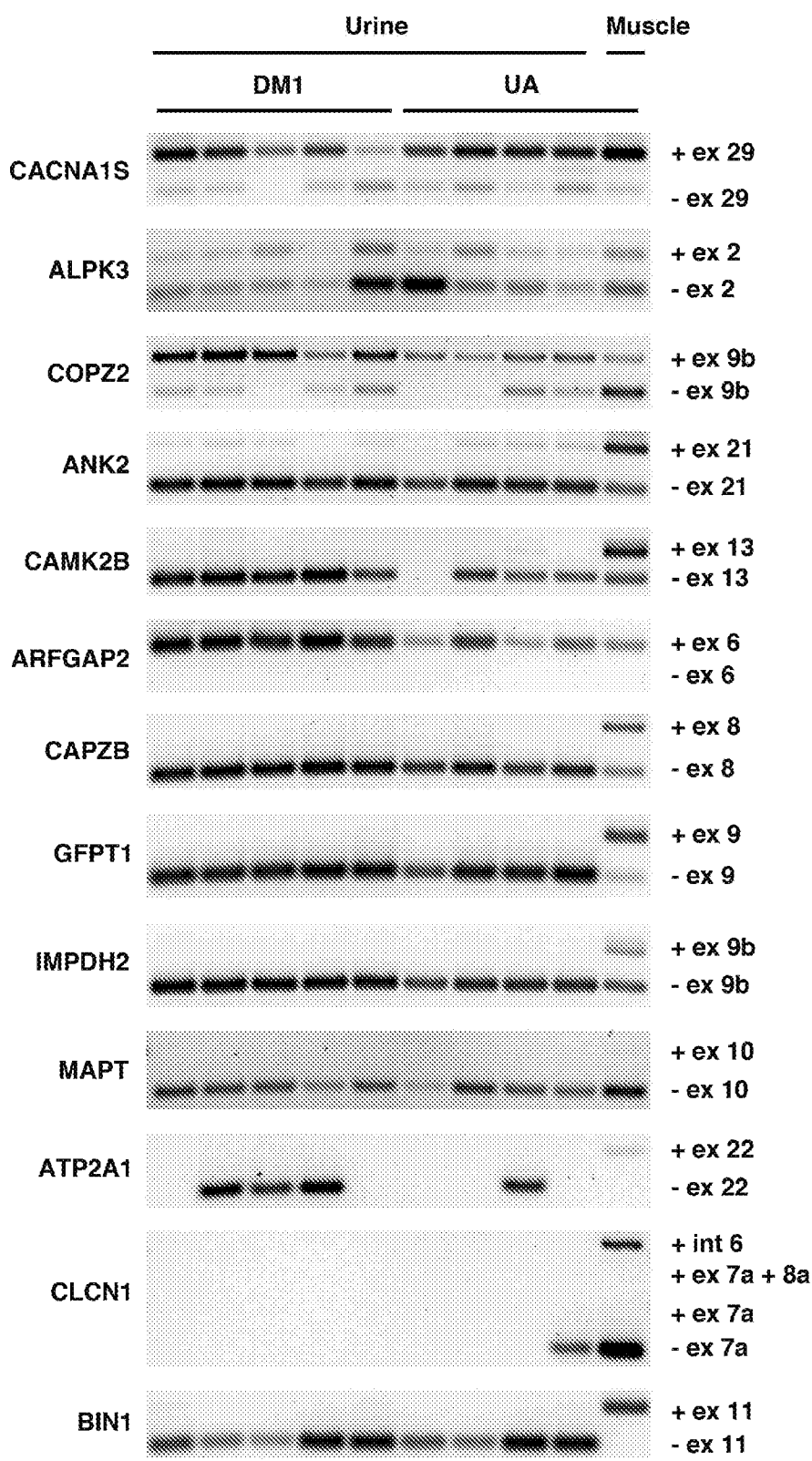
FIGS. 9A-C. Alternative splicing in urine exRNA isolated from DM1 and unaffected subjects. (A,B) We used RT-PCR to screen 23 candidate DM mis-regulated splice events (Nakamori et al., Ann Neurol 74, 862-872 (2013)) in urine exRNA from DM1 (N=5) and UA control (N=4) subjects. Splicing in normal muscle tissue served as a control. Transcript name is shown on the left and target exon/intron on the right. PCR cycle number was 34 (ARFGAP2), 36 (CACNA1S, ALPK3, COPZ2, ANK2, CAPZB, GFPT1, IMPDH2, MAPT, BIN1, FN1, NRAP, OPA1, PHKA1, UBE2D3), and 40 (CAMK2B, ATP2A1, CLCN1, KIF13A, DMD, LMNA). ALPK3 band intensity was variable, requiring 40 cycles to identify bands in an additional 7 DM1 and 4 UA samples (not shown). Splicing of CAMK2B, ARFGAP2, and CAPZB in an additional 5 DM1 and 3 UA control samples was identical to samples shown above. We detected the ATP2A1 exon 22 exclusion band in 6/8 DM1 samples and 2/7 UA controls. (C) Quantitation of alternative splicing by RT-PCR of KIF13A and DMD in DM1 (N=14), MDC (N=6 or 5), and UA (N=14 or 12) subjects. Note that KIF13A bands were absent in 1 DM1 and 4 UA subjects. Error bars=s.e.m.
Figure 9B:
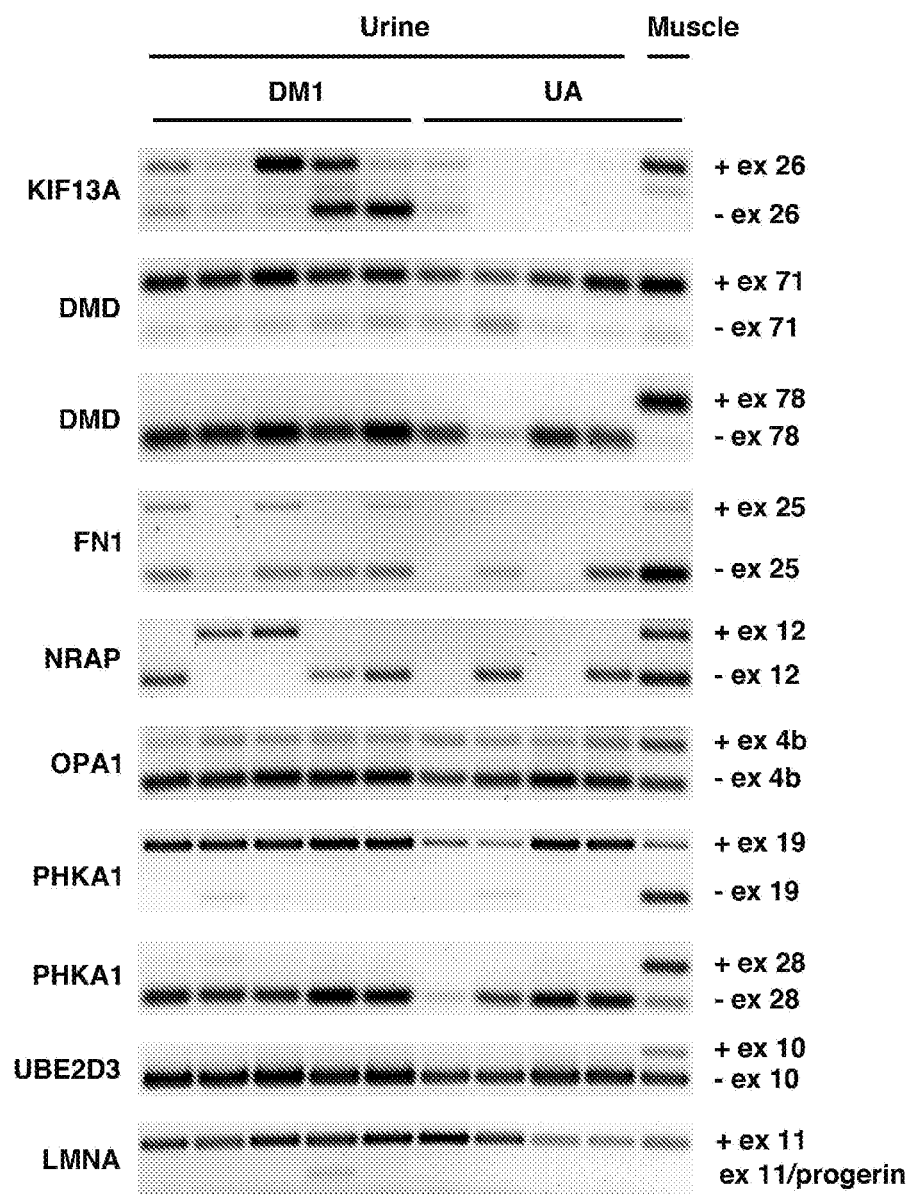
Figure 9C:
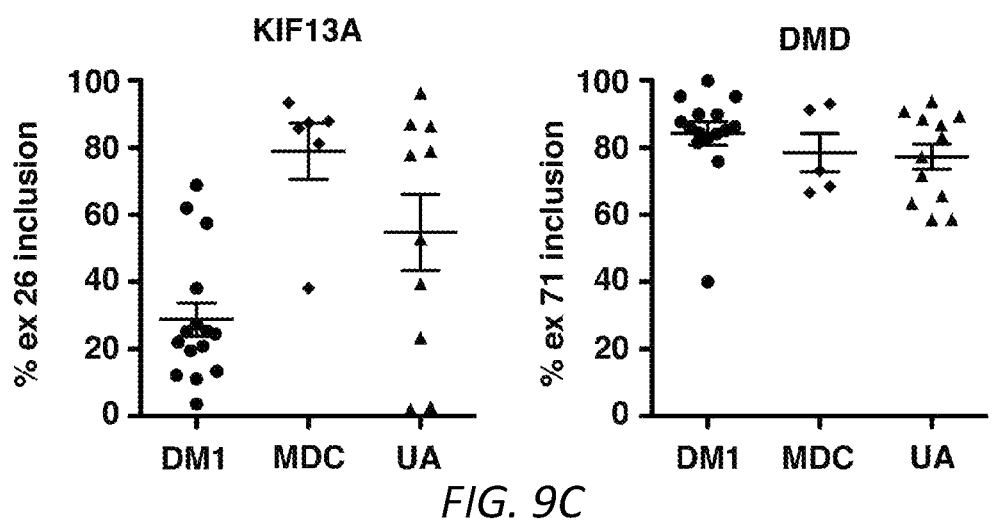
Figure 10A:
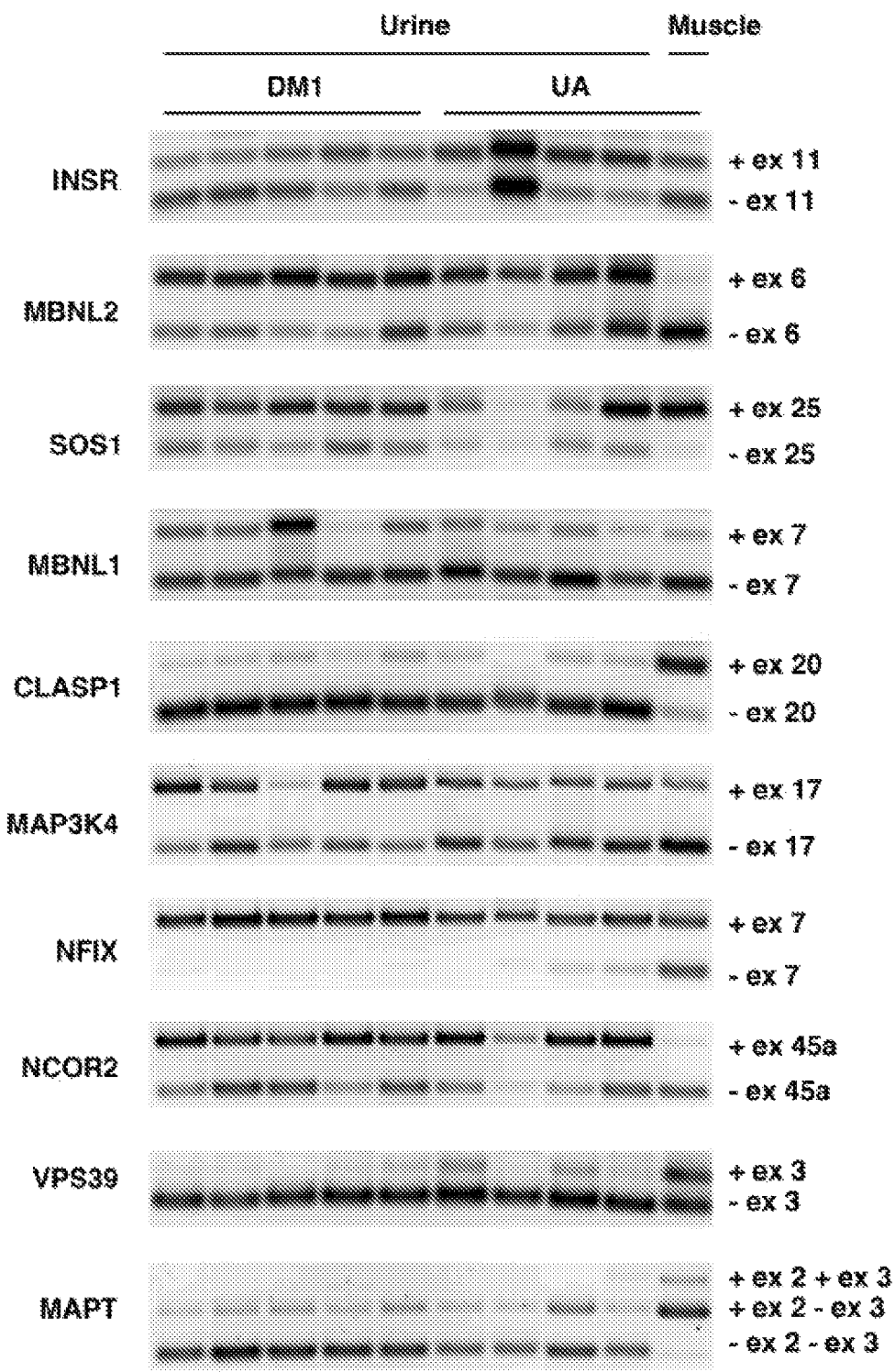
FIGS. 10A-B. Alternative splicing in urine cell pellet RNA isolated from DM1 and unaffected subjects. We isolated total RNA from urine cell pellets obtained from DM1 (N=9), MDC (N=4), and UA (N=9) subjects and analyzed alternative splicing by RT-PCR and gel electrophoresis. (A) Representative gel images showing alterative splicing of human insulin receptor (INSR) exon 11, MBNL2 exon 6, SOS1 exon 25, MBNL1 exon 7, CLASP1 exon 20, MAP3K4 exon 17, NFIX exon 7, NCOR2 exon 45a, VPS39 exon 3, and MAPT exons 2 and 3. PCR cycle number was 36 (INSR, MBNL2, SOS1, CLASP1, MAP3K4, NFIX, NCOR2, VPS39) or 37 (MBNL1, MAPT). Control muscle cDNA was diluted 1:50 (MAPT) or 1:100 (INSR, MBNL2, SOS1, MBNL1, CLASP1, MAP3K4, NFIX, NCOR2, VPS39) and amplified in the same PCR reaction as urine samples. (B) Individual data points represent quantitation of splicing of all individual urine samples examined. **=mean difference 28.1, 95% CI of difference 11.08 to 45.14; *=mean difference 15.33, 95% CI of difference 1.973 to 28.69 (MBNL2) and mean difference 21.61, 95% CI of difference 3.807 to 39.41 (NCOR2).
Figure 10B:
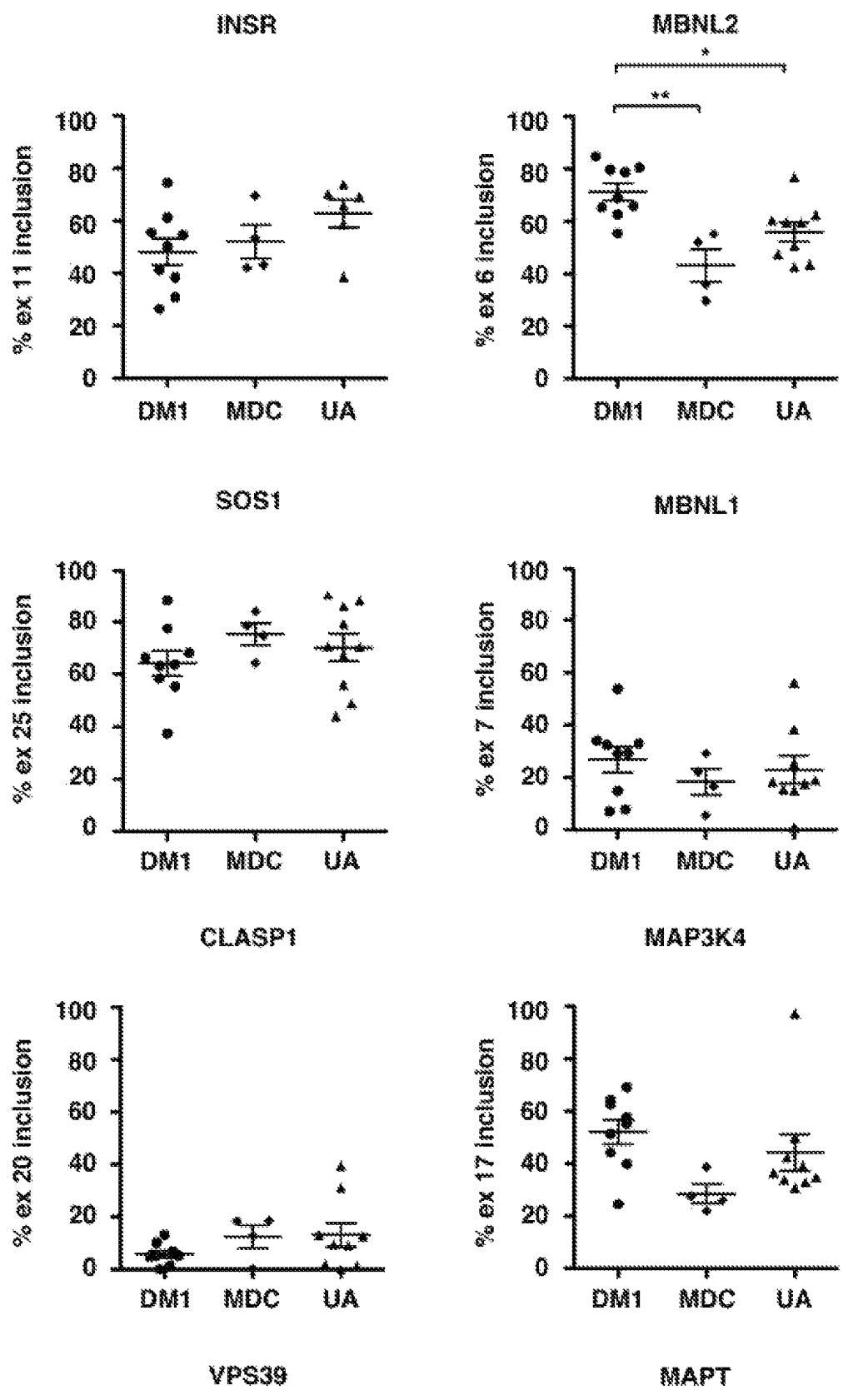
Figure 11A:
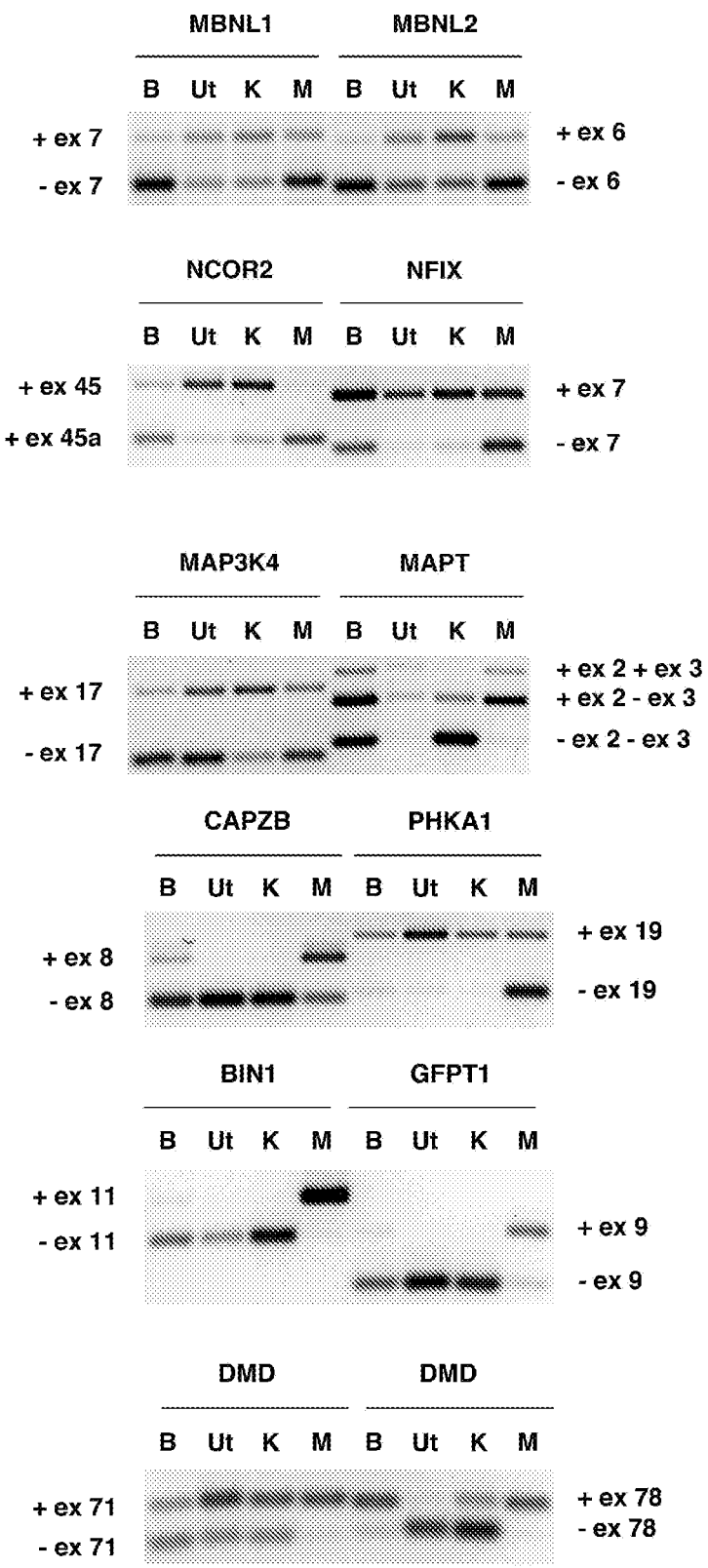

Example 3. Alternative mRNA Splice Variants in exRNA and Urinary Tract Tissues Next we examined splice products in exRNA, focusing on transcripts previously reported as biomarkers of DM1 disease severity in muscle biopsies[4]. In urine exRNA, we identified 10 candidate DM1-specific splice products of 32 examined (FIG. 2), 9 of which are MBNL1 protein-dependent (FIGS. 8A-B)[4, 23]. Principle component analysis of these 10 splicing outcomes confirmed separation of DM1 from MDC and UA individuals (FIG. 3A). We randomly assigned 76% of urine specimens from DM1 and UA subjects regardless of genotype to a training cohort and generated a predictive model that was 100% accurate in identifying the outcome of the remaining 24% of individuals in the validation cohort (FIGS. 3B and C). Splice products appeared similar in consecutive samples collected several months apart from the same individual (FIG. 4), suggesting reliability of the assay. Interestingly, splicing of several other candidate DM mis-regulated splice events[4] was similar in urine from DM1 and UA individuals (FIGS. 9A-9C). Surprisingly, examination of these splice products in serum exRNA failed to show a significant difference between DM1 and UA controls for any of the transcripts examined (FIGS. 5A and B).

Figure 12B:
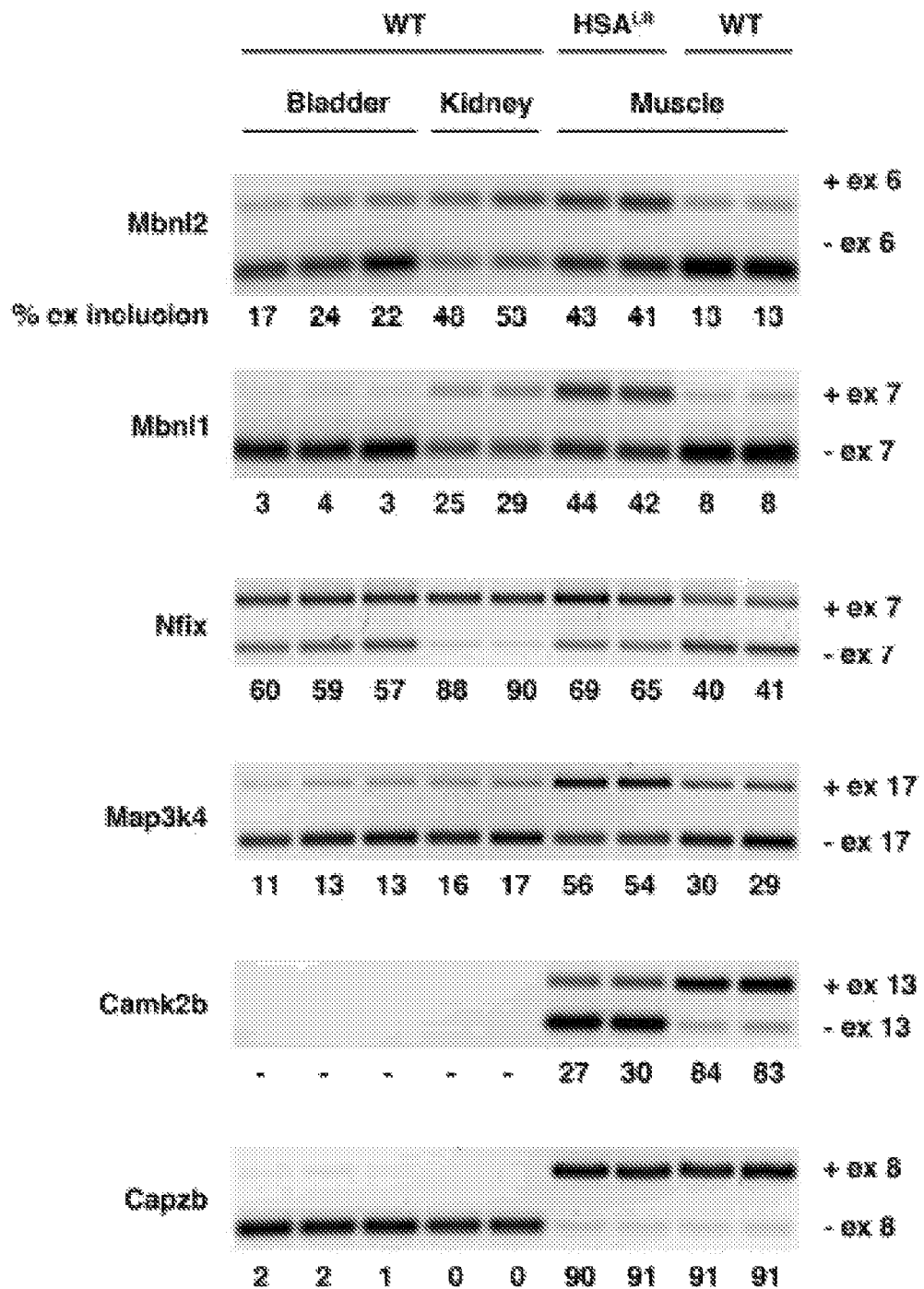
Figure 12C:
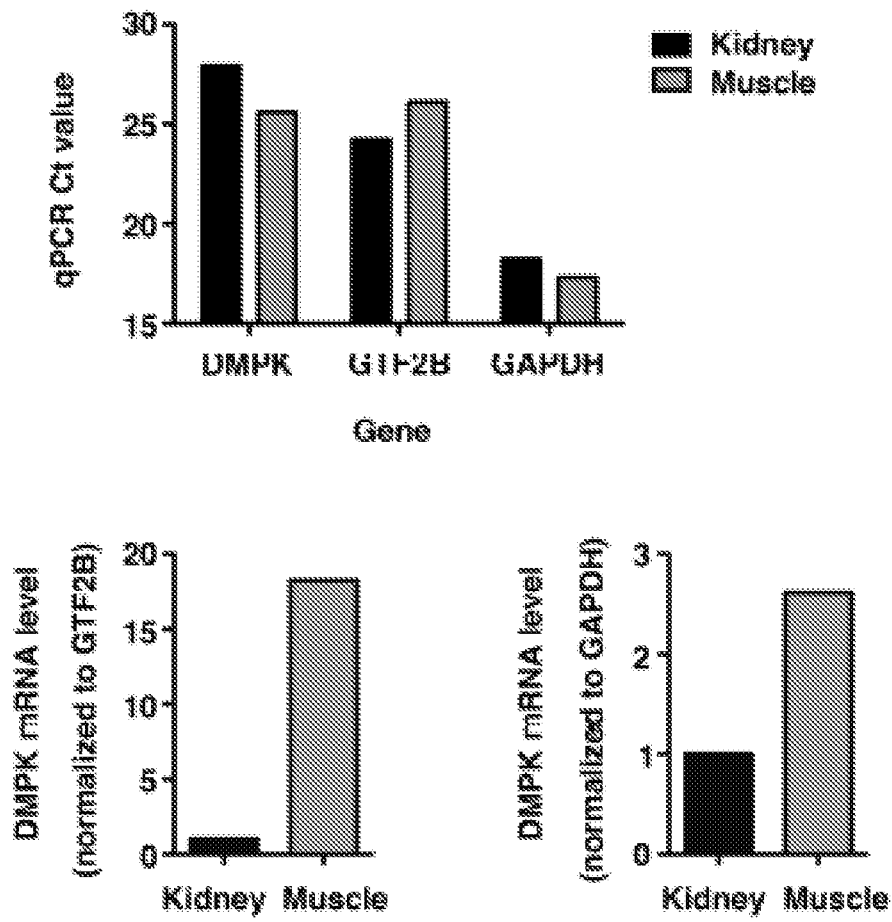
Figure 12D:
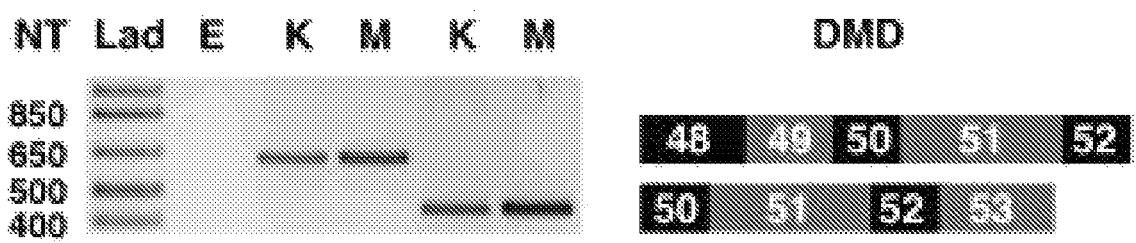

In previous studies, RNAs in urine have been used as biomarkers of prostate cancer, bladder cancer, and kidney transplant rejection, suggesting that cells lining the urinary tract are the primary contributors to the urine ex-RNA pool[12, 24, 25]. Our finding of slightly different exon inclusion/exclusion percentages of some transcripts in urine as compared to muscle tissue suggests the exRNA found in urine may represent a pool from multiple different cell types along this urinary route. To determine whether the urinary tract is the primary contributor of the ex-mRNA alternative splice variants in urine, we examined splice isoforms in human and mouse kidney and mouse bladder (FIGS. 10 and 12). Splicing of all transcripts examined showed different exon inclusion/exclusion percentages in normal human kidney compared to skeletal muscle (FIGS. 10 and 12A). In wild-type mouse bladder and kidney, splicing showed no consistent pattern relative to muscle tissue from wild-type or the $HSA^{LR}$ mouse model of DM1 (FIG. 12B)[26]. qPCR analysis also revealed that kidney expresses DMPK, although at a lower level than muscle (FIG. 12C).

Example 4. Personalized DMD Deletion Transcripts in Human Urine

Figure 6A:
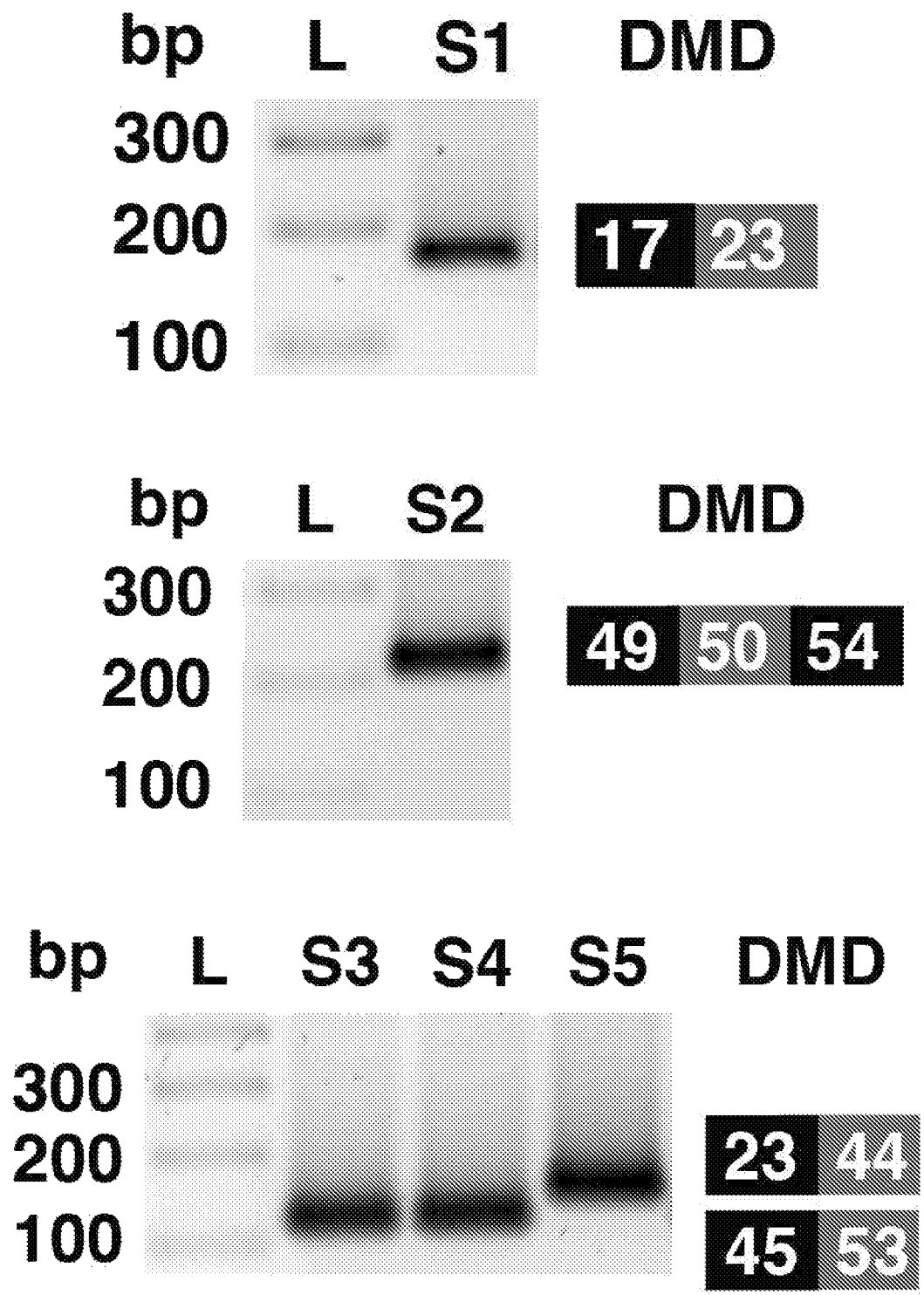
Figure 6B:
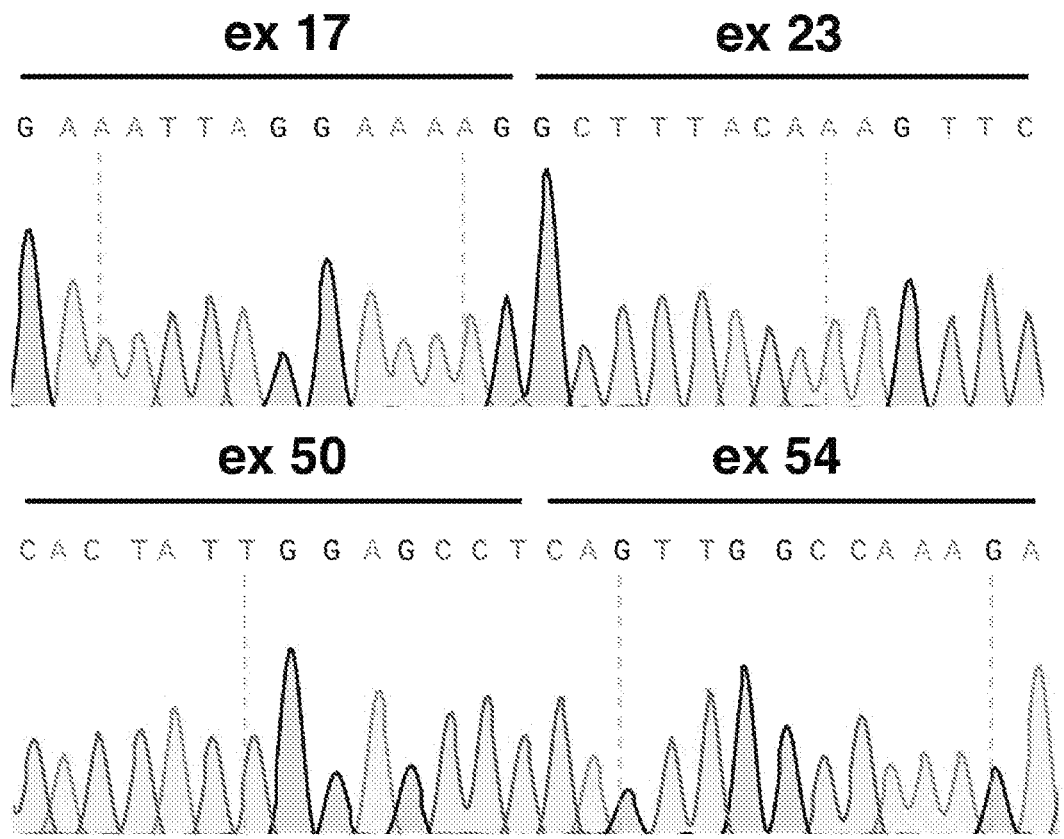

ASOs also are being evaluated therapeutically for another form of muscle disease, Duchenne muscular dystrophy (DMD), to modify dystrophin pre-mRNA splicing directly by inducing skipping of a target exon to restore the open reading frame and produce a truncated, partially functional protein[27, 28]. Detection of therapeutic drug effects in DMD patients involves multiple muscle biopsies to examine splicing outcomes and dystrophin protein production. To test whether biofluid exRNA contains DMD deletion transcripts, we examined urine from several subjects with DMD and found patient-specific DMD deletion transcripts (FIGS. 6A and B), suggesting this biofluid exRNA is a viable approach to monitor therapeutic exon-skipping ASO drug effects in DMD patients as personalized genetic markers[27, 28].

Example 5. Identification of a Novel DMD Cryptic Splice Site

Figure 6C:
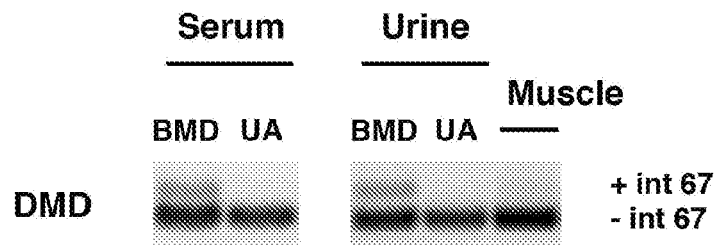
Figure 6D:
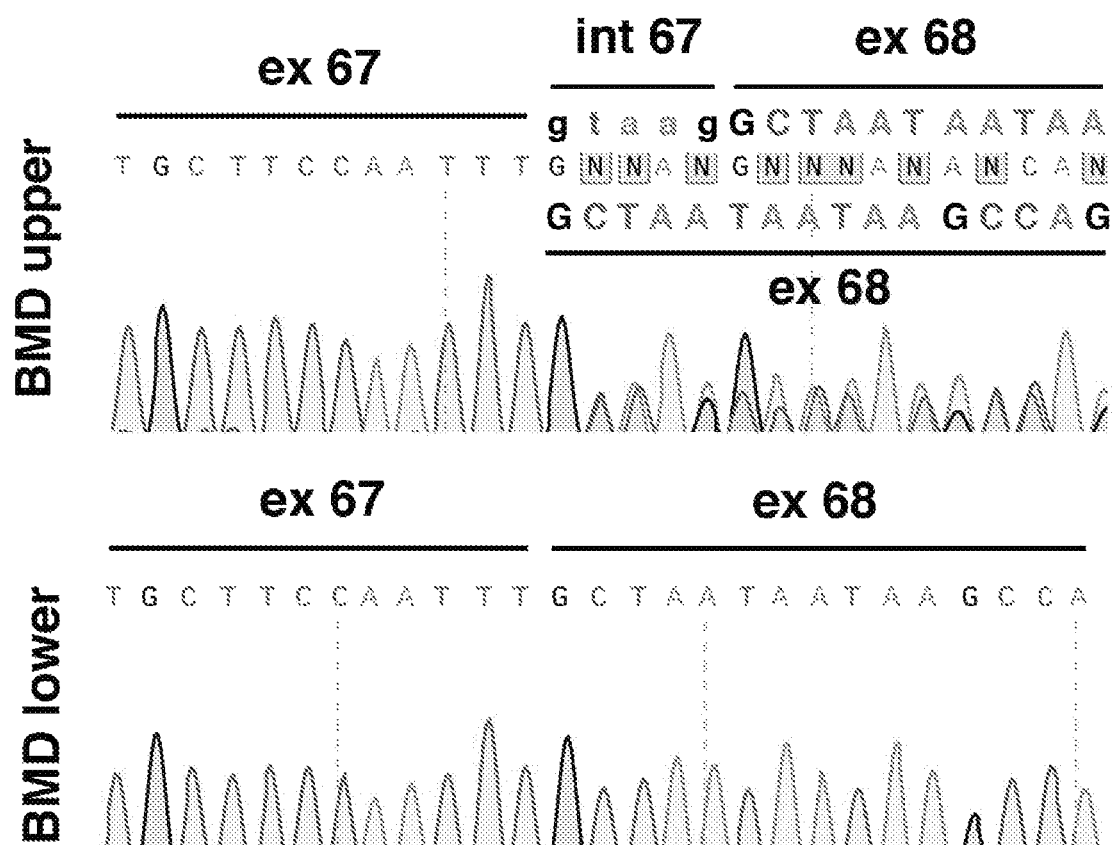

We also examined exRNA from a BMD patient with a normal DMD coding sequence, but a point mutation in intron 67 (c9807+6 T>G substitution). The normal coding sequence presumably produces a full-length dystrophin protein, suggesting the mutation in this patient causes dystrophinopathy by an overall reduction of dystrophin protein expression. RT-PCR analysis identified a splice product corresponding to the normal DMD exon 67-68 sequence in urine and serum from this patient and a UA subject, identical to muscle tissue (FIG. 6C). In addition, a second larger product unique to the BMD samples was evident. DNA sequencing confirmed the larger band was a heteroduplex containing the normal product identical to that in the lower band, as well as one with inclusion of the $1^{st}$ five nucleotides of intron 67, indicating a cryptic splice site (FIG. 6D) created by the mutation. The result is a frame shift and premature termination codon in exon 68, reducing functional dystrophin protein expression (FIG. 6E). Thus, urine exRNA also can be used to identify this molecular disease mechanism. The expression in the kidney of DMD transcripts spanning the deletions and point mutation (FIG. 12D) is consistent with the urinary tract as the primary source of exRNA in urine.

REFERENCES

1. Scotti, M. M. & Swanson, M. S. RNA mis-splicing in disease. *Nat Rev Genet* 17, 19-32 (2016).
2. Kanadia, R. N. et al. A muscleblind knockout model for myotonic dystrophy. *Science* 302, 1978-1980 (2003).
3. Lin, X. et al. Failure of MBNL1-dependent post-natal splicing transitions in myotonic dystrophy. *Hum Mol Genet* 15, 2087-2097 (2006).
4. Nakamori, M. et al. Splicing biomarkers of disease severity in myotonic dystrophy. *Ann Neurol* 74, 862-872 (2013).
5. Wheeler, T. M. et al. Reversal of RNA dominance by displacement of protein sequestered on triplet repeat RNA. *Science* 325, 336-339 (2009).
6. Wheeler, T. M. et al. Targeting nuclear RNA for in vivo correction of myotonic dystrophy. *Nature* 488, 111-115 (2012).
7. Clinicaltrials.gov https://clinicaltrials.gov/ct2/show/NCT02312011. (2016).
8. Pandey, S. K. et al. Identification and characterization of modified antisense oligonucleotides targeting DMPK in mice and nonhuman primates for the treatment of myotonic dystrophy type 1. *J Pharmacol Exp Ther* 355, 329-340 (2015).
9. Tkach, M. & Thery, C. Communication by Extracellular Vesicles: Where We Are and Where We Need to Go. *Cell* 164, 1226-1232 (2016).
10. Skog, J. et al. Glioblastoma microvesicles transport RNA and proteins that promote tumour growth and provide diagnostic biomarkers. *Nat Cell Biol* 10, 1470-1476 (2008).
11. Chen, W. W. et al. BEAMing and Droplet Digital PCR Analysis of Mutant IDH1 mRNA in Glioma Patient Serum and Cerebrospinal Fluid Extracellular Vesicles. *Mol Ther Nucleic Acids* 2, e109 (2013).
12. Nilsson, J. et al. Prostate cancer-derived urine exosomes: a novel approach to biomarkers for prostate cancer. *Br J Cancer* 100, 1603-1607 (2009).
13. San Lucas, F. A. et al Minimally invasive genomic and transcriptomic profiling of visceral cancers by next-generation sequencing of circulating exosomes. *Ann Oncol* 27, 635-641 (2016).

14. Khan, S et al. Early diagnostic value of survivin and its alternative splice variants in breast cancer. *BMC Cancer* 14, 176 (2014).
15. Neeb, A. et al. Splice variant transcripts of the anterior gradient 2 gene as a marker of prostate cancer. *Oncotarget* 5, 8681-8689 (2014).
16. Romancino, D. P. et al. Identification and characterization of the nano-sized vesicles released by muscle cells. *FEBS Lett* 587, 1379-1384 (2013).
17. Forterre, A. et al. Myotube-derived exosomal miRNAs downregulate Sirtuin1 in myoblasts during muscle cell differentiation. *Cell Cycle* 13, 78-89 (2014).
18. Hathout, Y. et al. Clinical utility of serum biomarkers in Duchenne muscular dystrophy. *Clin Proteomics* 13, 9 (2016).
19. Moeller, M. J. & Tenten, V. Renal albumin filtration: alternative models to the standard physical barriers. *Nat Rev Nephrol* 9, 266-277 (2013).
20. Noerholm, M. et al. RNA expression patterns in serum microvesicles from patients with glioblastoma multiforme and controls. *BMC Cancer* 12, 22 (2012).
21. Miranda, K. C. et al. Massively parallel sequencing of human urinary exosome/microvesicle RNA reveals a predominance of non-coding RNA. *PLoS One* 9, e96094 (2014).
22. Davis, B. M., McCurrach, M. E., Taneja, K. L., Singer, R. H. & Housman, D. E. Expansion of a CUG trinucleotide repeat in the 3' untranslated region of myotonic dystrophy protein kinase transcripts results in nuclear retention of transcripts. *Proc Natl Acad Sci USA* 94, 7388-7393 (1997).
23. Wagner, S. D. et al. Dose-Dependent Regulation of Alternative Splicing by MBNL Proteins Reveals Biomarkers for Myotonic Dystrophy. *PLoS Genet* 12, e1006316 (2016).
24. Motamedinia, P et al. Urine Exosomes for Non-Invasive Assessment of Gene Expression and Mutations of Prostate Cancer. *PLoS One* 11, e0154507 (2016).
25. Urquidi, V. et al. Urinary mRNA biomarker panel for the detection of urothelial carcinoma. *Oncotarget* 7, 38731-38740 (2016).
26. Mankodi, A. et al. Myotonic dystrophy in transgenic mice expressing an expanded CUG repeat. *Science* 289, 1769-1773 (2000).
27. Mendell, J. R. et al. Eteplirsen for the treatment of Duchenne muscular dystrophy. *Ann Neurol* 74, 637-647 (2013).
28. Kinali, M. et al. Local restoration of dystrophin expression with the morpholino oligomer AVI-4658 in Duchenne muscular dystrophy: a single-blind, placebo-controlled, dose-escalation, proof-of-concept study. *Lancet Neurol* 8, 918-928 (2009).
29. Erdbrugger, U. & Le, T. H. Extracellular Vesicles in Renal Diseases: More than Novel Biomarkers? *J Am Soc Nephrol* 27, 12-26 (2016).
30. Morcos, P. A., Li, Y. & Jiang, S. Vivo-Morpholinos: a non-peptide transporter delivers Morpholinos into a wide array of mouse tissues. *Biotechniques* 45, 613-614, 616, 618 passim (2008).
31. Aartsma-Rus, A. & Krieg, A. M. FDA Approves Eteplirsen for Duchenne Muscular Dystrophy: The Next Chapter in the Eteplirsen Saga. *Nucleic Acid Ther* 27, 1-3 (2017).
32. Eriksson, M. et al. Recurrent de novo point mutations in lamin A cause Hutchinson-Gilford progeria syndrome. *Nature* 423, 293-298 (2003).
33. Lee, J. M. et al. Modulation of LMNA splicing as a strategy to treat prelamin A diseases. *J Clin Invest* 126, 1592-1602 (2016).
34. Hua, Y. et al. Peripheral SMN restoration is essential for long-term rescue of a severe spinal muscular atrophy mouse model. *Nature* 478, 123-126 (2011).
35. Honda, D. et al. The ALS/FTLD-related RNA-binding proteins TDP-43 and FUS have common downstream RNA targets in cortical neurons. *FEBS Open Bio* 4, 1-10 (2013).
36. Genschel, J. & Schmidt, H. H. Mutations in the LMNA gene encoding lamin A/C. *Hum Mutat* 16, 451-459 (2000).
37. Imbeaud, S. et al. Towards standardization of RNA quality assessment using user-independent classifiers of microcapillary electrophoresis traces. *Nucleic Acids Res* 33, e56 (2005).
38. Savkur, R. S., Philips, A. V. & Cooper, T. A. Aberrant regulation of insulin receptor alternative splicing is associated with insulin resistance in myotonic dystrophy. *Nat Genet* 29, 40-47 (2001).
39. Koressaar, T. & Remm, M. Enhancements and modifications of primer design program Primer3. *Bioinformatics* 23, 1289-1291 (2007).
40. Untergasser, A. et al. Primer3—new capabilities and interfaces. *Nucleic Acids Res* 40, e115 (2012).
41. Mevik, B.-H. & Wehrens, R. The pls Package: Principal Component and Partial Least Squares Regression in R. *J Statistical Software* 18, 1-24 (2007).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method, comprising:
   obtaining a sample comprising urine from a subject who has, or is suspected to have, myotonic dystrophy type 1 (DM1);
   isolating extracellular mRNA in the sample;
   performing an assay to detect isoforms of mRNAs in the sample, wherein the mRNAs are:
   (i) transcripts for muscleblind like splicing regulator 2 (MBNL2); SOS Ras/Rac guanine nucleotide exchange factor 1 (SOS1); cytoplasmic linker associated protein 1 (CLASP1);
   muscleblind like splicing regulator 1 (MBNL1); and mitogen-activated protein kinase kinase kinase 4 (MAP3K4), or
   (ii) transcripts for MBNL2, MBNL1, SOS1, CLASP1, MAP3K4, and insulin receptor (INSR).

2. A method, comprising:
   obtaining a sample comprising urine from a subject who has, or is suspected to have, myotonic dystrophy type 1 (DM1);
   isolating extracellular mRNA in the sample;
   performing an assay to detect isoforms of mRNAs in the sample, wherein the mRNAs are transcripts for MBNL2; SOS1; CLASP1; MBNL1; and MAP3K4.

3. A method, comprising:
obtaining a sample comprising urine from a subject who has, or is suspected to have, myotonic dystrophy type 1 (DM1);
isolating extracellular mRNA in the sample;
performing an assay to detect isoforms of mRNAs in the sample, wherein the mRNAs are transcripts for MBNL2, MBNL1, SOS1, CLASP1, MAP3K4, and INSR.

* * * * *